US011865191B2

(12) United States Patent
Desai et al.

(10) Patent No.: US 11,865,191 B2
(45) Date of Patent: *Jan. 9, 2024

(54) COMPOSITIONS AND METHODS FOR ENHANCED FLUORESCENCE

(71) Applicants: Life Technologies Corporation, Carlsbad, CA (US); Pierce Biotechnology, Inc., Rockford, IL (US)

(72) Inventors: Surbhi Desai, Rockford, IL (US); Marie Christine Nlend, Rockford, IL (US); Kyle Gee, Springfield, OR (US); Matthew Baker, Rockford, IL (US); Robert Aggeler, Eugene, OR (US); Scott Sweeney, Eugene, OR (US); Aleksey Rukavishnikov, Eugene, OR (US); Shih-Jung Huang, Eugene, OR (US)

(73) Assignees: Life Technologies Corporation, Carlsbad, CA (US); Pierce Biotechnology, Inc., Rockford, IL (US)

(*) Notice: Subject to any disclaimer, the term of this patent is extended or adjusted under 35 U.S.C. 154(b) by 365 days.

This patent is subject to a terminal disclaimer.

(21) Appl. No.: 16/882,271

(22) Filed: May 22, 2020

(65) Prior Publication Data

US 2020/0330610 A1 Oct. 22, 2020

Related U.S. Application Data

(63) Continuation of application No. 15/693,772, filed on Sep. 1, 2017, now abandoned.

(60) Provisional application No. 62/382,594, filed on Sep. 1, 2016.

(51) Int. Cl.

| | | |
|---|---|---|
| A61K 49/00 | (2006.01) |
| G01N 33/58 | (2006.01) |
| A61K 47/10 | (2017.01) |
| A61K 47/08 | (2006.01) |
| G01N 33/533 | (2006.01) |
| G01N 33/68 | (2006.01) |
| A61K 47/18 | (2017.01) |

(52) U.S. Cl.
CPC .......... *A61K 49/0015* (2013.01); *A61K 47/10* (2013.01); *A61K 47/18* (2013.01); *A61K 49/0058* (2013.01); *G01N 33/533* (2013.01); *G01N 33/582* (2013.01); *G01N 33/68* (2013.01)

(58) Field of Classification Search
CPC .... A61K 47/10; A61K 47/18; A61K 49/0015; A61K 49/0058; G01N 33/533; G01N 33/582; G01N 33/68
See application file for complete search history.

(56) References Cited

U.S. PATENT DOCUMENTS

| | | | |
|---|---|---|---|
| 9,670,318 B2 | 6/2017 | Dose | |
| 2003/0088109 A1 | 5/2003 | Anderson et al. | |
| 2006/0234229 A1 | 10/2006 | Van Beuningen et al. | |
| 2010/0278750 A1 | 11/2010 | Krippner et al. | |
| 2012/0256102 A1 | 10/2012 | Kim et al. | |
| 2013/0052130 A1 | 2/2013 | Davis et al. | |
| 2014/0206099 A1 | 7/2014 | Mao et al. | |
| 2017/0313656 A1 | 11/2017 | Davis et al. | |
| 2020/0261602 A1* | 8/2020 | Desai | G01N 33/68 |
| 2020/0330610 A1 | 10/2020 | Desai et al. | |

FOREIGN PATENT DOCUMENTS

| | | |
|---|---|---|
| CN | 1832762 A | 9/2006 |
| CN | 101790684 A | 7/2010 |
| CN | 101827946 A | 9/2010 |
| CN | 101946171 A | 1/2011 |
| CN | 102692508 A | 9/2012 |
| CN | 103328532 A | 9/2013 |
| JP | 2010529186 A | 8/2010 |
| JP | 2012026879 A | 2/2012 |
| JP | 2015504943 A | 2/2015 |
| JP | 2015513551 A | 5/2015 |
| WO | WO-03102585 A2 | 12/2003 |
| WO | WO-2007120762 A2 | 10/2007 |
| WO | WO 2013/131884 | 9/2013 |
| WO | WO-2018045275 A1 | 3/2018 |

OTHER PUBLICATIONS

A printout retrieved from https://www.thermofisher.com/order/catalog/product/22341 on Aug. 1, 2023.*
A printout retrieved from https://www.lumiprobe.eom/t/fluorophores/hex on Aug. 3, 2023.*
A printout retrieved from https://pubs.acs.Org/doi/10.1021/jo202229t on Aug. 2, 2023.*
Rox Reference Dye, Invitrogen, Cat. No. 12223-012, Jan. 27, 2012, pp. 1-2.*
A printout retrieved from https://www.lumiprobe.eom/t/fluorophores/tet on Aug. 2, 2023.*
Amine-Reactive Probes, Molecular probes® by Life TechnologiesTM, Feb. 26, 2013, pp. 1-11.*
Hermanson G.T., "Bioconjugate Techniques," Academic press, 2nd Edition, 2008, pp. 156-158, 355, 364, 380, 398, 400-401, 817-819.
Andrew M Pickering et al: "A simple fluorescence labeling method for studies of protein oxidation. protein modification. and proteolysis", Free Radical Biology and Medicine. Elsevier Inc, US, vol. 52, No. 2, Aug. 18, 2011 (Aug. 18, 2011), pp. 239-246, XP028122108, ISSN: 0891-5849, DOI: 10.1016/J.FREERADBIOMED.2011.08.018 [retrieved on Sep. 14, 2011] p. 242. col 1. para 1.

(Continued)

*Primary Examiner* — Galina M. Yakovleva
(74) *Attorney, Agent, or Firm* — Klarquist Sparkman, LLP

(57) ABSTRACT

This disclosure relates to the field of fluorescent dyes, and in particular, compositions and methods for increasing fluorescent signals and the reduction of fluorescent quenching.

14 Claims, 24 Drawing Sheets

Specification includes a Sequence Listing.

(56) References Cited

OTHER PUBLICATIONS

Ex parte Johnson et al., Before the Board of Patent Appeals and Interferences, decided Dec. 30, 2009.
Flor, A. et al., "DNA-Directed Assembly of Antibody-Fiuorophore Conjugates for Quantitative Multiparametric Flow Cytometry", Chem Bio Chem, Full Paper, ChemPubSoc Europe, Wiley Online Library, 2014, pp. 267-275.
Hydrazide-FluoProbes® labels. PDF archived on Internet Sep. 10, 2016.
Knutson, et al., "Development and Evaluation of a Fluorescent Antibody-Drug Conjugate for Molecular Imaging and Targeted Therapy of Pancreatic Cancer", PLoS One. vol. 11, No. 6, Jun. 23, 2016,e0157762.
Morales, et al., "Biomolecule Labeling and Imaging with a New Fluorenyl Two-Photon Fluorescent Probe", Bioconiuaate Chemistrv. vol. 20, No. 10, Oct. 2, 2009, 1992-2000.
PCT/US2017/049838, "International Search Report", dated Feb. 1, 2018, 6 Pages.
Quiles et al., "Synthesis and Preliminary Biological Evaluation of High-drug Load Paclitaxel-Antibody Conjugates for Tumor-targeted Chemotherapy", Journal of Medicinal Chemistry, vol. 53, No. 2, 2010, pp. 586-594.
Ren, et al., "Star Polymers", Chemical Reviews, vol. 116, No. 12, Jun. 14, 2016, 6743-6836.
Rombouts, et al., "Fluorescent Labeling of Plasmid DNA and mRNA: Gains and Losses of Current Labeling Strategies", Bioconiuoate Chemistry, vol. 27, 2016, 280-297.
Office Action for corresponding Japanese Patent Application No. 2022-179386, dated Oct. 16, 2023 (2 pages), with English machine-translation.

\* cited by examiner

COMPOSITIONS AND METHODS FOR ENHANCED FLUORESCENCE

CROSS-REFERENCES TO RELATED APPLICATIONS

This application is a Continuation of U.S. application Ser. no. 15/693,772, filed Sep. 1, 2017, which is a which claims priority to U.S. application Ser. no. 62/382,594, filed Sep. 1, 2016, which disclosures are herein incorporated by reference in their entirety.

FIELD OF THE INVENTION

This disclosure relates to the field of fluorescent dyes, and in particular, compositions and methods for increasing fluorescent signals and the reduction of fluorescent quenching.

BACKGROUND

Fluorescently labeled biomolecules are widely used in various methods, including those related to quantitation assays and cellular imaging. Biomolecules such as antibodies, antigens, DNA, and RNA are fluorescently labeled and used in applications such as immunofluorescence (IFC), flow cytometry, Fluorescence-Activated Cell Sorting (FACS), immunohistochemistry (IHC), Western blotting, drug-binding studies, enzyme kinetics, imaging (immunocytochemistry ICC) including HCA, in vivo imaging, as well as in nucleic acid hybridizations. Fluorescent dyes continue to be chosen for these applications because they are easy to use and are not only specific and sensitive but also provide multiplexing options. However, not all applications have been amenable to fluorescent labeling. For example, in many applications the intensity of the fluorescence may be decreased as increased quantities of fluorescent label (high dye to protein ratios) are added to biomolecules (quenching). Moreover, fluorescence may also be decreased through steric hindrance caused by fluorescent labeling of the biomolecule. There is a need for fluorescent labels and conjugation methods that exhibit enhanced signal strength.

SUMMARY

Disclosed herein are compositions and methods for increasing intensity of a fluorescent dye conjugated to a biomolecule through, for example, modified linkers, chemistries and specified protocols. One aspect of the invention is thus to improve the performance of dyes. It has been found that fluorescence intensity may be increased when a biomolecule is labeled with both a dye and a spacer molecule as compared to the corresponding conjugate made with the dye alone. Conjugates made with these spacer molecules show fluorescence enhancement in Western blotting, dot blot assays, plate assays, flow cytometry and immunoassay applications (e.g., immunofluorescence imaging applications).

Further, enhanced fluorescence is seen even when fewer dye molecules are associated with (covalently or non-covalently) each biomolecule. This effect is believed to be associated with the attachment of spacer groups to the biomolecules that exhibit enhanced fluorescence. While not wishing to be bound to theory, it is believed that the enhanced fluorescence results from decreased quenching of dye emissions. In some aspects, the invention is directed, in part, to compositions comprising a first biomolecule (e.g., a first antibody), wherein two or more fluorescent labels and two or more spacer molecules are covalently attached to the first biomolecule, and wherein the fluorescent and spacer molecules are not covalently attached to each other. In some instances, the first biomolecule (e.g., a first antibody) exhibits higher fluorescent emission levels than a second biomolecule (e.g., a second antibody) prepared with an equivalent amount of fluorescent label but without the spacer. In additional instances, the first biomolecule exhibits higher fluorescent emission levels than the second biomolecule, wherein the first biomolecule and the second biomolecule each have the same number of covalently bound fluorescent labels, and wherein the second biomolecule does not have covalently bound spacers. In specific embodiments, the spacer molecules reduce quenching of the fluorescent labels as compared to the quenching in the absence of spacer.

In some aspects of the invention, the spacer molecules are conjugated to the biomolecule through a reactive group. Such reactive groups may be amine reactive groups (e.g. NHS esters, the amine group or groups may be at the amine terminus of a polypeptide and/or lysine side chains), sulfhydryl groups, carboxylic acid groups, etc. Additional groups to which spacer molecules may be conjugated include cysteine residues, aspartic acid residues, glutamic acid residues and/or the carboxy terminus of a polypeptide. Further, fluorescent labels may be conjugated to the biomolecule by a conjugation arm. These fluorescent labels may be positively charged, neutral, and/or negatively charged.

In some embodiments, fluorescent labels used in the practice of the invention (both compositions and methods) may be cyanine, benzo-rhodamne, bodipy, fluorescein, benzopyrillium derivatives and further include ALEXA FLUOR® dye and/or DYLIGHT™ dyes. Such dyes may be selected from the group consisting of ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610-X, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, AMCA-X, BODIPY® 630/650, BODIPY® 650/665, BODIPY® FL, BODIPY® TMR, BODIPY® TR, BODIPY® TR-X, CASCADE BLUE®, Dinitrophenyl, Fluorescein, HEX, JOE, MARINA BLUE®, OREGON GREEN® 488, OREGON GREEN® 514, PACIFIC BLUE™, PACIFIC ORANGE™, RHODAMINE GREEN™, QSY® 7, QSY® 9, QSY® 21, QSY® 35, ROX, RHODAMINE RED™, TET, TAMRA, tetramethyl rhodamine, FAM, TEXAS RED®, 7-hydroxy-9H-(1,3-dichloro-9,9-dimethylacridin-2-one) succinimidyl ester (DDAO-SE), DYLIGHT™ 350, DYLIGHT™ 405, DYLIGHT™ 488, DYLIGHT™ 550, DYLIGHT™ 594, DYLIGHT™ 633, DYLIGHT™ 650, DYLIGHT™ 680, DYLIGHT™ 755, and DYLIGHT™ 800. Of course, other dyes, as well as modified forms of the above dyes, may be used in the practice of the invention.

The spacer may be negatively or neutrally charged may be used in the practice of the invention. Further, the spacer may be selected from, for example, acetate and polyethylene glycol (PEG). Spacers may comprises an acetyl group and may be an acetate molecule (e.g., sulfo-NHS-acetate). Further, spacers may comprise or consist of (PEG)n, wherein n is selected from 1, 2, 3, 4, 5, 6, 7, 8, 9, 10, 11, 12, 13, 14 or 15 and/or MS-(PEG)n, wherein n is selected from 1, 2, 3, 4, 5, 6, 7, 8, 9, 10, 11, 12, 13, 14 or 15.

Further, spacers used in the practice of the invention may comprise or consist of one or more group selected from an alkanoyl, alkenoyl, and alkynoyl (—C(O)$C_nH_m$), wherein n is 1 to 20 atoms, wherein m>n, wherein the carbon atoms can be connected to each other by single, double, and/or triple bonds. Alkyl, alkenyl, and/or alkynyl groups may be further substituted with —(OCH$_2$CH$_2$O)$_x$—(CH$_2$)$_y$—OR, in which x is 1 to 20, y is 1 to 6, and R is H or C$_{1-6}$ alkyl. Additionally, the alkyl, alkenyl, and/or alkynyl groups may be further substituted with ammonium (—NH$_3^+$), quaternary ammonium (—NR$_3^+$) groups in which R is C$_{1-6}$ alkyl.

Further, in specific embodiments of the invention, the fluorescent dye may comprises one or more ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610-X, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, AMCA-X, BODIPY® 630/650, BODIPY® 650/665, BODIPY® FL, BODIPY® TMR, BODIPY® TR, BODIPY® TR-X, CASCADE BLUE®, Dinitrophenyl, Fluorescein, HEX, JOE, MARINA BLUE®, OREGON GREEN® 488, OREGON GREEN® 514, PACIFIC BLUE™, PACIFIC ORANGE™, RHODAMINE GREEN™, QSY® 7, QSY® 9, QSY® 21, QSY® 35, ROX, RHODAMINE RED™, TET, TAMRA, tetramethyl rhodamine, FAM, TEXAS RED®, or 7-hydroxy-9H-(1,3-dichloro-9,9-dimethylacridin-2-one) succinimidyl ester (DDAO-SE); and the spacer may comprise one or more of sulfo-NHS-acetate; (PEG)n, wherein n is selected from 1, 2, 3, 4, 5, 6, 7, 8, 9, 10, 11, 12, 13, 14 or 15; MS-(PEG)n, wherein n is selected from 1, 2, 3, 4, 5, 6, 7, 8, 9, 10, 11, 12, 13, 14 or 15; alkanoyl, alkenoyl, or alkynoyl (—C(O)C$_n$H$_m$), wherein n is 1 to 20 atoms, wherein m>n, wherein the carbon atoms can be connected to each other by single, double, and/or triple bonds; or alkyl, alkenyl, or alkynyl groups that are further substituted with —(OCH$_2$CH$_2$O)$_x$—(CH$_2$)$_y$—OR, in which x is 1 to 20, y is 1 to 6, and R is H or C$_{1-6}$ alkyl or wherein the alkyl, alkenyl, and/or alkynyl groups are further substituted with ammonium (—NH$_3^+$), quaternary ammonium ((—NR$_3^+$) groups in which R is C$_{1-6}$ alkyl. Further, alkyl, alkenyl, and/or alkynyl groups may be further substituted with phosphonium groups (—PQ$_3^+$) in which Q is aryl, substituted aryl, or C$_{1-6}$ alkyl.

Compositions and methods of the invention may contain or use fluorescently labeled biomolecules (e.g., antibodies), wherein the ratio of fluorescent label to biomolecule is from 1 to 50, from 5 to 30, or from 1 to 20. Compositions and methods of the invention may contain or use fluorescently labeled biomolecules (e.g., antibodies), wherein the spacer agent to biomolecule ratio is from 1 to 50, from 5 to 30, from 5 to 30, or from 1 to 20.

Additionally, compositions and methods of the invention may contain or use fluorescently labeled biomolecules (e.g., antibodies), wherein the spacer agent is in molar excess to the plurality of fluorescent labels in an amount from 0.1 to 25, from 1 to 15, or from 2.5 to 10 fold; wherein the spacer agent is in molar excess to the plurality of fluorescent labels in an amount of 2.5 fold; wherein the spacer agent is in molar excess to the plurality of fluorescent labels in an amount of 5 fold; wherein the spacer agent is in molar excess to the plurality of fluorescent labels in an amount of 7.5 fold; or wherein the spacer agent is in molar excess to the plurality of fluorescent labels in an amount of 10 fold.

Further, compositions and methods of the invention may contain or use fluorescently labeled biomolecules (e.g., antibodies), wherein the percentage of binding sites on the biomolecule (e.g., accessible amine groups) occupied by the plurality of fluorescent labels is between 1% and 99%.

In some embodiments, the presence of the spacer increases the detectable fluorescence of the fluorescent label by at least 20%, at least 30%, at least 40%, at least 50%, at least 60%, at least 70%, at least 80%, at least 90%, at least 100%, at least 125%, at least 150%, at least 200%, at least 300%, at least 400%, or at least 500%.

The invention is also directed, in part, to methods for increasing fluorescence of a fluorescently labeled biomolecule. Such methods include those comprising: (a) conjugating a spacer molecule to a biomolecule; and (b) conjugating a fluorescent label to the biomolecule; wherein steps (a) and (b) can be done simultaneously or in any order, and wherein the spacer and fluorescent label are not conjugated to each other. Further, the spacer molecules may reduce quenching of the fluorescent labels as compared to the amount of quenching that occurs in the absence of spacer.

The invention is also directed, in part, to methods for identifying a spacer molecule capable of enhancing the fluorescent emission fluorescently labeled biomolecule. Such methods may comprise: (a) conjugating a spacer molecule to a biomolecule, independent of the plurality of fluorescent labels conjugated to the biomolecule; (b) testing whether the presence of the spacer agent in addition to the plurality of fluorescent labels conjugated to the biomolecule increases the detectable fluorescence of the plurality of fluorescent labels; and (c) identifying the spacer agent as one that will reduce quenching of the fluorescent label conjugated to the protein when the presence of the spacer agent in addition to the plurality of fluorescent labels conjugated to the biomolecule increases the detectable fluorescence of the plurality of fluorescent labels. In some instances, the spacer agent is conjugated to the biomolecule at primary lysine side chains present on the biomolecule. Further, the biomolecule is an antibody or antibody fragment. Also, the plurality of fluorescent labels may be negatively and/or positively charged. Additionally, the spacer agents may be negatively and/or positively charged.

The invention is further directed, in part to methods for determining the presence of a desired target in a biological sample. Such methods may comprise: (a) contacting the biological sample with a composition an antibody, wherein two or more fluorescent labels and two or more spacer molecules are covalently attached to the antibody, wherein the fluorescent and spacer molecules are not covalently attached to each other, (b) detecting fluorescence emitted by the plurality of fluorescent labels; and (c) determining the presence of the desired target in the biological sample when fluorescence emitted by the plurality of fluorescent labels is detected. Biological samples used in the practice of the invention may comprise cell lysates, intact cells (e.g., intact cells in fluid, such as bodily fluids), isolated proteins, and/or recombinant proteins. Further, the biological sample may be immobilized on a solid support. Further, biological sample include live animals, such as mammals.

The invention is also directed, in part, to compositions comprising a first nucleic acid molecule, wherein two or more fluorescent labels and two or more spacer molecules are covalently attached to the first nucleic acid molecule, and wherein the fluorescent and spacer molecules are not covalently attached to each other. In some embodiments, the first nucleic acid molecule may exhibit a higher fluorescent emission levels than a second nucleic acid molecule prepared with an equivalent amount of fluorescent label but without the spacer. Further, in some embodiments, the first nucleic acid molecule may exhibit a higher fluorescent emission levels than a second nucleic acid molecule, wherein the first nucleic acid molecule and the second nucleic acid molecule each have the same number of covalently bound fluorescent labels, and wherein the second nucleic acid molecule does not have a covalently bound spacers.

The invention also includes conjugated antibodies comprising antibody each conjugated to a plurality of fluorescent labels (e.g., and average of from about two to about thirty, from about two to about twenty, from about three to about thirty, from about two to about fifteen, from about three to about fifteen, from about four to about thirty, from about six to about twenty, from about seven to about thirty, etc.), wherein the conjugated antibodies comprises one or more of the following characteristics:
  (a) a Fluorescent Ratio on a per fluorescent label basis that is equal to or greater than 0.5,
  (b) at least four fluorescent labels are conjugated to the antibody,
  (c) the total fluorescence of the antibody is at least 20 percent greater than the fluorescence of the unconjugated fluorescent molecule, and/or
  (d) an average of from about 3 to about 80 fluorescent labels attached to each of the antibody molecules.

Further, the fluorescent labels may be conjugated to biomolecules (e.g., antibodies) by one or more (e.g., from about one to about fifteen, from about two to about ten, from about two to about fifteen, from about two to about eight, from about three to about ten, from about three to about six, etc.) multi-armed polymers. Additionally, the arms of the multi-armed polymer may be composed of a chemical of a type selected from the group consisting of: (a) a polyethylene glycol, (b) a polysaccharide, and (c) a polypeptide, as well as other materials. Further, the average brush distance between the fluorescent labels may be between 200 to 800 Angstroms (e.g., from about 200 to about 700, from about 300 to about 800, from about 400 to about 800, from about 500 to about 800, from about 200 to about 600, from about 500 to about 800, from about 300 to about 700, from about 350 to about 800, etc.). Also, the fluorescent labels conjugated to the antibody (or other biomolecule) may be separated from the antibody (or other biomolecule) by at least 16 (e.g., from about 16 to about 800, from about 25 to about 800, from about 40 to about 800, from about 60 to about 800, from about 100 to about 800, from about 200 to about 800, from about 250 to about 800, from about 150 to about 600, etc.) covalent bonds. Additionally, the conjugated antibody (or other biomolecule) may be conjugated to fluorescent labels which may be one or more dye selected from the group consisting of ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610-X, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, AMCA-X, BODIPY® 630/650, BODIPY® 650/665, BODIPY® FL, BODIPY® TMR, BODIPY® TR, BODIPY® TR-X, CASCADE BLUE®, Dinitrophenyl, Fluorescein, HEX, JOE, MARINA BLUE®, OREGON GREEN® 488, OREGON GREEN® 514, PACIFIC BLUE™, PACIFIC ORANGE™, RHODAMINE GREEN™, QSYR 7, QSYR 9, QSYR 21, QSYR 35, ROX, RHODAMINE RED™, TET, TAMRA, tetramethyl rhodamine, FAM, TEXAS RED®, or 7-hydroxy-9H-(1,3-dichloro-9,9-dimethylacridin-2-one) succinimidyl ester (DDAO-SE); and fluorescent labels from the group consisting of DYLIGHT™ 350, DYLIGHT™ 405, DYLIGHT™ 488, DYLIGHT™ 550, DYLIGHT™ 594, DYLIGHT™ 633, DYLIGHT™ 650, DYLIGHT™ 680, DYLIGHT™ 755, and DYLIGHT™ 800 and pegylated DYLIGHT™ dyes.

The invention also includes method for preparing fluorescently labeled biomolecules, these method may comprising: (a) conjugating a reactive group and two or more fluorescent labels to a spacer molecule, thereby forming a fluorescently labeled spacer molecule, and (b) conjugating the fluorescently labeled spacer molecule to the biomolecule, thereby forming the fluorescently labeled biomolecule, wherein the individual fluorescent labels of the fluorescently labeled biomolecule have a Fluorescent Ratio on a per fluorescent label basis that is equal to or greater than 0.5. Further, an average of from one to ten (e.g., from about one to about nine, from about two to about ten, from about three to about ten, from about four to about ten, from about five to about ten, from about two to about six, from about three to about six, from about three to about seven, etc.) fluorescently labeled spacer molecules may be conjugated to each biomolecule. Additionally, the fluorescently labeled spacer molecule may be a multi-armed polymer (e.g., a branched polyethylene glycol molecule). Further, spacer molecules (e.g., multi-armed polymers) may each be conjugated to an average of between 4 and 20 (e.g., from about 4 to about 10, from about 3 to about 8, from about 4 to about 8, from about 3 to about 9, etc.) fluorescent labels. Further, spacer molecules (e.g., the multi-armed polymers) may have a molecular weight between 4,000 and 80,000 daltons (e.g., from about 4,000 to about 70,000, from about 4,000 to about 60,000, from about 4,000 to about 50,000, from about 4,000 to about 40,000, from about 10,000 to about 70,000, from about 15,000 to about 60,000, etc.).

The invention further includes method for detecting fluorescently labeled biomolecules. Such methods may comprise: (a) exposing the fluorescently labeled biomolecule (e.g., an antibody) with light that excites fluorescent labels conjugated to the biomolecule and (2) detecting emitted light produced by the fluorescent labels conjugated to the biomolecule. In some instances, the fluorescently labeled biomolecule may be conjugated to four or more fluorescent labels. Further, the individual fluorescent labels of the fluorescently labeled biomolecule may have a Fluorescent Ratio on a per fluorescent label basis that is equal to or greater than 0.7 (e.g., from about 0.7 to about 1.0, from about 0.7 to about 0.95, from about 0.7 to about 0.9, from about 0.7 to about 0.85, from about 0.75 to about 0.95, etc.).

TABLE 1

| Lane | Dye/Spacer |
|---|---|
| 1 | DYLIGHT ™ 488-5X, No Spacer |
| 2 | DYLIGHT ™ 488-5X, 2.5X NHS Acetate |
| 3 | DYLIGHT ™ 488-5X, 5X NHS Acetate |
| 4 | Blank Well |
| 5 | DYLIGHT ™ 488-5X, 3.75X MS(PEG)$_4$ |
| 6 | DYLIGHT ™ 488-5X, 5X MS(PEG)$_4$ |
| 7 | DYLIGHT ™ 488-5X, 10X MS(PEG)$_4$ |
| 8 | DYLIGHT ™ 488-7.5X, No Spacer |
| 9 | DYLIGHT ™ 488-7.5X, 2.5X NHS Acetate |
| 10 | DYLIGHT ™ 488-7.5X, 5X NHS Acetate |
| 11 | Blank Well |
| 12 | DYLIGHT ™ 488-7.5X, 3.75X MS(PEG)$_4$ |
| 13 | DYLIGHT ™ 488-7.5X, 5X MS(PEG)$_4$ |
| 14 | DYLIGHT ™ 488-7.5X, 10X MS(PEG)$_4$ |
| 15 | DYLIGHT ™ 488-10X, No Spacer |
| 16 | DYLIGHT ™ 488-10X, 2.5X NHS Acetate |
| 17 | DYLIGHT ™ 488-10X, 5X NHS Acetate |
| 18 | Blank Well |
| 19 | DYLIGHT ™ 488-10X, 3.75X MS(PEG)$_4$ |
| 20 | DYLIGHT ™ 488-10X, 5X MS(PEG)$_4$ |
| 21 | DYLIGHT ™ 488-10X, 10X MS(PEG)$_4$ |
| 22 | DYLIGHT ™ 488-15X, No Spacer |
| 23 | DYLIGHT ™ 488-15X, 2.5X NHS Acetate |
| 24 | DYLIGHT ™ 488-15X, 5X NHS Acetate |
| 25 | DYLIGHT ™ 488-15X, 10X NHS Acetate |
| 26 | DYLIGHT ™ 488-15X, 3.75X MS(PEG)$_4$ |
| 27 | DYLIGHT ™ 488-15X, 5X MS(PEG)$_4$ |
| 28 | DYLIGHT ™ 488-15X, 10X MS(PEG)$_4$ |
| 29 | DYLIGHT ™ 488-20X, No Spacer |
| 30 | DYLIGHT ™ 488-20X, 2.5X NHS Acetate |
| 31 | DYLIGHT ™ 488-20X, 5X NHS Acetate |
| 32 | DYLIGHT ™ 488-20X, 10X NHS Acetate |
| 33 | DYLIGHT ™ 488-20X, 3.75X MS(PEG)$_4$ |
| 34 | DYLIGHT ™ 488-20X, 5X MS(PEG)$_4$ |
| 35 | DYLIGHT ™ 488-20X, 10X MS(PEG)$_4$ |

Figure 1:
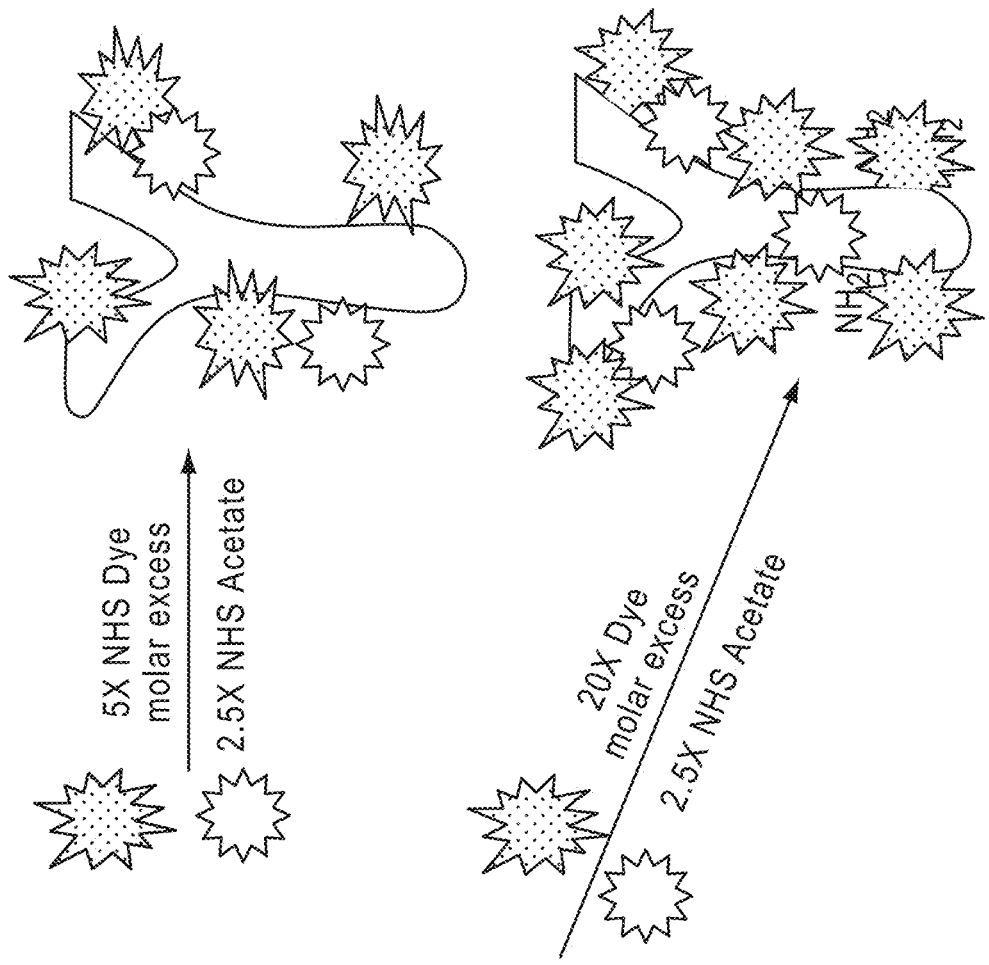
FIG. 1 shows a schematic representation of one embodiment of the invention. In this embodiment, an antibody is conjugated with NHS fluorescent dyes at two different dye molar excesses and a Sulfo NHS-Acetate spacer in 50 mM borate buffer pH 8.5. Conjugation of the dye and spacer result in enhanced sensitivity and reduced quenching.
Figure 1:
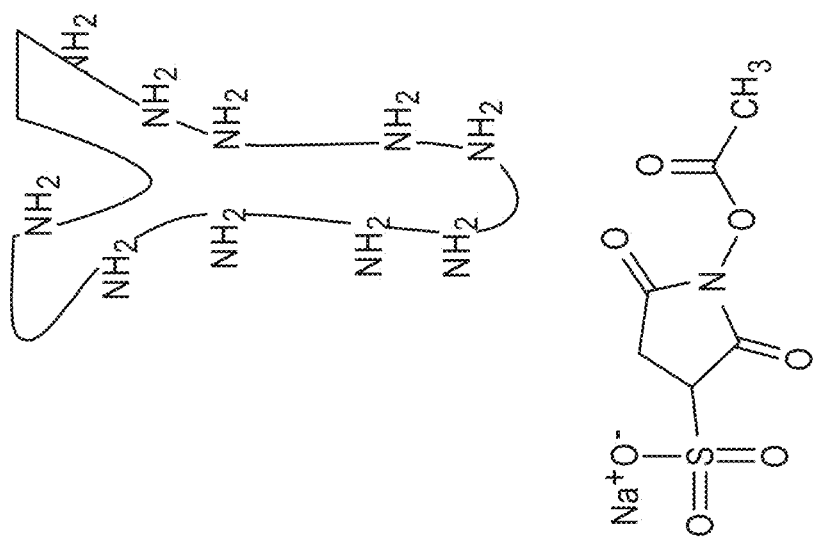
Figure 2:
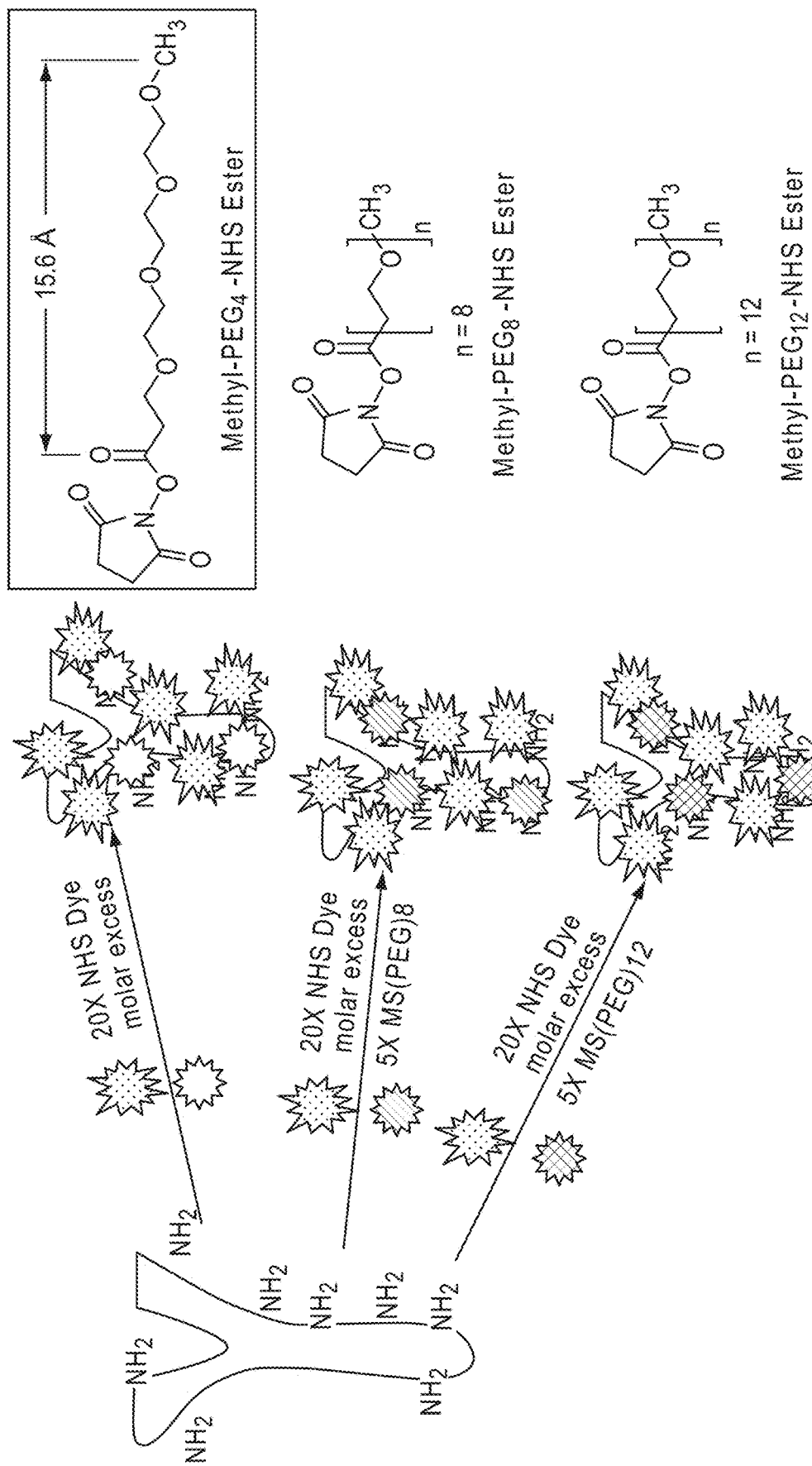
FIG. 2 shows a schematic representation of some embodiments of the invention. In this embodiment, an antibody is conjugated to NHS-fluorescent dyes and a methyl-PEG-NHS-ester spacer in 50 mM borate buffer pH 8.5. The spacers used in this embodiment are MS(PEG)$_4$, MS(PEG)$_8$ and MS(PEG)$_{12}$.
Figure 3:
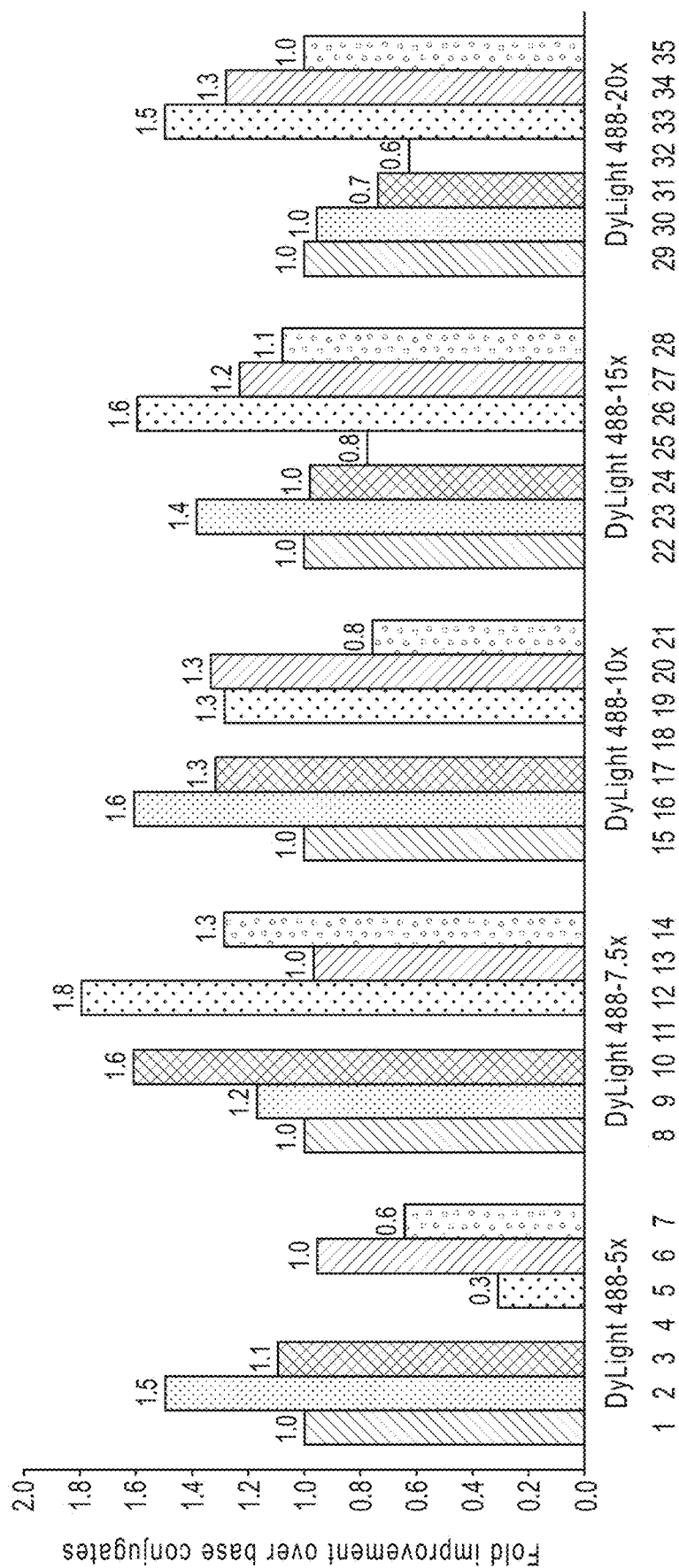
FIG. 3 shows results from a software analysis of a dot blot captured using an imaging instrument. The dot blot was tested with GAM antibodies co-labeled with NHS acetate or MS(PEG)$_4$ spacers and DYLIGHT™ 488 fluorescent dye (abbreviated in Table 1 "DYLIGHT™ 488"). DYLIGHT™ 488-GAM conjugates made with NHS Acetate or MS(PEG)$_4$ resulted in a 1.2 to 1.8-fold improvement in fluorescent intensity ranging from 1.2 to 1.8-fold over the base conjugate (made without the spacer). Lanes of this figures are as follows.
Figure 4:
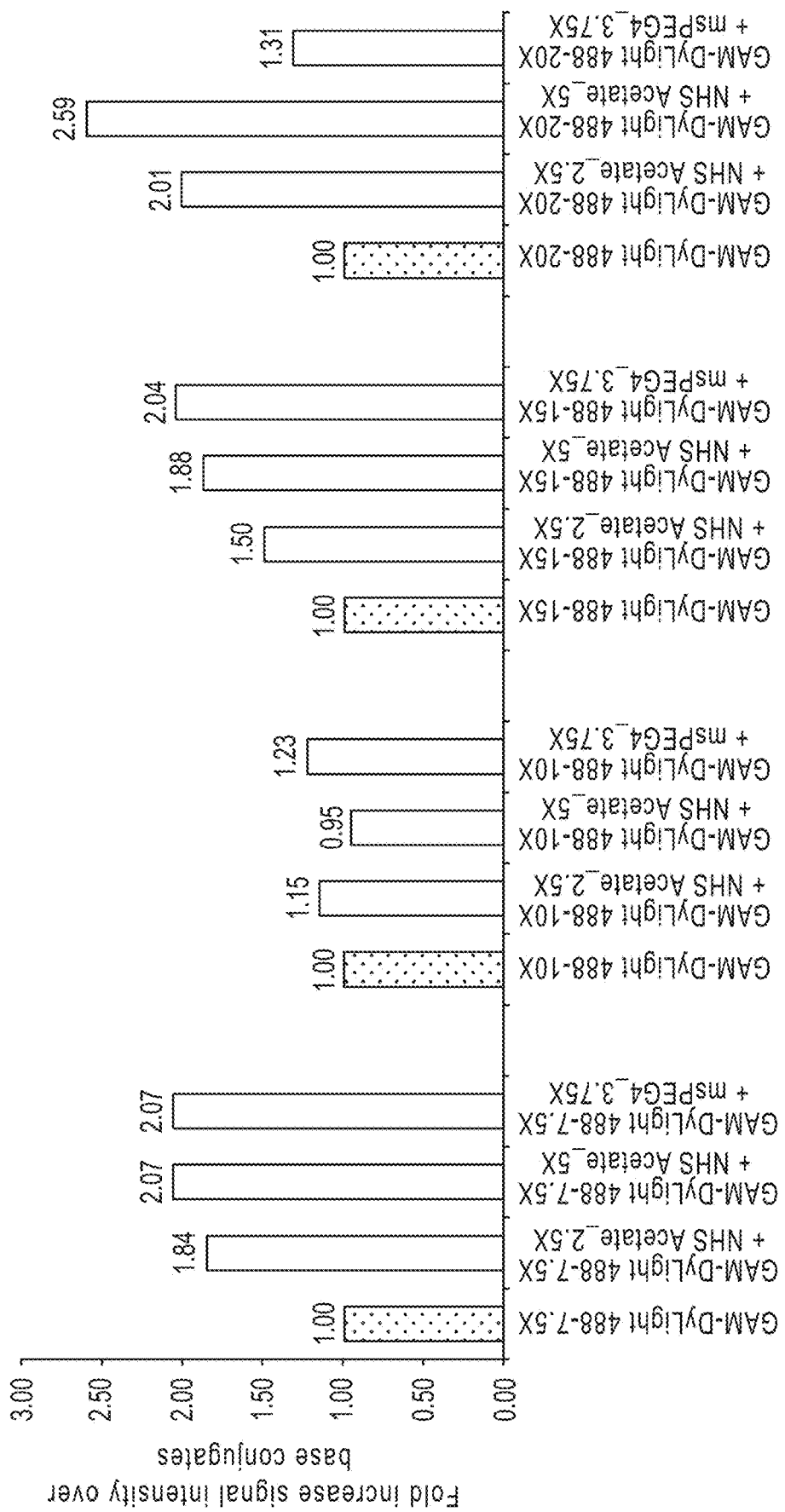

FIG. 4: Dot Blot—DYLIGHT™ 488-GAM detection of Mouse IgG Fold improvement from NHS Acetate (2.5x, 5x) or MS(PEG)$_4$ (3.75x) over base conjugates at dye various molar excesses. This figure shows results from a software analysis of a dot blot captured using an imaging instrument. The dot blot was tested with an assay using GAM antibodies co-labeled with NHS acetate or MS(PEG)$_4$ spacers and DYLIGHT™ 488 fluorescent dye. These data confirmed results from FIG. 3 using another source for the antibody. Both NHS acetate and MS(PEG)$_4$ spacers provided significant improvement (as much as about a 2.6 increase) in fluorescent signal intensity as compared to antibody-dye conjugates alone.

Figure 5:
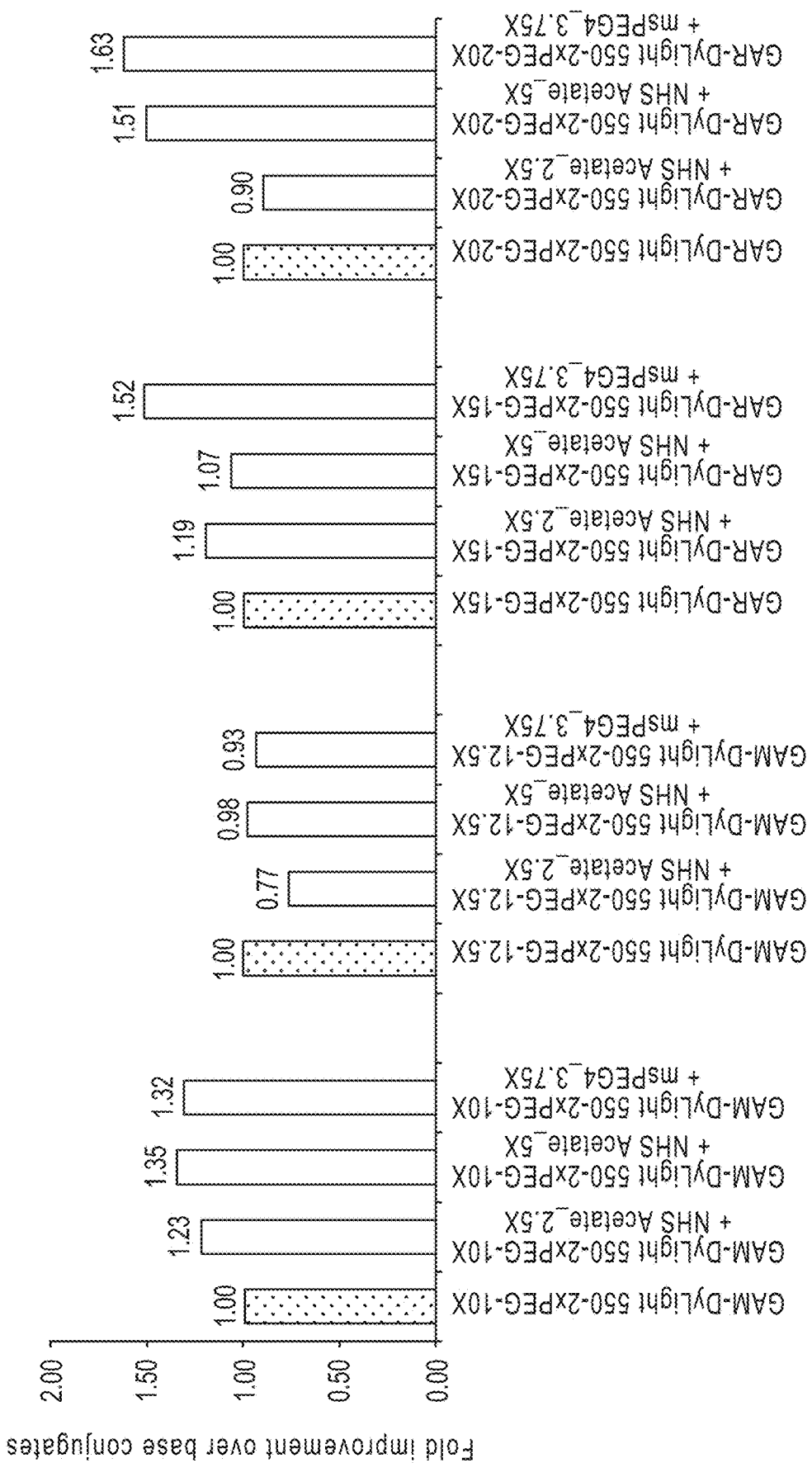

FIG. 5: Dot Blot—Detection of Mouse IgG with DYLIGHT™ 550-2xPEG-GAR. Signal/background fold improvement from NHS Acetate (2.5x, 5x) or MS(PEG)$_4$ (3.75x) over base conjugates at various molar excesses. This shows results from a software analysis of a dot blot captured using an imaging instrument. The dot blot was tested with DYLIGHT™ 550-GAM antibodies co-labeled with NHS Acetate or MS(PEG)$_4$ spacers and DYLIGHT™ 550 fluorescent dye. Mouse IgG was serially diluted 1:1 from 1000 ng/dot. All DYLIGHT™ 550-2xPEG-GAR secondary antibodies were diluted 1/5000 of 1 mg/ml stock. NHS acetate or MS(PEG)$_4$ added to the conjugation mix provided an improvement (as much as about a 1.6 increase) of signal intensity as compared to the base conjugates at each respective dye molar excesses. Improvement ranged from 1.2 to 1.6-folds; notably for the following GAM-DYLIGHT™ 550-2xPEG: 10x Dye+5x Acetate, 15x Dye+3.75x MS(PEG)$_4$, 20x Dye+5x Acetate, and 20x+3.75x MS(PEG)$_4$ that showed an improvement of greater than 1.3-fold over the respective base conjugates.

Figure 6:
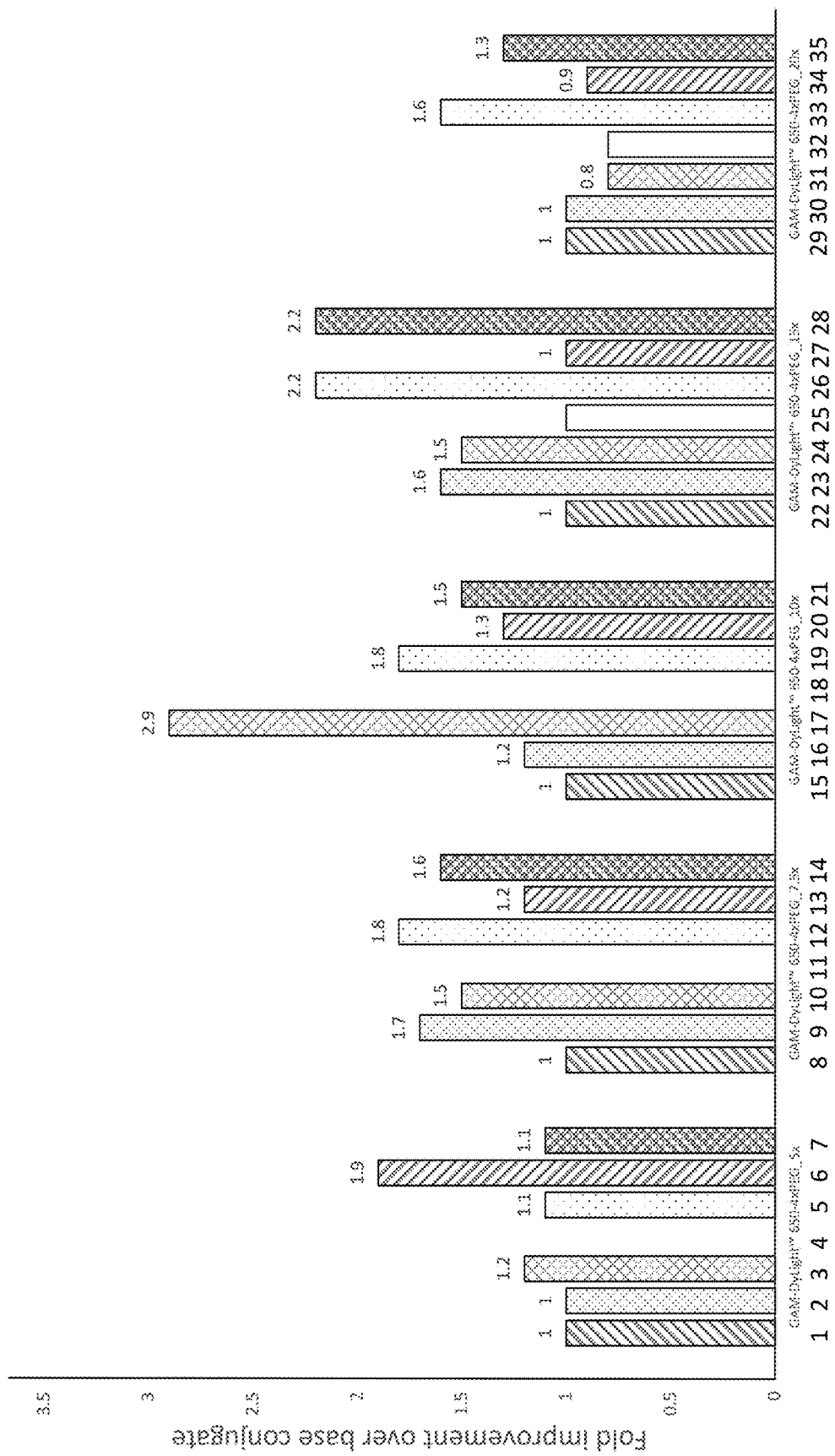

FIG. 6: Dot Blot—DyLight 650-4XPEG-GAM detection of Mouse IgG Fold improvement from NHS Acetate (2.5x, 5x and 10x) or MS(PEG)$_4$ (3.75x, 5x, 10x) over base conjugates at each dye molar excess. This figure shows results from a software analysis of a dot blot captured using an imaging instrument. The dot blot was tested with GAM antibodies co-labeled with NHS Acetate (2.5x, 5x and 10x) or MS(PEG)$_4$ (3.75x) and DYLIGHT™ 650-4xPEG (abbreviated in Table 2 "DYLIGHT™ 650") at (10x-20x). Mouse IgG was serially diluted 1:1 from 1000 ng/dot. All DYLIGHT™ 650-4xPEG-GAR secondary antibodies were diluted 1/10,000 of 1 mg/ml stock. Conjugates with high dye substitution tend to perform better in applications such as Dot Blot and western blotting. Both NHS Acetate and (MS)PEG$_4$ bring significant improvement in sensitivity and signal/background (as much as about a 2.2 increase) over the initial base conjugates. NHS acetate added at 2.5x molar excess to GAM-DYLIGHT™ 650-4xPEG-15x improved intensity by 1.7-fold. The improvement provided by NHS Acetate showed 1.3-fold better performance than with the conjugate prepared with the highest molar excess (20x). All MS(PEG)$_4$ added to GAM-DYLIGHT™ 650-4xPEG-15x conjugation improved fluorescence intensity by 1.8 to 2.2-fold and performed better than the corresponding highest base conjugate GAM-DYLIGHT™ 650-4xPEG-20x. Lanes of this figures are as follows:

TABLE 2

| Lane | Dye/Spacer |
|---|---|
| 1 | DYLIGHT ™ 650-5X, No Spacer |
| 2 | DYLIGHT ™ 650-5X, 2.5X NHS Acetate |
| 3 | DYLIGHT ™ 650-5X, 5X NHS Acetate |
| 4 | Blank Well |

TABLE 2-continued

| Lane | Dye/Spacer |
|---|---|
| 5 | DYLIGHT™ 650-5X, 3.75X MS(PEG)$_4$ |
| 6 | DYLIGHT™ 650-5X, 5X MS(PEG)$_4$ |
| 7 | DYLIGHT™ 650-5X, 10X MS(PEG)$_4$ |
| 8 | DYLIGHT™ 650-7.5X, No Spacer |
| 9 | DYLIGHT™ 650-7.5X, 2.5X NHS Acetate |
| 10 | DYLIGHT™ 650-7.5X, 5X NHS Acetate |
| 11 | Blank Well |
| 12 | DYLIGHT™ 650-7.5X, 3.75X MS(PEG)$_4$ |
| 13 | DYLIGHT™ 650-7.5X, 5X MS(PEG)$_4$ |
| 14 | DYLIGHT™ 650-7.5X, 10X MS(PEG)$_4$ |
| 15 | DYLIGHT™ 650-10X, No Spacer |
| 16 | DYLIGHT™ 650-10X, 2.5X NHS Acetate |
| 17 | DYLIGHT™ 650-10X, 5X NHS Acetate |
| 18 | Blank Well |
| 19 | DYLIGHT™ 650-10X, 3.75X MS(PEG)$_4$ |
| 20 | DYLIGHT™ 650-10X, 5X MS(PEG)$_4$ |
| 21 | DYLIGHT™ 650-10X, 10X MS(PEG)$_4$ |
| 22 | DYLIGHT™ 650-15X, No Spacer |
| 23 | DYLIGHT™ 650-15X, 2.5X NHS Acetate |
| 24 | DYLIGHT™ 650-15X, 5X NHS Acetate |
| 25 | DYLIGHT™ 650-15X, 10X NHS Acetate |
| 26 | DYLIGHT™ 650-15X, 3.75X MS(PEG)$_4$ |
| 27 | DYLIGHT™ 650-15X, 5X MS(PEG)$_4$ |
| 28 | DYLIGHT™ 650-15X, 10X MS(PEG)$_4$ |
| 29 | DYLIGHT™ 650-20X, No Spacer |
| 30 | DYLIGHT™ 650-20X, 2.5X NHS Acetate |
| 31 | DYLIGHT™ 650-20X, 5X NHS Acetate |
| 32 | DYLIGHT™ 650-20X, 10X NHS Acetate |
| 33 | DYLIGHT™ 650-20X, 3.75X MS(PEG)$_4$ |
| 34 | DYLIGHT™ 650-20X, 5X MS(PEG)$_4$ |
| 35 | DYLIGHT™ 650-20X, 10X MS(PEG)$_4$ |

Figure 7:
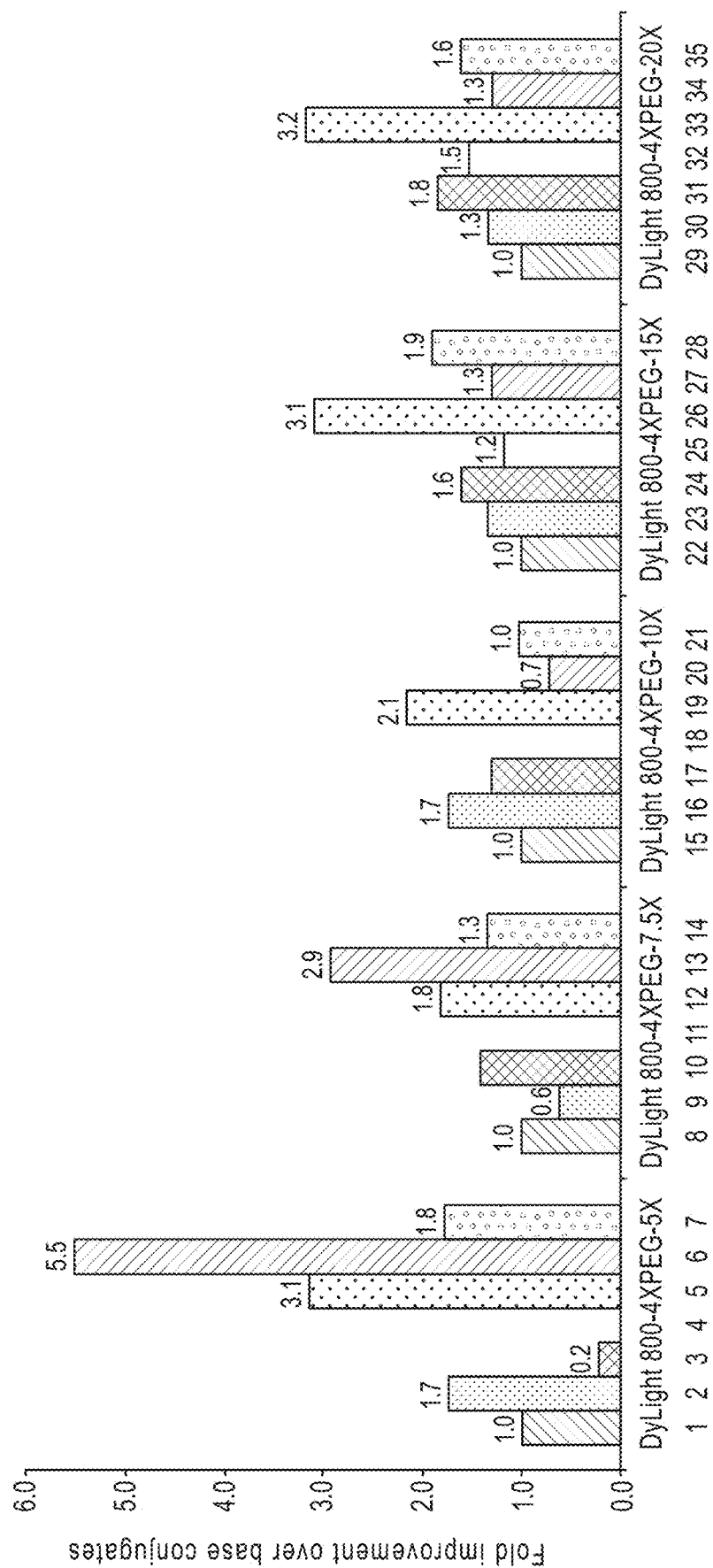

FIG. 7: Dot Blot—Fold improvement of DyLight™ 880-4XPEG conjugates from NHS Acetate (2.5×, 5× and 10×) or MS(PEG)$_4$ (3.75×, 5×, 10×) over base conjugates at each molar excess. This figure demonstrates the effect of the addition of NHS Acetate (2.5× , 5× and 10×) or MS(PEG)$_4$ (3.75×, 5×, 10×) on the detectable fluorescence level of GAM-DyLight™ 800-4×PEG (abbreviated in Table 3 "DyLight™ 800") in a fluorescent dot blot assay. Mouse IgG was serially diluted 1:2 from 1000 ng/dot. All DyLight™ 800-4×PEG-GAR secondary antibodies were diluted to 1/20,000 of 1 mg/ml stock. This dot blot application shows that the addition of MS(PEG)$_4$ (3.75× and 5×) and NHS Acetate (5×) significantly enhanced the fluorescence intensity and sensitivity of base DyLight™ 800-4×PEG conjugate by 1.5 to 6-fold. Lanes of this figures are as follows:

TABLE 3

| Lane | Dye/Spacer |
|---|---|
| 1 | DYLIGHT™ 800-5X, No Spacer |
| 2 | DYLIGHT™ 800-5X, 2.5X NHS Acetate |
| 3 | DYLIGHT™ 800-5X, 5X NHS Acetate |
| 4 | Blank Well |
| 5 | DYLIGHT™ 800-5X, 3.75X MS(PEG)$_4$ |
| 6 | DYLIGHT™ 800-5X, 5X MS(PEG)$_4$ |
| 7 | DYLIGHT™ 800-5X, 10X MS(PEG)$_4$ |
| 8 | DYLIGHT™ 800-7.5X, No Spacer |
| 9 | DYLIGHT™ 800-7.5X, 2.5X NHS Acetate |
| 10 | DYLIGHT™ 800-7.5X, 5X NHS Acetate |
| 11 | Blank Well |
| 12 | DYLIGHT™ 800-7.5X, 3.75X MS(PEG)$_4$ |
| 13 | DYLIGHT™ 800-7.5X, 5X MS(PEG)$_4$ |
| 14 | DYLIGHT™ 800-7.5X, 10X MS(PEG)$_4$ |
| 15 | DYLIGHT™ 800-10X, No Spacer |
| 16 | DYLIGHT™ 800-10X, 2.5X NHS Acetate |
| 17 | DYLIGHT™ 800-10X, 5X NHS Acetate |
| 18 | Blank Well |
| 19 | DYLIGHT™ 800-10X, 3.75X MS(PEG)$_4$ |
| 20 | DYLIGHT™ 800-10X, 5X MS(PEG)$_4$ |
| 21 | DYLIGHT™ 800-10X, 10X MS(PEG)$_4$ |
| 22 | DYLIGHT™ 800-15X, No Spacer |
| 23 | DYLIGHT™ 800-15X, 2.5X NHS Acetate |
| 24 | DYLIGHT™ 800-15X, 5X NHS Acetate |
| 25 | DYLIGHT™ 800-15X, 10X NHS Acetate |
| 26 | DYLIGHT™ 800-15X, 3.75X MS(PEG)$_4$ |
| 27 | DYLIGHT™ 800-15X, 5X MS(PEG)$_4$ |
| 28 | DYLIGHT™ 800-15X, 10X MS(PEG)$_4$ |
| 29 | DYLIGHT™ 800-20X, No Spacer |
| 30 | DYLIGHT™ 800-20X, 2.5X NHS Acetate |
| 31 | DYLIGHT™ 800-20X, 5X NHS Acetate |
| 32 | DYLIGHT™ 800-20X, 10X NHS Acetate |
| 33 | DYLIGHT™ 800-20X, 3.75X MS(PEG)$_4$ |
| 34 | DYLIGHT™ 800-20X, 5X MS(PEG)$_4$ |
| 35 | DYLIGHT™ 800-20X, 10X MS(PEG)$_4$ |

Figure 8:
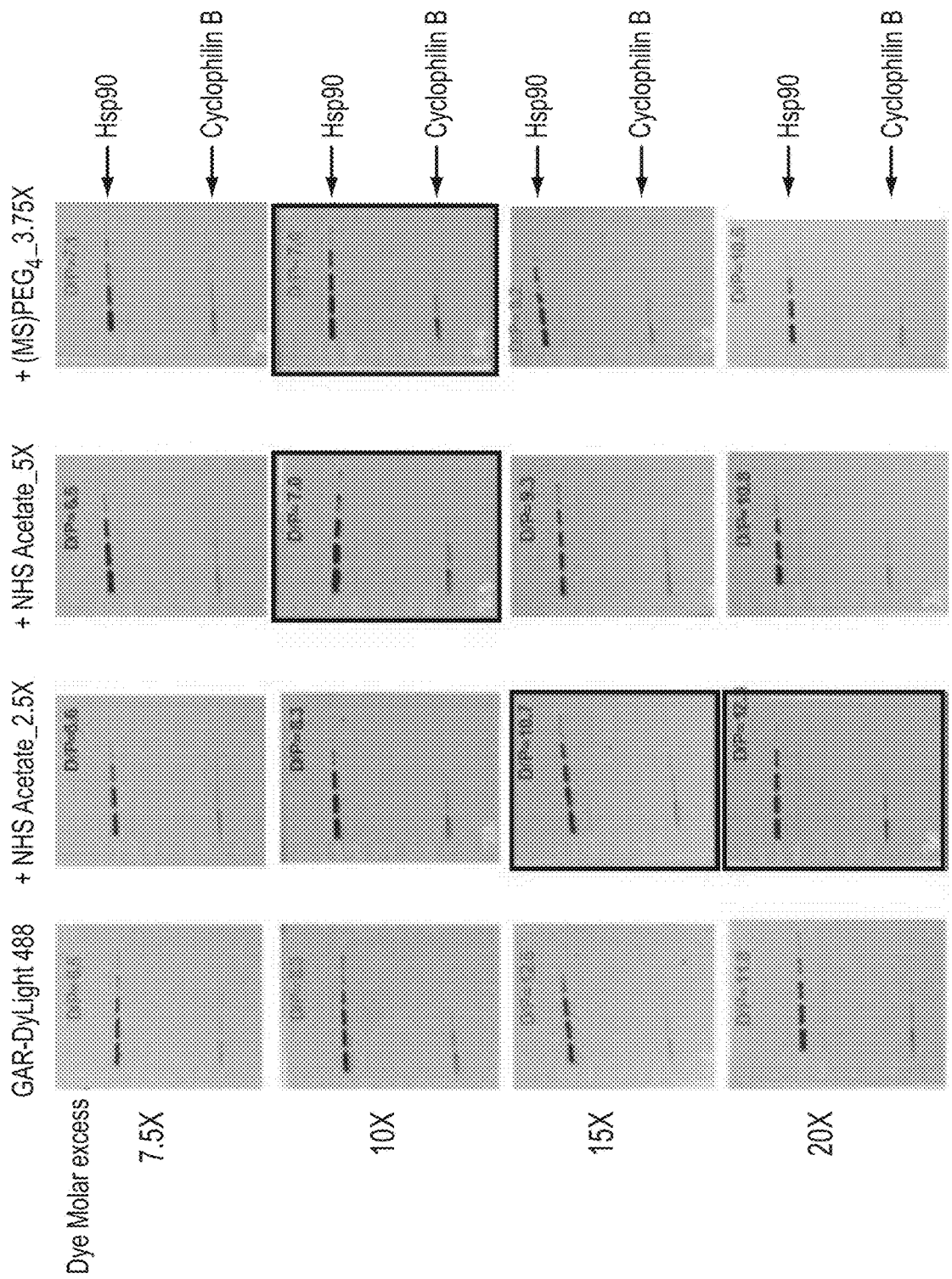

FIG. 8 Western blot assay demonstrating the effect of the addition of NHS Acetate (at 2.5×, 5× and 10× molar excess) or MS(PEG)$_4$ (at 3.75× molar excess) on the fluorescence detection level of GAR-DyLight™ 488 conjugated to the antibody at molar excesses ranging from 5× to 20× of dye.

A431 cell lysate was diluted 3-fold from 1 µg/well. The rabbit primary antibodies used were anti-Hsp90 diluted 1/5000 from 1 mg/ml and anti-Cyclophilin B diluted 1/5000 from 1 mg/ml. All DyLight™ secondary antibodies were diluted 1/5000 from 1 mg/ml stock. These results show that In a Western blot application, there is noticeable increase of fluorescent intensity over the base conjugate (made without the spacer) at each dye molar excess from 7.5× to 20× for DyLight™ 488-GAR conjugated with the addition of NHS Acetate or MS(PEG)$_4$.

Figure 9:
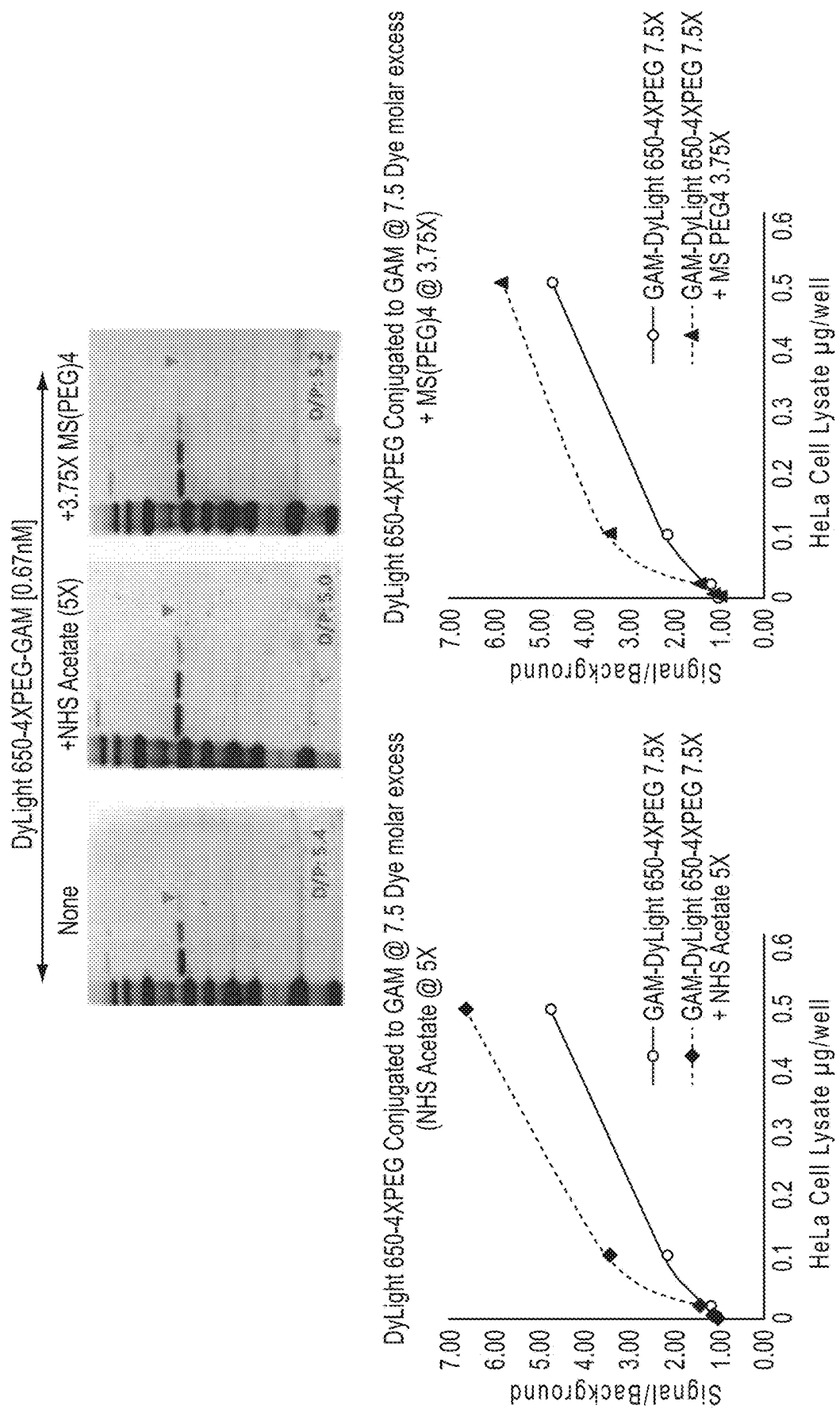

FIG. 9 shows the effect of NHS Acetate (5×) or MS(PEG)$_4$ (5×)) on GAM-DyLight™ 650-4×PEG-GAR (at 7.5× molar excess of dye) in a Western Blot. HeLa cell lysate was diluted 4-fold from 0.5 µg/well. Primary antibody mouse anti-PDI was diluted to 1/5000 of 1 mg/ml. All DyLight™ secondary antibodies were diluted to 1/5000 of 1 mg/ml stock. NHS acetate added at 5× molar excess to GAM-DyLight™ 650-4×PEG-7.5× conjugation improved intensity by 1.5-fold. NHS acetate added at 3.75× molar excess to GAM-DyLight™ 650-4×PEG-7.5× conjugation improved intensity by 1.4-fold.

Figure 10:
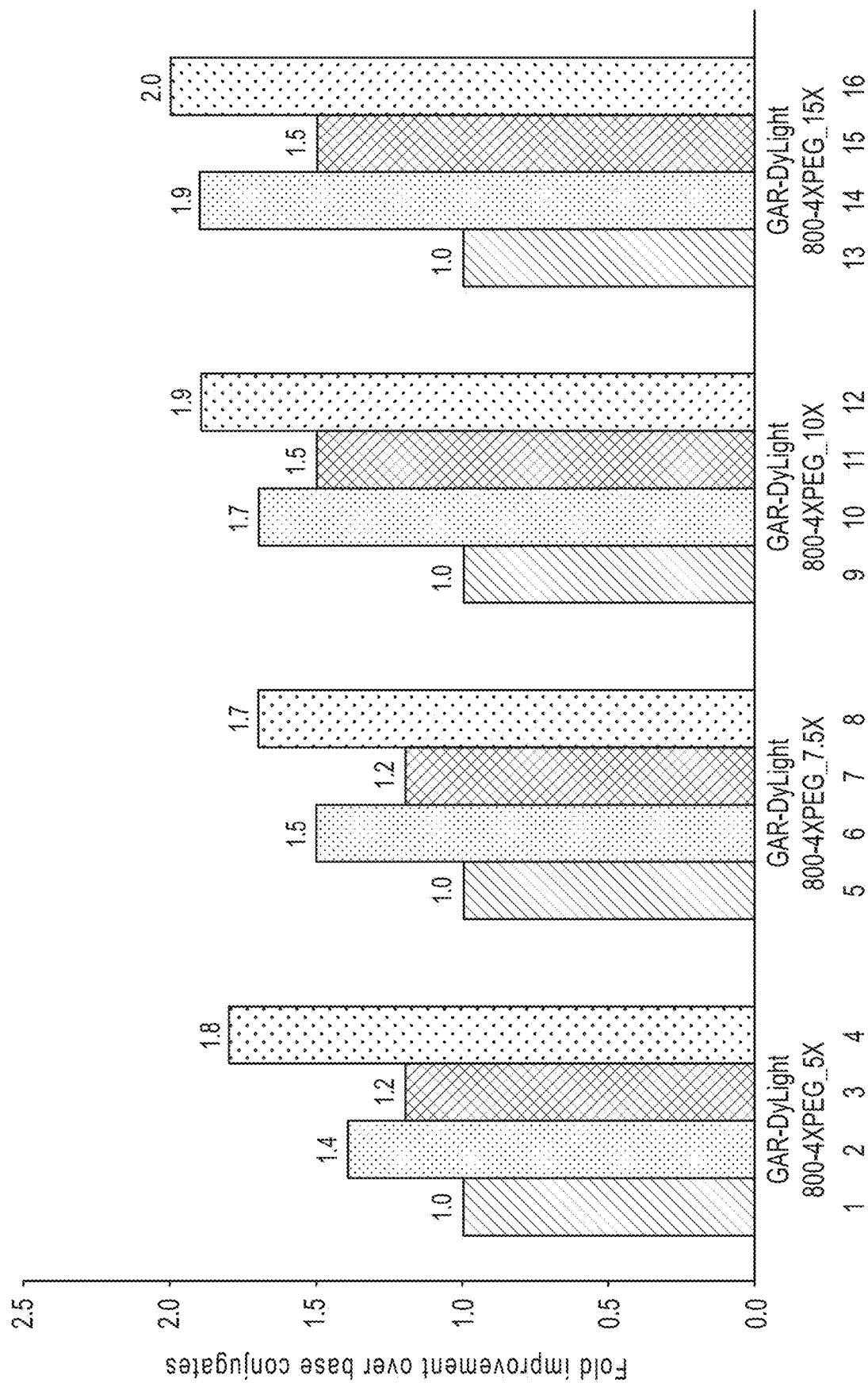

FIG. 10 shows results from a Western blot assay testing the effect of NHS Acetate (2.5×, 5×) or MS(PEG)$_4$ on the detectable fluorescence level of GAR-DyLight™ 800-4× PEG (abbreviated in Table 4 "DyLight™ 800"). A431 cell lysate was serially diluted 1:1. Primary antibodies rabbit anti-Hsp90 and anti-Cyclophilin B were both diluted 1/5000. All DyLight™ secondary antibodies were diluted to 1/20,000 of 1 mg/ml stock. The addition of MS(PEG)$_4$ (3.75× and 5×) and NHS Acetate (2.5-5×) significantly enhanced the fluorescence intensity and sensitivity of base DyLight™ 800-4×PEG conjugate by 20-100% at different molar excesses of the dye in this Western blotting application. Lanes of this figures are as follows:

TABLE 4

| Lane | Dye/Spacer |
| --- | --- |
| 1 | DYLIGHT ™ 800-5x No Spacer |
| 2 | DYLIGHT ™ 800-5X, 2.5X NHS Acetate |
| 3 | DYLIGHT ™ 800-5X, 5X NHS Acetate |
| 4 | DYLIGHT ™ 800-5X, 5X MS(PEG)$_4$ |
| 5 | DYLIGHT ™ 800-7.5x No Spacer |
| 6 | DYLIGHT ™ 800-7.5X, 2.5X NHS Acetate |
| 7 | DYLIGHT ™ 800-7.5X, 5X NHS Acetate |
| 8 | DYLIGHT ™ 800-7.5X, 5X MS(PEG)$_4$ |
| 9 | DYLIGHT ™ 800-10x No Spacer |
| 10 | DYLIGHT ™ 800-10X, 2.5X NHS Acetate |
| 11 | DYLIGHT ™ 800-10X, 5X NHS Acetate |
| 12 | DYLIGHT ™ 800-10X, 5X MS(PEG)$_4$ |
| 13 | DYLIGHT ™ 800-15x No Spacer |
| 14 | DYLIGHT ™ 800-15X, 2.5X NHS Acetate |
| 15 | DYLIGHT ™ 800-15X, 5X NHS Acetate |
| 16 | DYLIGHT ™ 800-15X, 5X MS(PEG)$_4$ |

Figure 11:
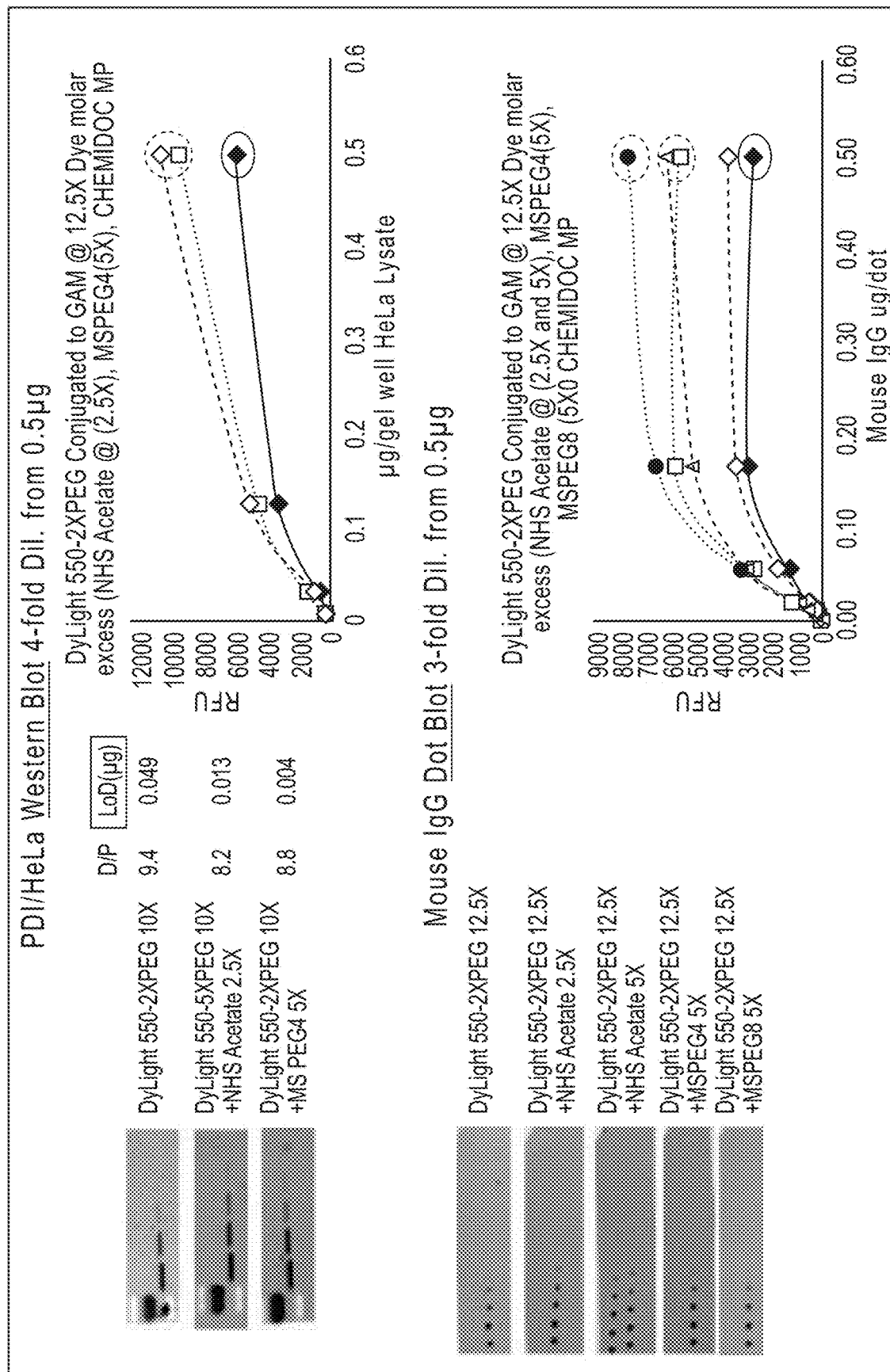

FIG. 11 demonstrates the effect of the addition of NHS Acetate (2.5×, 5× and 10×) or MS(PEG)$_4$ (5×) and MS(PEG)$_8$ (5×) on GAM-DyLight™ 550-2×PEG (at a 12.5× molar excess of dye) in fluorescent Western blot and dot blot assays. HeLa cell lysate was diluted 4-fold from 0.5 µg/well and was stained with anti-PDI primary antibody diluted to 1/5000 of 1 mg/ml. All DyLight™ secondary antibodies were diluted to 1/5000 of 1 mg/ml stock. Western Blotting and Dot Blot assays showed that the addition of MS(PEG)$_4$ (5×) and NHS acetate (2.5× and 5×) significantly enhanced the fluorescence intensity and sensitivity of base DyLight™ 550-2×PEG conjugates by at least by 2-fold. Conjugates prepared with longer chain MS(PEG)$_8$ did not show significant improvement over the base conjugate.

Figure 12:
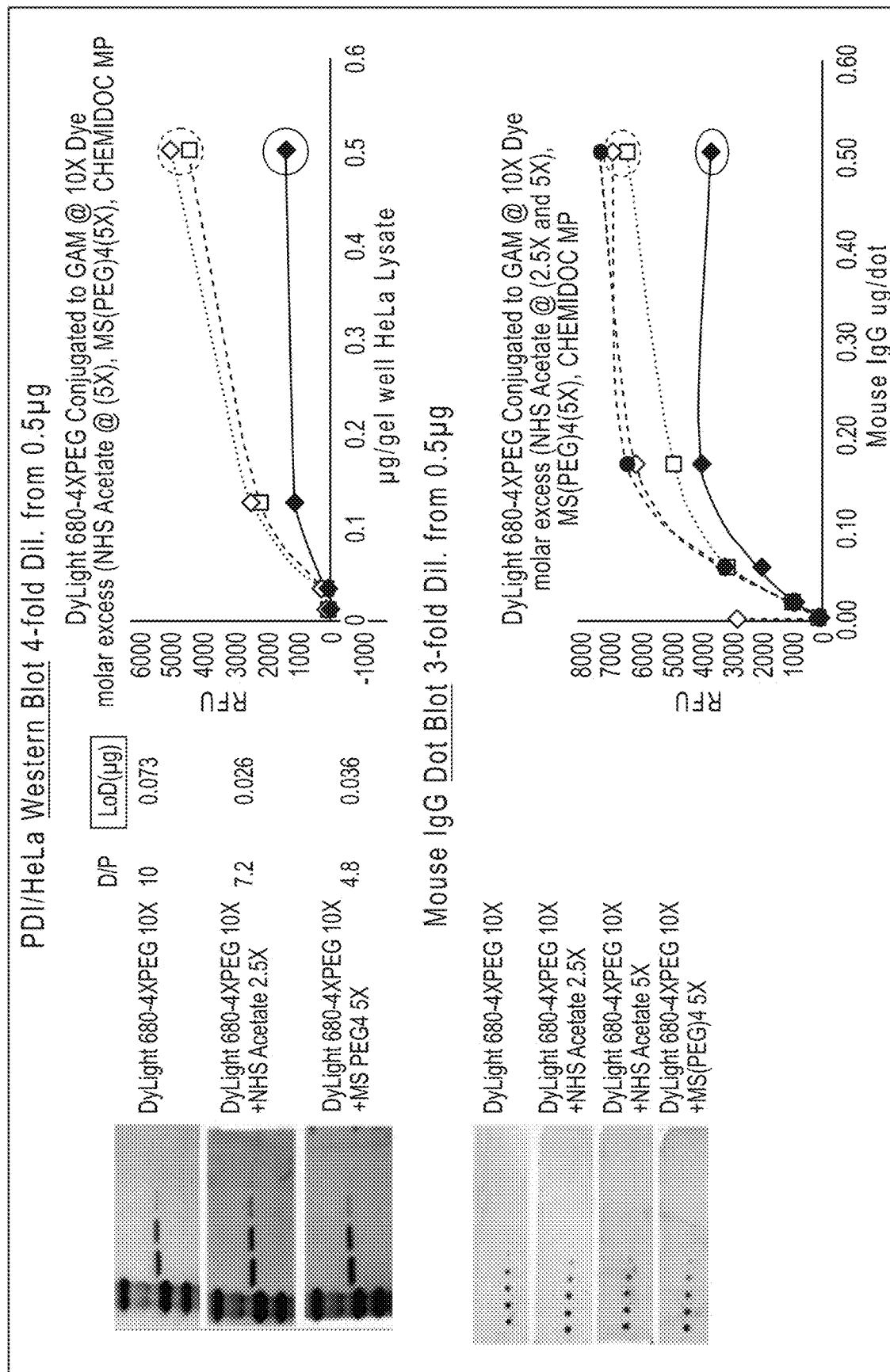

FIG. 12 shows the effect of NHS Acetate (2.5×, 5×) or MS(PEG)$_4$ (5×) on GAM-DyLight™ 680-4×PEG-GAR (at 10× molar excess of dye) in Western blot and dot blot assays. For Western blotting, HeLa cell lysate was diluted 4-fold from 0.5 µg/well and anti-PDI primary antibody was diluted to 1/5000 of 1 mg/ml. For dot blotting, mouse IgG was serially diluted 1:2 from 1000 ng/dot. All DyLight™ 680-4×PEG-GAR secondary antibodies were diluted to 1/20000 of 1 mg/ml stock. Both Western Blots and Dot Blots show that the addition of MS(PEG)$_4$ (5×) and NHS acetate (2.5× and 5×) significantly enhanced the fluorescence intensity and sensitivity of base DyLight™ 680-4×PEG conjugate by 3 to 4-fold.

Figure 13A:
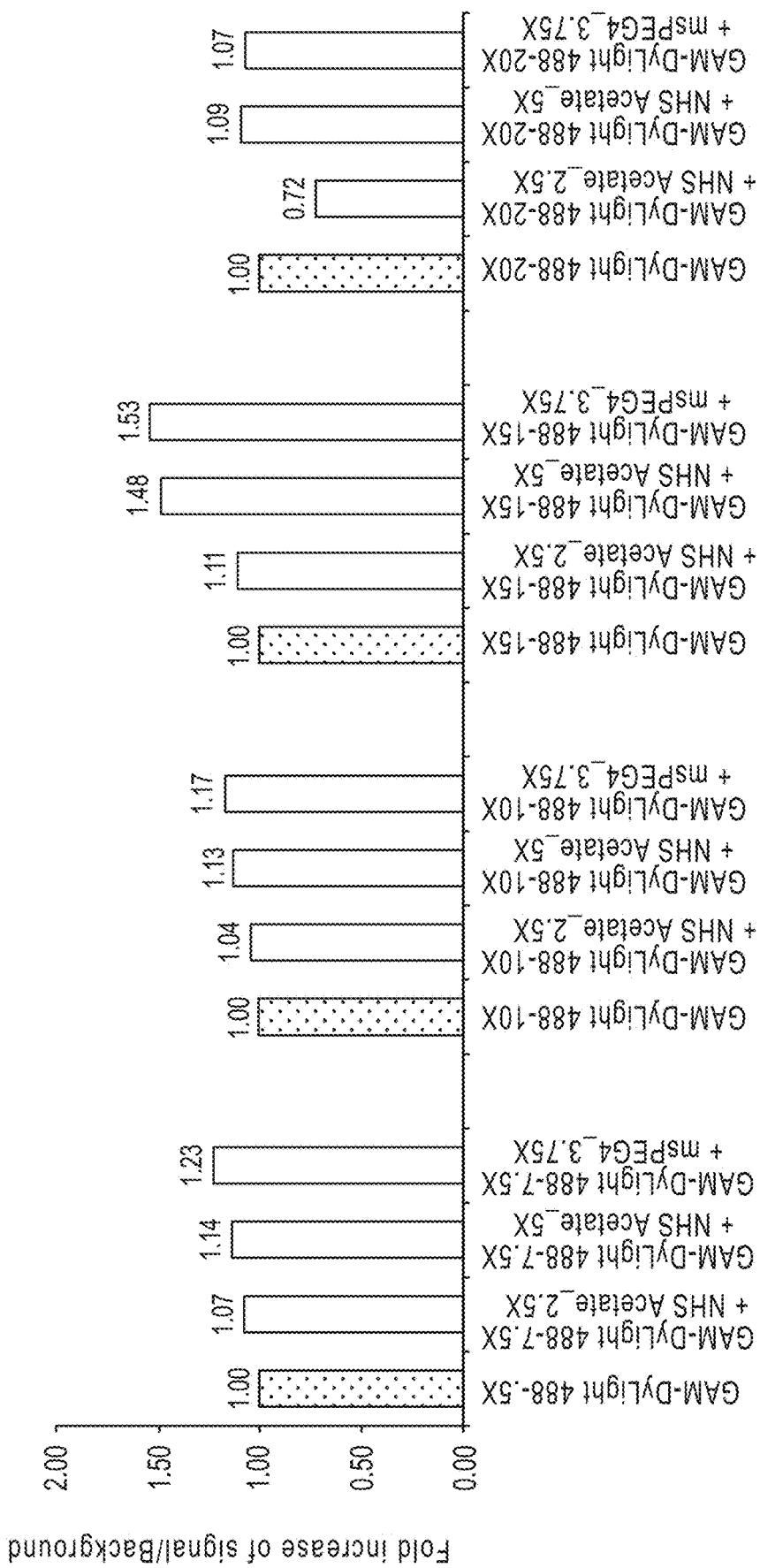
Figure 13B:
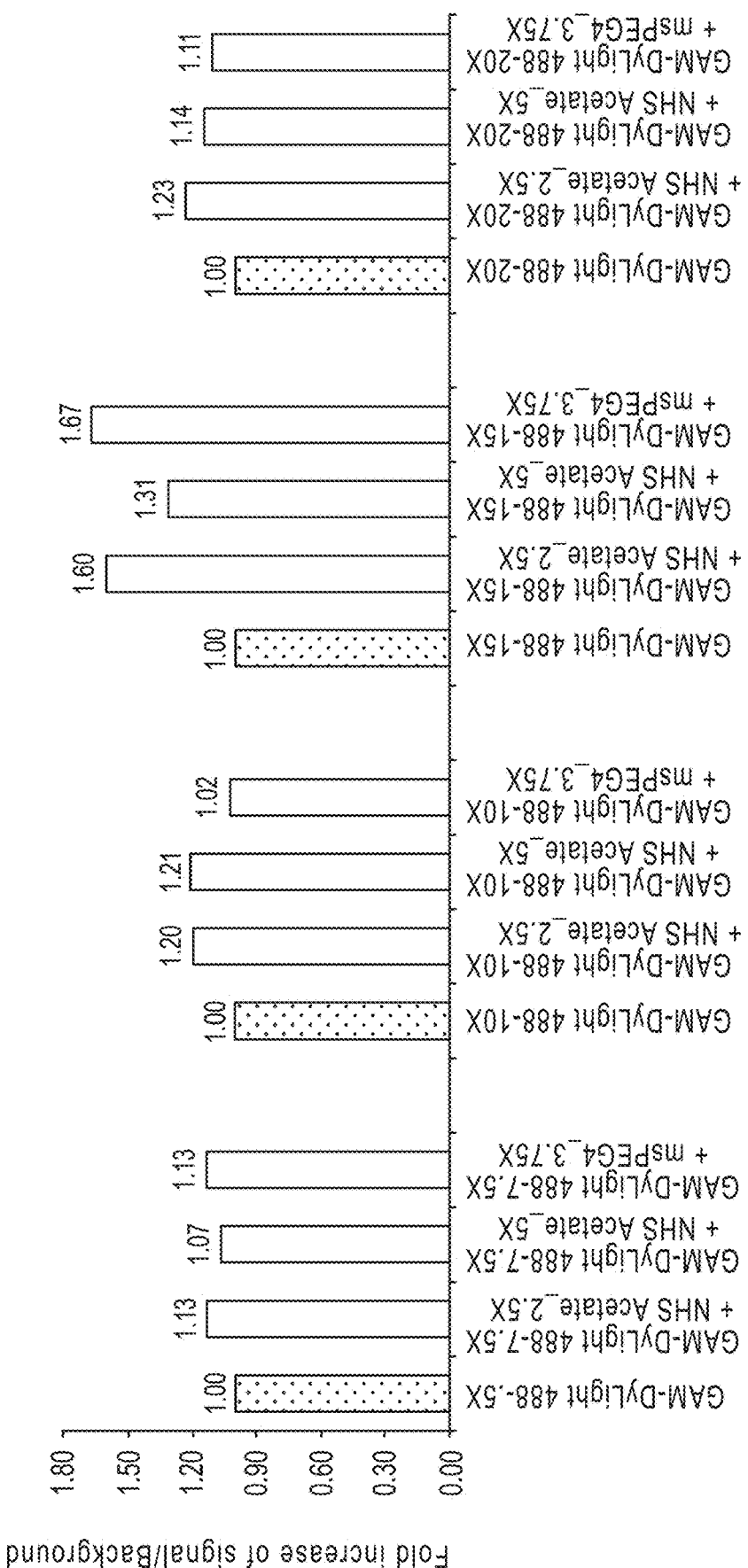

FIG. 13A (IFC with DyLight™ 488-GAM 4 µg/ml. Signal/background fold improvement from NHS Acetate (2.5×, 5×) or MS(PEG)$_4$ (3.75×) over base conjugates at various molar excesses) and FIG. 13B (IFC—Detection of PDI with DyLight™ 488-GAR 4 µg/ml. Signal/background fold improvement from NHS Acetate (2.5×, 5×) or MS(PEG)$_4$ (3.75×) over base conjugates at various molar excesses) demonstrates the effect of NHS acetate (2.5× and 5×) or MS(PEG)$_4$(3.75×) addition on fluorescence of GAM-DyLight™ 488 (13A) and GAR-DyLight™ 488 (13B) at 7.5× to 20× molar excess of dye in cellular imaging assays. FIG. 13A: A549 cells were stained with a pH2Ax primary antibody diluted to 1/1000 of the 1 mg/ml stock. All DyLight™ 488 secondary antibodies were diluted to 1/250 of the 1 mg/ml stock. NHS acetate modified conjugates provided an improvement of signal/background as compared to the base conjugates at 15× dye molar excesses; ranging from 1.4 to 1.5-fold (GAM) and 1.1 to 1.6-fold (GAR). For GAM conjugates the most significant improvement was observed with NHS Acetate at 5× and with MS(PEG)$_4$ at 3.75× for GAR conjugates the more noticeable improvement was observed with NHS Acetate at 2.5× and with MS(PEG)$_4$ at 3.75×. FIG. 13B shows a similar experiment where A549 cells were stained with a pH2Ax primary antibody.

Figure 14:
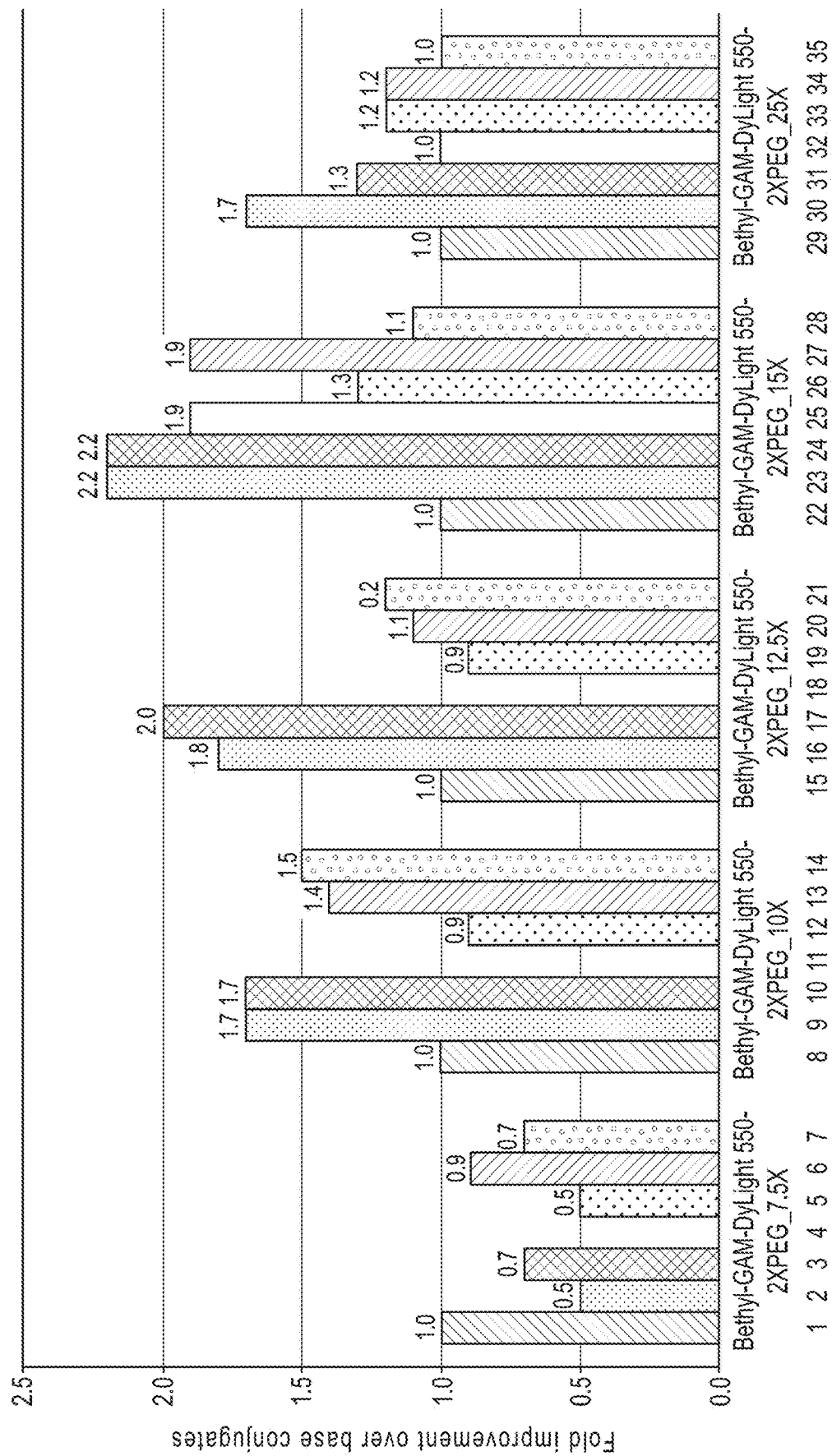

FIG. 14: IFC Detection of PDI with DyLight™ 550-2XPEG (7.5× to 20×) 4 µg/ml. Fold improvement from the addition of NHS Acetate (2.5×, 5× and 10×) or MS(PEG)$_4$ (3.75×, 5×, 10×) over base conjugates at each dye molar excesses. This figure shows the effect of NHS Acetate (2.5×, 5× and 10×) or MS(PEG)$_4$ (3.75×, 5× and 10×) addition to GAM-DyLight™ 550-2XPEG-GAM (at 7.5× to 20× molar excess of dye) on fluorescence cellular imaging assays. U2OS cells were stained with an anti-PDI primary antibody diluted to 1/100 of the 1 mg/ml stock. All DyLight™ 550-2xPEG-GAM secondary antibodies (abbreviated in Table 5 "DyLight™ 550") were diluted to 1/250 of the 1 mg/ml stock. In this cellular imaging application, the addition of 5×NHS Acetate generated about 50% improvement as compared to the base conjugate (made without the additives) for DYLIGHT™ 550-2×PEG GAM conjugate at 12.5× dye molar excess, and addition of 3.75× MS(PEG)$_4$ resulted in about 50% improvement over the base conjugates at 20× dye molar excess. Lanes of this figures are as follows:

TABLE 5

| Lane | Dye/Spacer |
| --- | --- |
| 1 | DYLIGHT ™ 550-7.5X, No Spacer |
| 2 | DYLIGHT ™ 550-7.5X, 2.5X NHS Acetate |
| 3 | DYLIGHT ™ 550-7.5X, 5X NHS Acetate |
| 4 | Blank |
| 5 | DYLIGHT ™ 550-7.5X, 3.75X MS(PEG)$_4$ |
| 6 | DYLIGHT ™ 550-7.5X, 5X MS(PEG)$_4$ |
| 7 | DYLIGHT ™ 550-7.5X, 10X MS(PEG)$_4$ |
| 8 | DYLIGHT ™ 550-10X, No Spacer |
| 9 | DYLIGHT ™ 550-10X, 2.5X NHS Acetate |
| 10 | DYLIGHT ™ 550-10X, 5X NHS Acetate |
| 11 | Blank |
| 12 | DYLIGHT ™ 550-10X, 3.75X MS(PEG)$_4$ |
| 13 | DYLIGHT ™ 550-10X, 5X MS(PEG)$_4$ |
| 14 | DYLIGHT ™ 550-10X, 10X MS(PEG)$_4$ |
| 15 | DYLIGHT ™ 550-12.5X, No Spacer |
| 16 | DYLIGHT ™ 550-12.5X, 2.5X NHS Acetate |
| 17 | DYLIGHT ™ 550-12.5X, 5X NHS Acetate |
| 18 | Blank |
| 19 | DYLIGHT ™ 550-12.5X, 3.75X MS(PEG)$_4$ |
| 20 | DYLIGHT ™ 550-12.5X, 5X MS(PEG)$_4$ |
| 21 | DYLIGHT ™ 550-12.5X, 10X MS(PEG)$_4$ |
| 22 | DYLIGHT ™ 550-15X, No Spacer |
| 23 | DYLIGHT ™ 550-15X, 2.5X NHS Acetate |
| 24 | DYLIGHT ™ 550-15X, 5X NHS Acetate |
| 25 | DYLIGHT ™ 550-15X, 10X NHS Acetate |
| 26 | DYLIGHT ™ 550-15X, 3.75X MS(PEG)$_4$ |
| 27 | DYLIGHT ™ 550-15X, 5X MS(PEG)$_4$ |
| 28 | DYLIGHT ™ 550-15X, 10X MS(PEG)$_4$ |
| 29 | DYLIGHT ™ 550-25X, No Spacer |
| 30 | DYLIGHT ™ 550-20X, 2.5X NHS Acetate |
| 31 | DYLIGHT ™ 550-20X, 5X NHS Acetate |
| 32 | DYLIGHT ™ 550-20X, 10X NHS Acetate |
| 33 | DYLIGHT ™ 550-20X, 3.75X MS(PEG)$_4$ |
| 34 | DYLIGHT ™ 550-20X, 5X MS(PEG)$_4$ |
| 35 | DYLIGHT ™ 550-20X, 10X MS(PEG)$_4$ |

Figure 15:
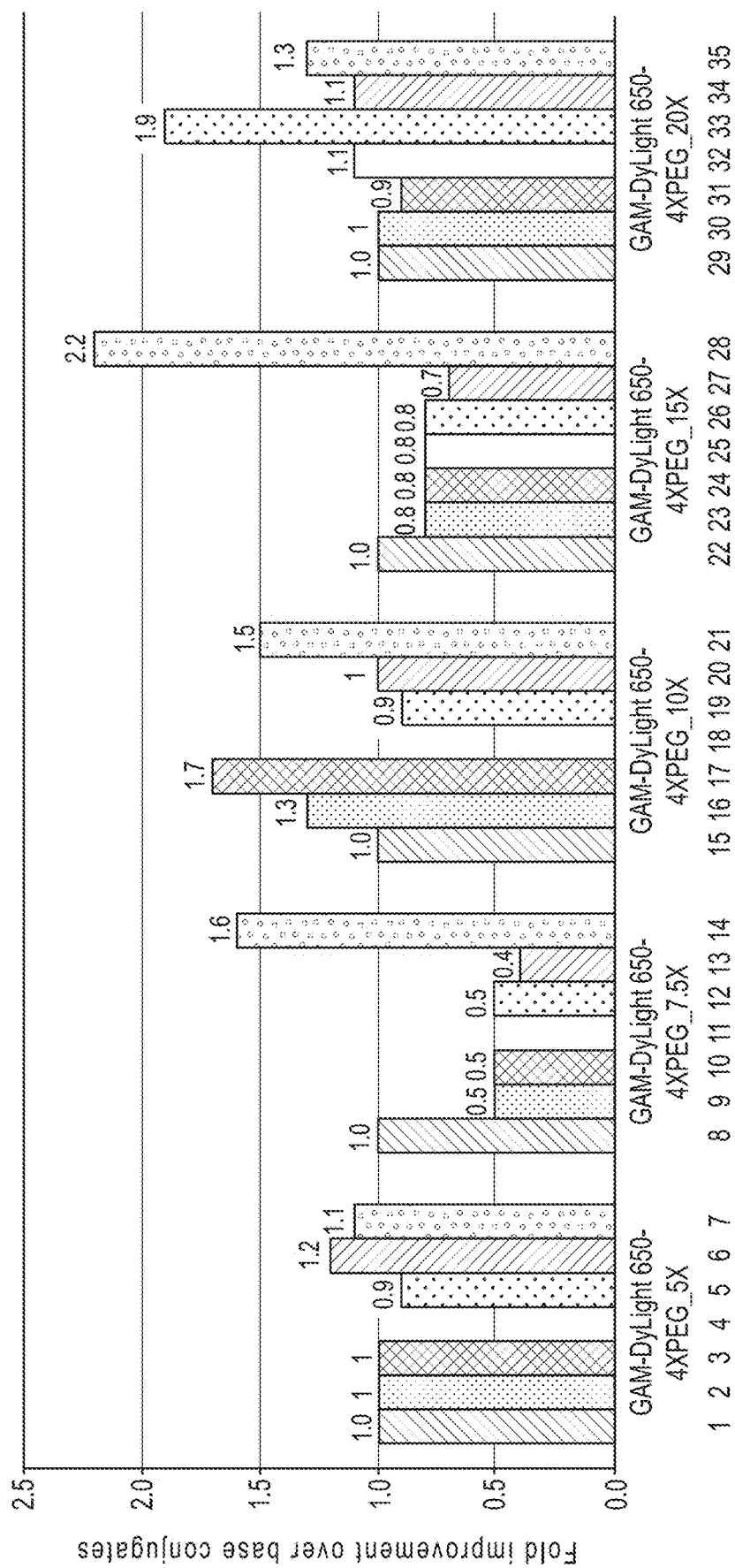

FIG. 15: IFC Detection of PDI with DYLIGHT™ 650-4XPEG (7.5× to 20×) 4 µg/ml. Fold improvement from the addition of NHS Acetate (2.5×, 5× and 10×) or MS(PEG)$_4$ (3.75×, 5×, 10×) over base conjugates at each dye molar excesses This figure shows effect of adding NHS Acetate (2.5×, 5× and 10×) or MS(PEG)$_4$ (3.75×, 5×, 10×) on GAM-DYLIGHT™ 650-4×PEG in a fluorescence cellular imaging assay GAM-DYLIGHT™ 650-4×PEG). U2OS cells were stained with anti-PDI primary antibody diluted to 1/100 of 1 mg/ml stock. All DYLIGHT™ 650-4×PEG-GAM secondary antibodies (abbreviated in Table 6 "DYLIGHT™ 650") were diluted to 1/250 of 1 mg/ml stock. In this application, the addition of NHS Acetate-5× generated about 70% improvement as compared to the base conjugate (made without the additives) for DYLIGHT™ 650-4×PEG-GAM conjugate at 20× molar excess, and MS(PEG)$_4$-3.75× showed about 90% improvement over the base conjugates at 20× molar excess. Lanes of this figures are as follows:

TABLE 6

| Lane | Dye/Spacer |
| --- | --- |
| 1 | DYLIGHT ™ 650-5X, No Spacer |
| 2 | DYLIGHT ™ 650-5X, 2.5X NHS Acetate |
| 3 | DYLIGHT ™ 650-5X, 5X NHS Acetate |
| 4 | Blank |
| 5 | DYLIGHT ™ 650-5X, 3.75X MS(PEG)$_4$ |
| 6 | DYLIGHT ™ 650-5X, 5X MS(PEG)$_4$ |
| 7 | DYLIGHT ™ 650-5X, 10X MS(PEG)$_4$ |
| 8 | DYLIGHT ™ 650-7.5X, No Spacer |
| 9 | DYLIGHT ™ 650-7.5X, 2.5X NHS Acetate |
| 10 | DYLIGHT ™ 650-7.5X, 5X NHS Acetate |
| 11 | Blank |
| 12 | DYLIGHT ™ 650-7.5X, 3.75X MS(PEG)$_4$ |
| 13 | DYLIGHT ™ 650-7.5X, 5X MS(PEG)$_4$ |
| 14 | DYLIGHT ™ 650-7.5X, 10X MS(PEG)$_4$ |
| 15 | DYLIGHT ™ 650-10X, No Spacer |
| 16 | DYLIGHT ™ 650-10X, 2.5X NHS Acetate |
| 17 | DYLIGHT ™ 650-10X, 5X NHS Acetate |
| 18 | Blank |
| 19 | DYLIGHT ™ 650-10X, 3.75X MS(PEG)$_4$ |
| 20 | DYLIGHT ™ 650-10X, 5X MS(PEG)$_4$ |
| 21 | DYLIGHT ™ 650-10X, 10X MS(PEG)$_4$ |
| 22 | DYLIGHT ™ 650-15X, No Spacer |
| 23 | DYLIGHT ™ 650-15X, 2.5X NHS Acetate |
| 24 | DYLIGHT ™ 650-15X, 5X NHS Acetate |
| 25 | DYLIGHT ™ 650-15X, 10X NHS Acetate |
| 26 | DYLIGHT ™ 650-15X, 3.75X MS(PEG)$_4$ |
| 27 | DYLIGHT ™ 650-15X, 5X MS(PEG)$_4$ |
| 28 | DYLIGHT ™ 650-15X, 10X MS(PEG)$_4$ |
| 29 | DYLIGHT ™ 650-20X, No Spacer |
| 30 | DYLIGHT ™ 650-20X, 2.5X NHS Acetate |

TABLE 6-continued

| Lane | Dye/Spacer |
|---|---|
| 31 | DYLIGHT™ 650-20X, 5X NHS Acetate |
| 32 | DYLIGHT™ 650-20X, 10X NHS Acetate |
| 33 | DYLIGHT™ 650-20X, 3.75X MS(PEG)$_4$ |
| 34 | DYLIGHT™ 650-20X, 5X MS(PEG)$_4$ |
| 35 | DYLIGHT™ 650-20X, 10X MS(PEG)$_4$ |

Figure 16:
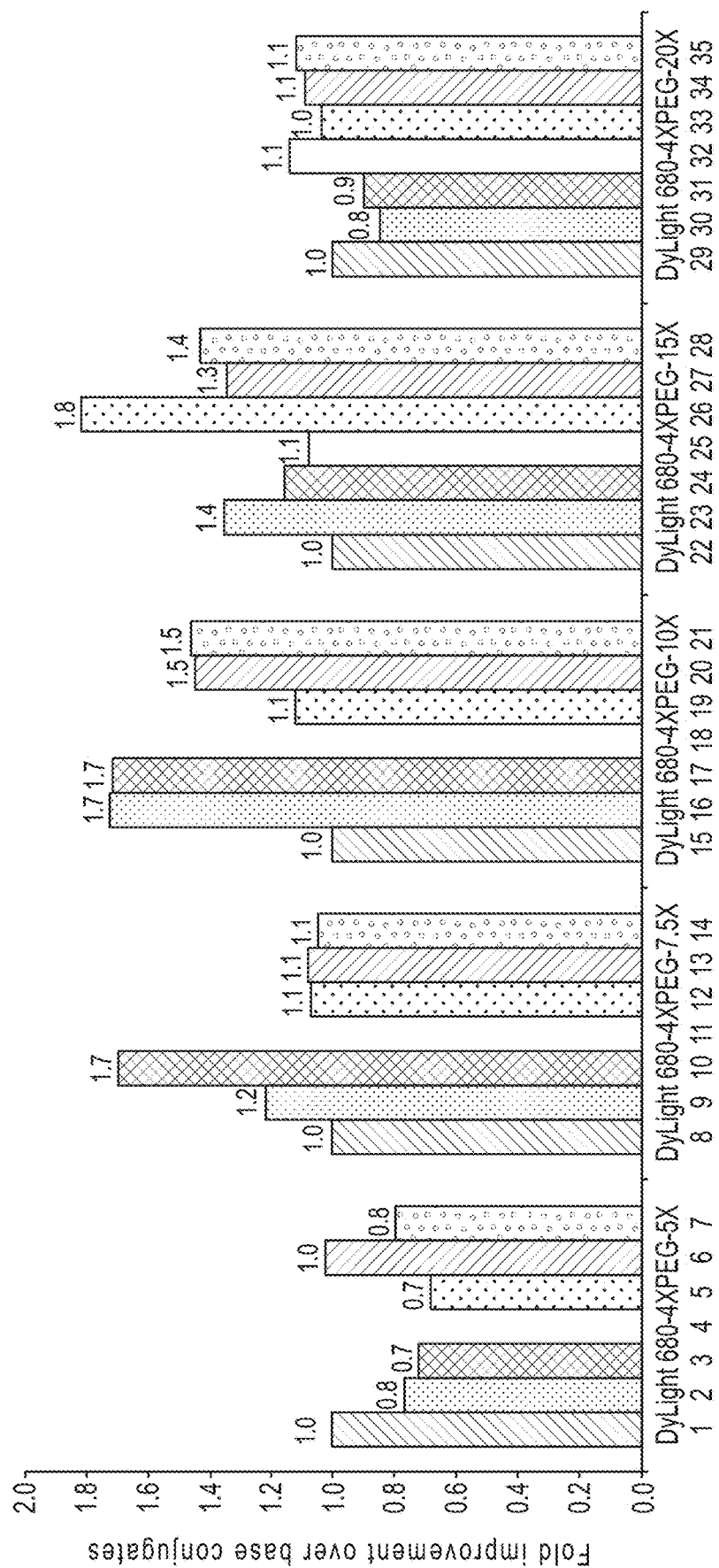

FIG. 16: IFC—DYLIGHT™ 680-4XPEG Fold improvement from NHS Acetate (2.5×, 5× and 10×) or MS(PEG)$_4$ (3.75×, 5×, 10×) over base conjugates at each molar excess. This figure shows the effect of the addition of NHS Acetate (2.5×, 5× and 10×) or MS(PEG)$_4$ (3.3.75×, 5×, 10×) on GAM-DYLIGHT™ 680-4×PEG) in a cellular imaging assay. U2OS cells were stained with mouse anti-PDI primary antibody diluted to 1/100 of 1 mg/ml stock. All DYLIGHT™ 680-4×PEG-GAM secondary antibodies (abbreviated in Table 7 "DYLIGHT™ 680") were diluted to 1/250 of 1 mg/ml stock: In this cellular imaging application, the addition of NHS Acetate-5× generated about 70% improvement for dyes conjugates at both 7.5× and 10× as compared to the base conjugate (made without the additives) for DYLIGHT™ 680-4×PEG. GAM conjugate at molar excesses of 15× molar excess and MS(PEG)$_4$-3.75× showed about 80% improvement over the base conjugates at 15× molar excesses. Lanes of this figures are as follows:

TABLE 7

| Lane | Dye/Spacer |
|---|---|
| 1 | DYLIGHT™ 680-5X, No Spacer |
| 2 | DYLIGHT™ 680-5X, 2.5X NHS Acetate |
| 3 | DYLIGHT™ 680-5X, 5X NHS Acetate |
| 4 | Blank |
| 5 | DYLIGHT™ 680-5X, 3.75X MS(PEG)$_4$ |
| 6 | DYLIGHT™ 680-5X, 5X MS(PEG)$_4$ |
| 7 | DYLIGHT™ 680-5X, 10X MS(PEG)$_4$ |
| 8 | DYLIGHT™ 680-7.5X, No Spacer |
| 9 | DYLIGHT™ 680-7.5X, 2.5X NHS Acetate |
| 10 | DYLIGHT™ 680-7.5X, 5X NHS Acetate |
| 11 | Blank |
| 12 | DYLIGHT™ 680-7.5X, 3.75X MS(PEG)$_4$ |
| 13 | DYLIGHT™ 680-7.5X, 5X MS(PEG)$_4$ |
| 14 | DYLIGHT™ 680-7.5X, 10X MS(PEG)$_4$ |
| 15 | DYLIGHT™ 680-10X, No Spacer |
| 16 | DYLIGHT™ 680-10X, 2.5X NHS Acetate |
| 17 | DYLIGHT™ 680-10X, 5X NHS Acetate |
| 18 | Blank |
| 19 | DYLIGHT™ 680-10X, 3.75X MS(PEG)$_4$ |
| 20 | DYLIGHT™ 680-10X, 5X MS(PEG)$_4$ |

TABLE 7-continued

| Lane | Dye/Spacer |
|---|---|
| 21 | DYLIGHT™ 680-10X, 10X MS(PEG)$_4$ |
| 22 | DYLIGHT™ 680-15X, No Spacer |
| 23 | DYLIGHT™ 680-15X, 2.5X NHS Acetate |
| 24 | DYLIGHT™ 680-15X, 5X NHS Acetate |
| 25 | DYLIGHT™ 680-15X, 10X NHS Acetate |
| 26 | DYLIGHT™ 680-15X, 3.75X MS(PEG)$_4$ |
| 27 | DYLIGHT™ 680-15X, 5X MS(PEG)$_4$ |
| 28 | DYLIGHT™ 680-15X, 10X MS(PEG)$_4$ |
| 29 | DYLIGHT™ 680-20X, No Spacer |
| 30 | DYLIGHT™ 680-20X, 2.5X NHS Acetate |
| 31 | DYLIGHT™ 680-20X, 5X NHS Acetate |
| 32 | DYLIGHT™ 680-20X, 10X NHS Acetate |
| 33 | DYLIGHT™ 680-20X, 3.75X MS(PEG)$_4$ |
| 34 | DYLIGHT™ 680-20X, 5X MS(PEG)$_4$ |
| 35 | DYLIGHT™ 680-20X, 10X MS(PEG)$_4$ |

Figure 17:
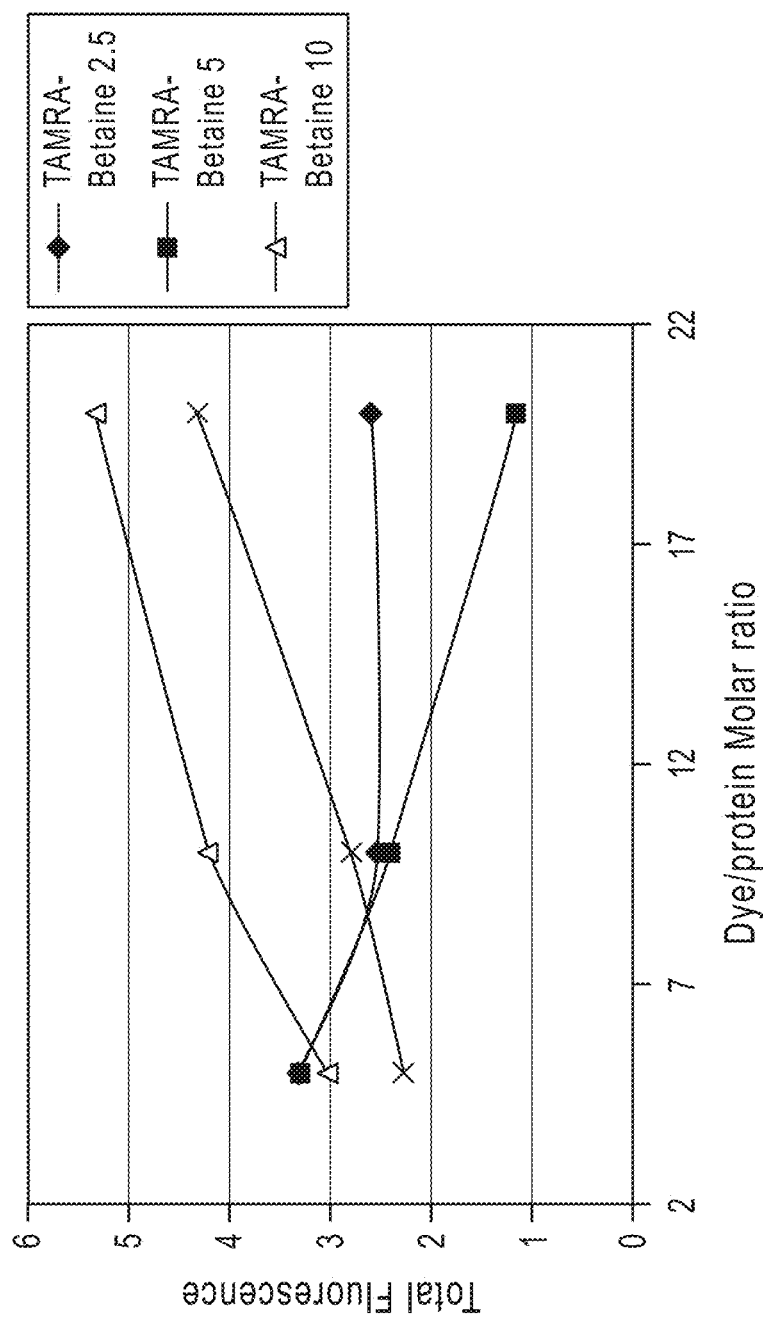

FIG. 17: TAMRA-GAM co-conjugates with or without Betaine This figure exemplifies observed fluorescence levels of TAMRA-goat anti-mouse antibody (GAM) conjugates, with or without betaine, at various dye/protein molar ratios. Levels of betaine were tested at 2.5, 5, and 10× molar excess as compared to moles of antibody. These antibodies labeled with NHS-Rhodamine (TAMRA) and conjugated with a variety of NHS-Betaine concentrations (Betaine 2.5×, Betaine 5×, Betaine 10× molar excess of dye) displayed an increase in total fluorescence when the antibodies were conjugated with Betaine as the spacer agent.

Figure 18:
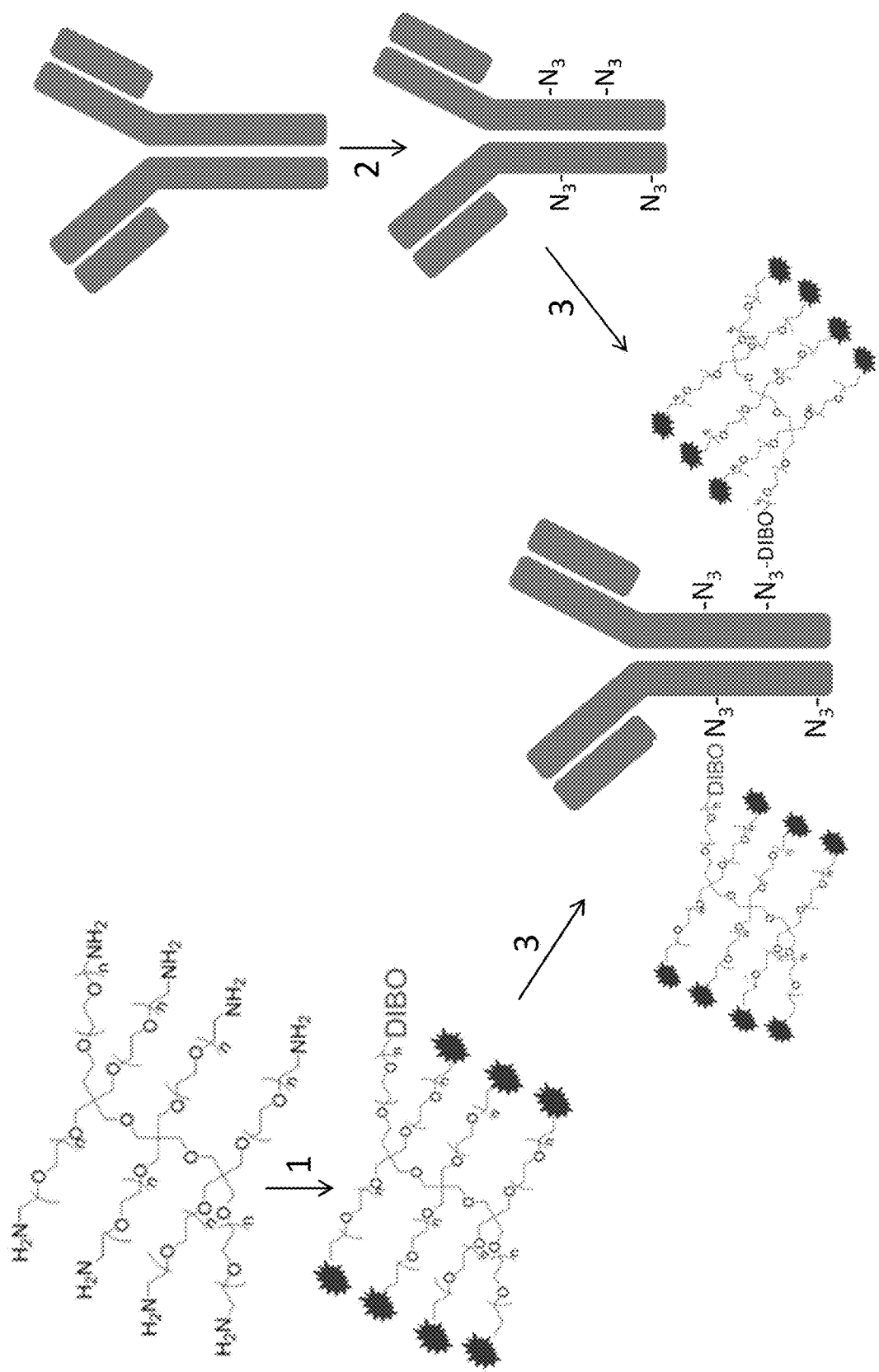

FIG. 18 shows a schematic representation of the generation and attachment of branched PEG molecules containing fluorescent labels to an antibody molecule. In step 1, a reactive group and fluorescent labels are attached to $NH_2$ groups on branched PEG molecules. In step 2, attachment sites are added to the antibody molecule. In step 3, the fluorescently labeled branched PEG molecules are covalently linked to the antibody molecule.

Figure 19:
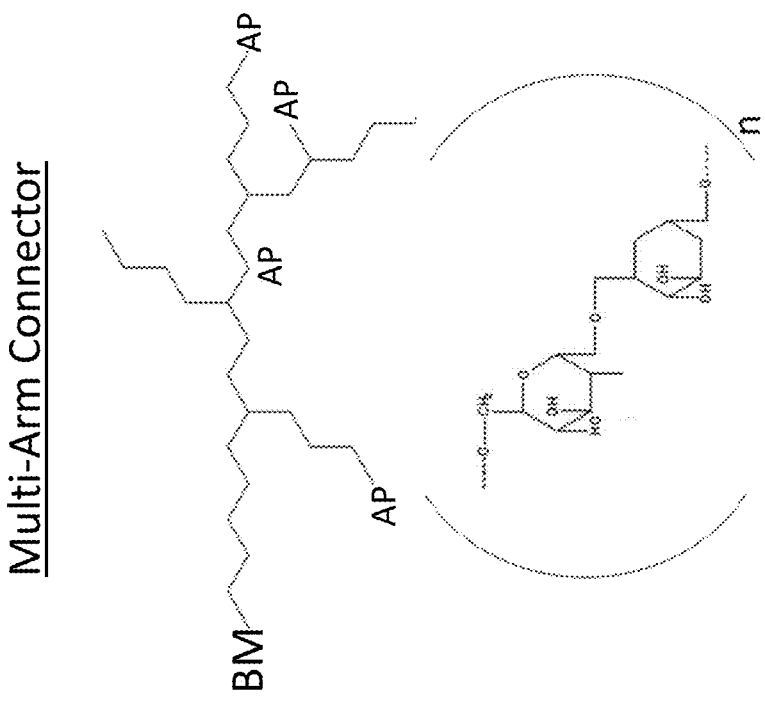
Figure 19:

FIG. 19 is an illustration showing one example each of a single-armed connector (e.g., amylose) and a multi-armed connector (dextran). BM stands for biomolecule and AP stand for attachment point, meaning that a fluorescent label is attached at that point.

Figure 20:
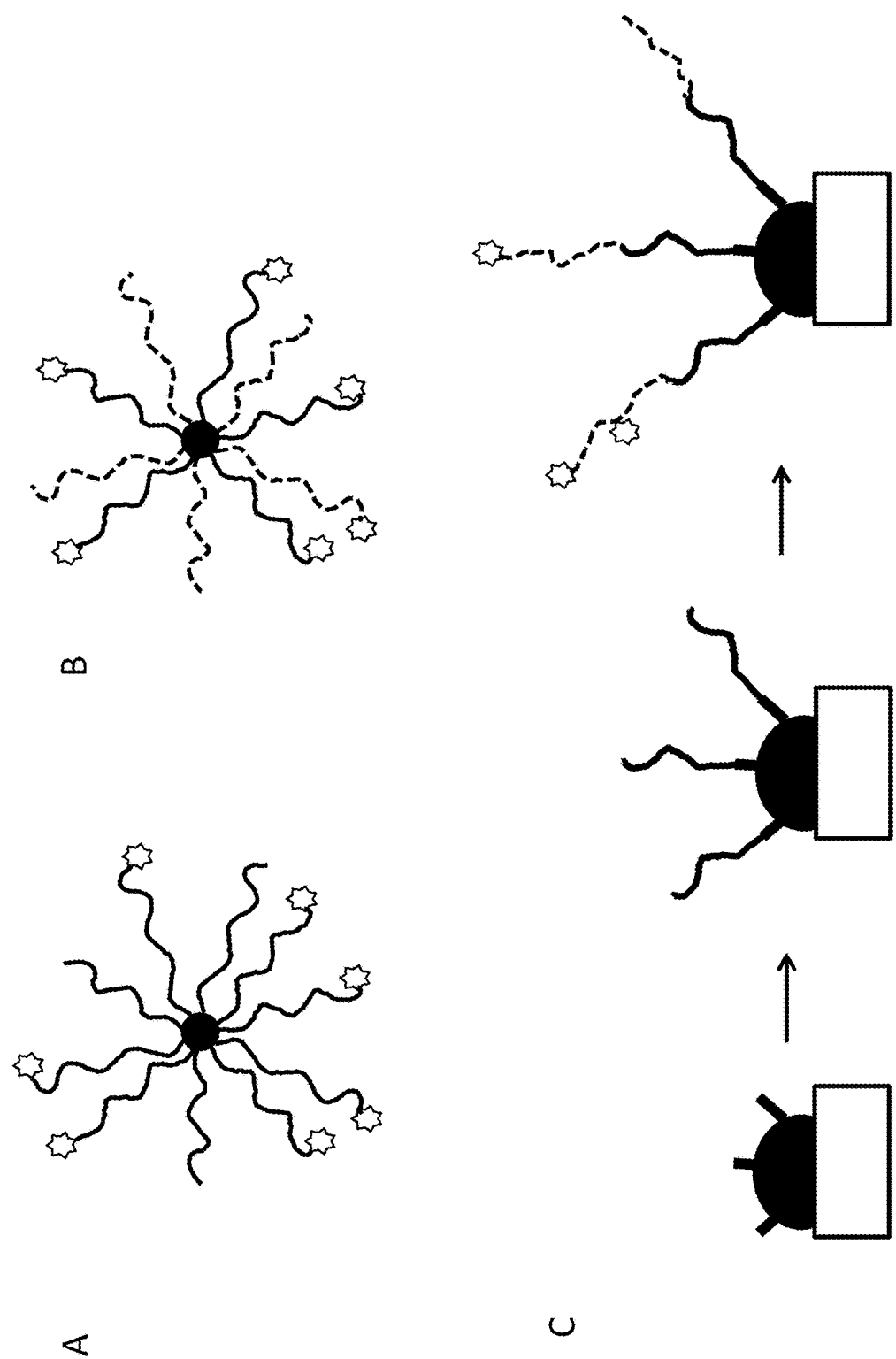

FIG. 20 is an illustration of different types of star polymers and an example of components of some star polymers and an example of how star polymers can be prepared. FIG. 20A is an illustration of a star polymer with a core (the black circle) and multiple of arms (the black lines). The stars represent fluorescent labels covalently linked to the arms. Some of the arms are not fluorescently labeled to indicate that the labeling did not go to completion. FIG. 20B is an illustration of a similar star polymer where the arms are of two different types (e.g., polyethylene glycol and polyvinyl alcohol), the different arm types being represented by the solid and dashed lines. The left side of FIG. 20C shows a partial representation of a core (the black semi-circles) with reactive groups (the grey bars) that can be used to attach other chemical entities or to serve as initiators for polymerization. A core is represented in the center that has adapters (solid black lines) attached to reactive groups. Polymer arms are shown to the right (black dashed lines) attached to the adapters, and labeled with fluorescent molecules (stars)

Figure 21:
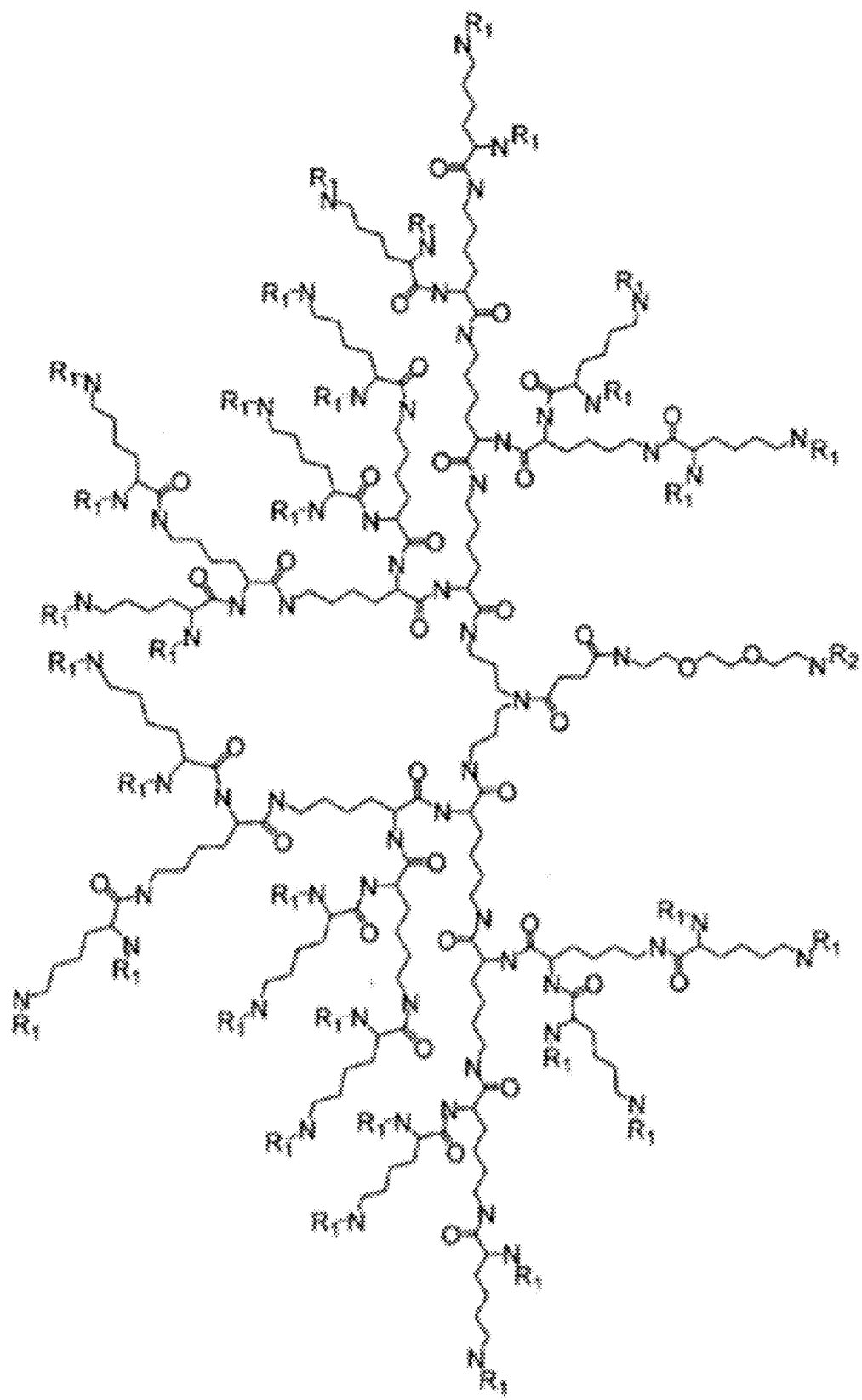

FIG. 21 shows an exemplary polylysine molecule of a type that can be used in the practice of the invention. The $R_1$ and R2 groups are shown as unlabeled. These groups can be used as attachment points for fluorescent labels and for conjugation to biomolecules (e.g., antibodies).

Figure 22:
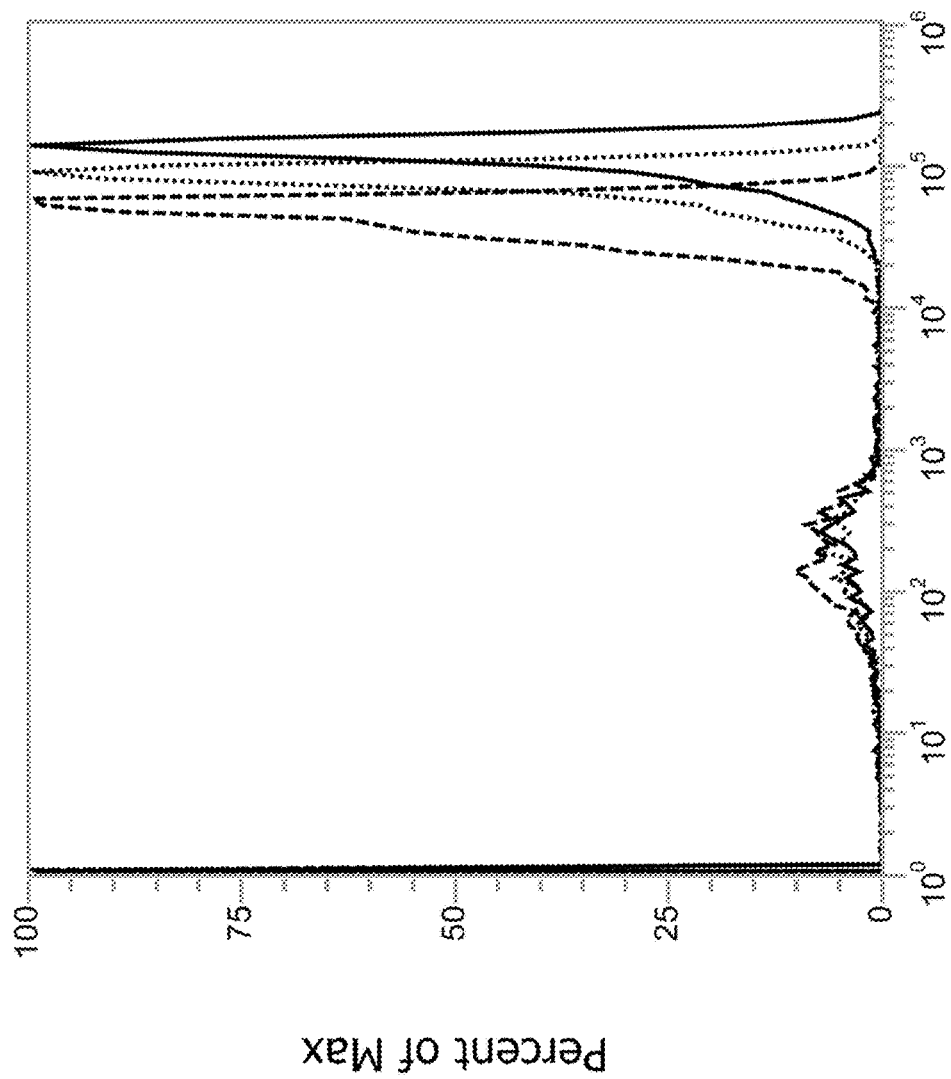

FIG. 22: SK3 mouse anti-human CD4 antibody conjugated with AF647 branched PEG constructs. SK3 mouse anti-human CD4 antibody (at 5.5. mg/mL) was modified with ALEXA FLUOR® 647 succinimidyl ester at 10 fold molar excess ester to antibody (dashed line). SK3, which was tagged with 10-fold excess of Azido-SE to antibody, was click conjugated to 100 μM AF647-HG20K8 PEG-sDIBO at 1 mg/mL azido-SK3 antibody for 20 hours at 25° C., quenched with 5 mM $NaN_3$ and conjugate was purified with Millipore AMICON™ Ultra-2 100 kDa centrifugal filter (dotted line). SK3, which was tagged with 20-fold excess of Azido-SE to antibody, was click conjugated to 600 μM AF647-HG20K8 PEG-sDIBO at 3 mg/mL azido-SK3 antibody for 3 hours at 37° C., quenched with 5 mM $NaN_3$ and conjugate was purified with Millipore AMICON™ Ultra-2 100 kDa centrifugal filter (solid line). One million Ficoll-isolated PBMC/well in a 96 well plate were stained with the SK3 conjugates using a 7 point titration of 1 μg to 0.015 μg of antibody. Analysis of the stained cells was carried out using the ATTUNE™ NxT Flow Cytometer.

Figure 23:
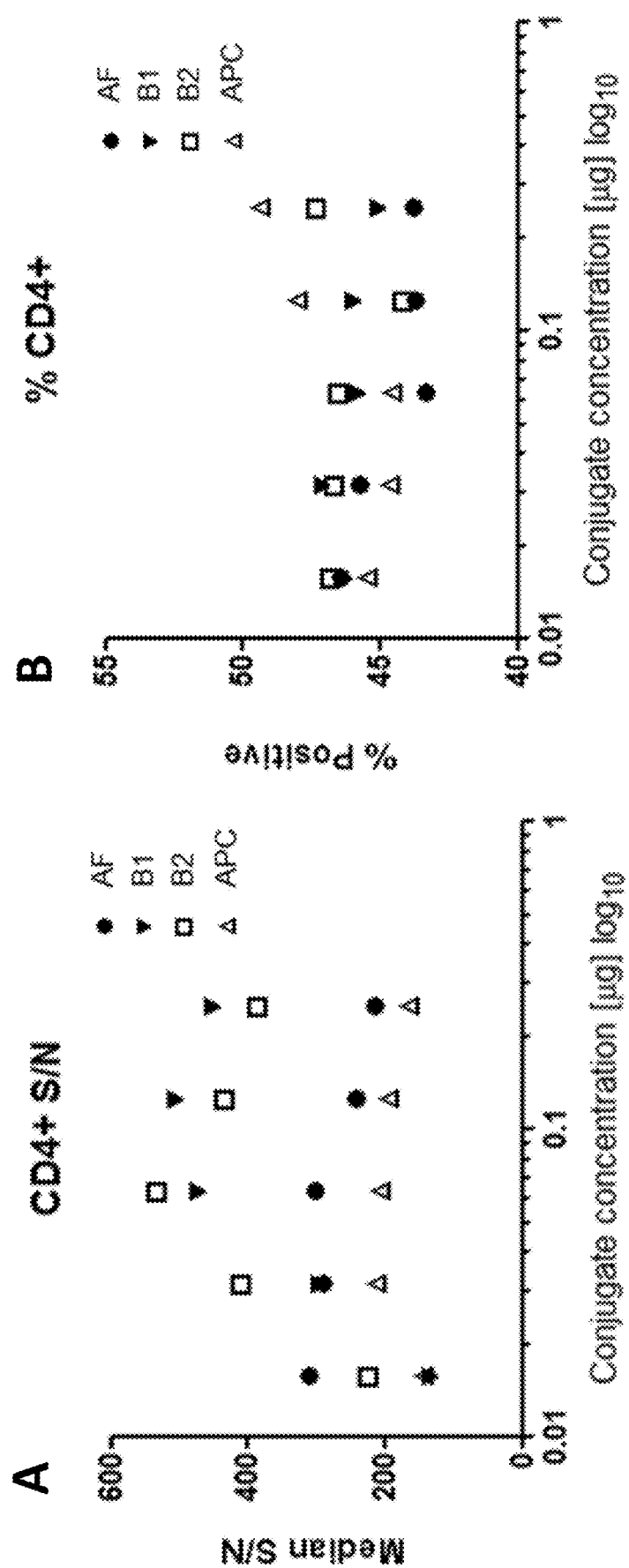

FIG. 23: SK3 mouse anti-human CD4 antibody conjugated with AF647 branched PEG constructs. SK3 mouse anti-human CD4 antibody (at 5.5. mg/mL) was modified with ALEXA FLUOR® 647 succinimidyl ester at 10 fold molar excess ester to antibody (AF). SK3, which was tagged with 20-fold excess of Azido-SE to antibody, was click conjugated to 600 μM AF647-HG20K8 PEG-sDIBO at 3 mg/mL azido-SK3 antibody for 3 hours at 37° C., quenched with 5 mM $NaN_3$ and conjugate was purified with Millipore AMICON™ Ultra-2 100 kDa centrifugal filter (B1). SK3, which was tagged with 10-fold excess of Azido-SE to antibody, was click conjugated to 100 μM AF647-HG20K8 PEG-sDIBO at 1 mg/mL azido-SK3 antibody for 20 hours at 25° C., quenched with 5 mM $NaN_3$ and conjugate was purified with Millipore AMICON™ Ultra-2 100 kDa centrifugal filter (B2). One million Ficoll-isolated PBMC/well in a 96 well plate were stained with the SK3 conjugates using a 7 point titration of 1 μg to 0.015 μg of antibody. Analysis of the stained cells was carried out using the ATTUNE™ NxT Flow Cytometer and compared to allophycocyanin (APC) (Thermo Fisher Scientific, cat. no. MHCD0405).

DETAILED DESCRIPTION

Fluorescent labels are widely used for imaging because they provide direct, quantitative, specific and sensitive detection of biomolecules including proteins and nucleic acids. Modified fluorescent labels that are sulfonated and/or PEG modified offer increased sensitivity compared to the basic unmodified dyes. However, even these modified fluorescent labels exhibit fluorescence quenching at certain dye to protein (D/P) ratios.

Increase in fluorescence is seen with increasing molar excesses of the labeling dye, however, molar excesses which result in exceeding optimal dye to protein (D/P) ratios, typically result in quenching and/or precipitation of the biomolecule especially in fluorescent imaging application where spatial conformation of antigen/antibody or DNA/RNA interactions may cause static quenching.

In some embodiments, the invention comprises methods of reducing quenching and/or increasing fluorescence signal with highly labeled conjugates (e.g., biomolecules with high dye to protein ratios (D/P)) that in standard conjugation results in decreased fluorescence. Modifications can be made on proteins, nucleic acids and other biomolecules (e.g., oligosaccharides). In some embodiments, the invention comprises compositions comprising fluorescently labeled biomolecules that exhibit increased fluorescent signal and/or reduced quenching, wherein the composition comprises a biomolecule, a spacer, and a fluorescent label, wherein the spacer and fluorescent label are not directly conjugated to each other.

The invention also relates to compositions which exhibit enhanced fluorescence on a per fluorescent label basis, as well as methods for producing and using such compositions. By way of illustration, assume that a single fluorescent label attached to a biomolecule sets a baseline of 100% fluorescent emission. Further assume, when two fluorescent labels are attached to the same biomolecule, that each of the two fluorescent labels exhibits an average of 80% of the baseline fluorescent emission. The invention is directed, in part, to compositions and methods for increasing the average fluorescent emission above the 80% of the baseline.

In some instances, compositions of the invention, as well as compositions used in methods of the invention, may be defined by one or more functional property. Examples of such properties are the numbers of fluorescent labels associated with a labeled molecule (e.g., a biomolecule), the average distance (measured in any of a number of different ways) between fluorescent labels on the labeled molecule, and/or the quantum yield of fluorescent labels on the labeled molecule.

One measure of measuring fluorescent intensity is by measurement of Quantum Yield. Quantum Yield (Φ) for fluorescent systems is effectively the emission efficiency of a given fluorophore and may be determined by the equation:

$$\Phi = \frac{\text{Number of Photons Emitted}}{\text{Number of Photons Absorbed}}$$

Quantum Yield may also be used to measure quenching effects, as set out below in Example 8. Further, instruments, such as the Hamamatsu Absolute PL Quantum Yield Spectrometer (Hamamatsu Corp., Bridgewater N.J. 08807, C11347-11Quantaurus-QY Absolute PL Quantum Yield Spectrometer), that may be used to measure quantum yield are commercially available.

As set out in Example 8 and Table 25, quantum yield of a fluorescently labeled molecule can be compared to that of the free fluorescent label. If the quantum yield of a single unit of the free fluorescent label under conditions where effectively no quenching occurs is set as one, then this can be used as a benchmark for comparison of the fluorescence generated by each fluorescent label attached to the labeled molecule. In many instances, compositions of the invention include fluorescently labeled molecules that are labeled with multiple fluorescent labels where the average amount of fluorescent emission on a per fluorescent label basis is at least 70% (0.7 Fluorescent Ratio) (e.g., from about 70% to about 99%, from about 70% to about 90%, from about 80% to about 99%, from about 85% to about 99%, from about 87% to about 99%, from about 90% to about 99%, from about 80% to about 95%, from about 85% to about 96%, etc.) of the fluorescent emission of the free fluorescent label.

As set out in Example 8 and Table 25, fluorescent intensity may be determined is by the measurement of total fluorescence of a fluorescently labeled molecule compared to the fluorescence of the free label. If the fluorescence of a single unit of the free fluorescent label under conditions where effectively no quenching occurs is set as one, then this can be used as a benchmark for comparison of the fluorescence generated by each fluorescent label attached to the labeled molecule. In many instances, compositions of the invention include fluorescently labeled molecules that are labeled with multiple fluorescent labels where the average amount of fluorescent emission on a per fluorescent label basis is at least 70% (0.7 Fluorescent Ratio) (e.g., from about 70% to about 99%, from about 70% to about 90%, from about 80% to about 99%, from about 85% to about 99%, from about 87% to about 99%, from about 90% to about 99%, from about 80% to about 95%, from about 85% to about 96%, etc.) of the fluorescent emission of the free fluorescent label.

As set out in Table 25, the brightness of a fluorescently labeled molecule compared to the free fluorescent label can be determined. Brightness is proportional to the product of quantum yield ($\Phi$), extinction coefficient (E) and number of dyes per molecule (N) as given in the equation:

$$B = \Phi \times \varepsilon \times N$$

Thus the ratio of the brightness of the free fluorescent label to that of the labeled molecule can be used to describe the total fluorescence enhancement.

As an example, the data in Table 25 sets as a benchmark ALEXA FLUOR® 647 in deionized water. Further, this sets a benchmark of 100% quantum yield of free dye and a brightness ratio of 1.0. Amongst samples, the molecule AF647-20K8 had 73% of the quantum yield of the free dye but showed a fluorescent enhancement of 5.8× over the free dye. It is also shown that the sample AF647-10K4 had the highest percent quantum yield of the free dye (89%) but had a fluorescent enhancement of only 3.6× versus the free dye. These data show that the degree of fluorescent enhancement seen for these molecules can be directly correlated with the length of the arms. The data also show that when arm length is held constant and more fluorescently labeled arms are added to a polymer, then the fluorescent enhancement tends to increase.

The invention thus includes compositions and methods for linking multiple fluorescent labels to individual molecules (e.g., biomolecules) such that the fluorescent labels are spaced in a manner that enhances fluorescent signal. This may be done by the reduction of quenching. One method for enhancing fluorescent signal is to spatially separate fluorescent labels present in a sample. This is especially useful when multiple fluorescent labels are attached to the same molecule (e.g., biomolecule) that is to be detected.

In some aspects, the invention comprises methods of producing an antibody conjugated to a spacer and a fluorescent label, wherein a spacer agent is used to conjugate a spacer to an antibody, and wherein the spacer is not conjugated to the fluorescent label. Also encompassed are compositions comprising a spacer, an antibody, and a fluorescent label, wherein the spacer is not conjugated to the fluorescent label.

In some embodiments, the spacer may be capable of reducing quenching of a plurality of fluorescent labels conjugated to an antibody.

In some embodiments, a method of producing a nucleic acid conjugated to a spacer agent is encompassed, wherein the spacer agent is not directly conjugated to the fluorescent label. Such spacer agents may be capable of reducing quenching of a fluorescent label conjugated to a nucleic acid.

In some embodiments, the invention includes compositions and methods related to the spatial separation fluorescent labels from the point on a molecule (e.g., biomolecule) to which they are conjugated to. In many instances, this will be done by connection for one or more fluorescent labels to a spacer and connection of the spacer to the molecule (e.g., biomolecule). Example of such compositions and methods are shown in FIG. 18.

Definitions

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As used herein, a "biomolecule" refers to any molecule that may be included in a biological system, including but not limited to, a synthetic or naturally occurring protein or fragment thereof, glycoprotein, lipoprotein, amino acid, nucleoside, nucleotide, nucleic acid, oligonucleotide, DNA, RNA, carbohydrate, sugar, lipid, fatty acid, hapten, antibody, and the like.

The terms "protein" and "polypeptide" are used herein in a generic sense to include polymers of amino acid residues of any length. The term "peptide" as used herein refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally used. In addition, other peptidomimetics are also useful in the present invention. For a general review, see, Spatola, A. F., in *Chemistry and Biochemistry of Amino Acids, Peptides and Proteins*, B. Weinstein, eds., Marcel Dekker, New York, p. 267 (1983).

The term "antibody" as used herein refers to a protein of the immunoglobulin (Ig) superfamily that binds noncovalently to certain substances (e.g., antigens and immunogens) to form an antibody-antigen complex, including but not limited to antibodies produced by hybridoma cell lines, by immunization to elicit a polyclonal antibody response, by chemical synthesis, and by recombinant host cells that have been transformed with an expression vector that encodes the antibody. In humans, the immunoglobulin antibodies are classified as IgA, IgD, IgE, IgG, and IgM and members of each class are said to have the same isotype. Human IgA and IgG isotypes are further subdivided into subtypes $IgA_1$, and $IgA_2$, and $IgG_1$, $IgG_2$, $IgG_3$, and $IgG_4$. Mice have generally the same isotypes as humans, but the IgG isotype is subdivided into $IgG_1$, $IgG_2a$, $IgG_2b$, and $IgG_3$ subtypes. Thus, it will be understood that the term "antibody" as used herein includes within its scope (a) any of the various classes or sub-classes of immunoglobulin (e.g., IgA, IgD, IgG, IgM, and IgE derived from any animal that produced antibodies) and (b) polyclonal and monoclonal antibodies, such as murine, chimeric, or humanized antibodies. Antibody molecules have regions of amino acid sequences that can act as an antigenic determinant (e.g. the Fc region, the kappa light chain, the lambda light chain, the hinge region, etc.). An antibody that is generated against a selected region is designated anti-[region] (e.g., anti-Fc, anti-kappa light chain, anti-lambda light chain, etc.). An antibody is typically generated against an antigen by immunizing an organism with a macromolecule to initiate lymphocyte activation to express the immunoglobulin protein. The term antibody, as used herein, also covers any polypeptide or protein having a binding domain that is, or is homologous to, an antibody binding domain, including, without limitation, single-chain Fv molecules (scFv), wherein a VH domain and a VL domain are linked by a peptide linker that allows the two domains to associate to form an antigen binding site (Bird et al., *Science* 242:423 (1988) and Huston et al., *Proc. Natl. Acad. Sci. USA* 85:5879 (1988)). These can be derived from natural sources, or they may be partly or wholly synthetically produced.

Further, VHH antibodies may be used either as obtained from antigen stimulated cells or as engineered antigen binding proteins.

The term "antibody fragments" as used herein refers to fragments of antibodies that retain the principal selective binding characteristics of the whole antibody. Particular fragments are well-known in the art, for example, Fab, Fab', and $F(ab')_2$, which are obtained by digestion with various proteases and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward et al., *Nature* 341:544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

Exemplary VHH antibodies that may be used are single-domain antibody that are antibody fragments composed of a single monomeric variable antibody domain. Such antibody fragments typically have a molecular weight of only 12-25 kDa and are thus smaller than many other antibodies (150-160 kDa), which are composed of two heavy protein chains and two light chains.

As used herein, an "antigen" refers to a molecule that induces, or is capable of inducing, the formation of an antibody or to which an antibody binds selectively, including but not limited to a biological material. Antigen also refers to "immunogen". An antibody binds selectively to an antigen when there is a relative lack of cross-reactivity with or interference by other substances present.

The term "reactive group" as used herein refers to a group that is capable of reacting with another chemical group to form a covalent bond, i.e., is covalently reactive under suitable reaction conditions, and generally represents a point of attachment for another substance. Reactive groups generally include nucleophiles, electrophiles and photoactivatable groups. Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids, alkynes and azides.

As used herein, a "spacer," "spacer molecule," or "spacer agent" refers to a compound (e.g., an organic compound) that when conjugated to a biomolecule, directly or indirectly, is capable of enhancing fluorescence emitted from the biomolecule. This is believed to result from reduction of fluorescent quenching of a fluorescent label. Any number of compounds can act as spacers, exemplary compounds include NHS-acetate and various forms of polyethylene glycol (PEG). As used herein, the term "polyethylene glycol" or "PEG" refers to an oligomer or polymer of ethylene oxide. PEG polymer chain lengths may vary greatly but tended to have a molecular mass as high as 10,000,000 g/mol. PEGs are also available with different geometries. For example, branched PEGs typically have three to ten PEG chains emanating from a central core group. Star PEGs have 3 to 100 PEG chains emanating from a central core group. Comb PEGs have multiple PEG chains normally grafted onto a polymer backbone. Most PEGs include molecules with a distribution of molecular weights (i.e., they are polydisperse). The size distribution can be characterized statistically by its weight average molecular weight and its number average molecular weight, the ratio of which is called the polydispersity index. Exemplary PEG compounds that may be used in the practice of the invention include $MS(PEG)_4$, $MS(PEG)_8$, and $MS(PEG)_{12}$ (Thermo Fisher Scientific, Waltham, Mass., cat. nos. 22341, 22509B, and 22686, respectively), as well as branched chain PEG compounds, such as (Methyl-$PEG_{12}$)3-$PEG_4$-NHS Ester (Thermo Fisher Scientific, Waltham, Mass., cat. no. 22421).

As used herein, the term "direct spacer" refers to a molecule that has at least one fluorescent labeled attached thereto and binds directly to a biomolecule. Direct spacers may be (1) a single polymer or (2) multiple polymers attached to a core. Examples of direct spacers include single-armed polymers and multi-armed polymers.

As used herein, a "polymer" is a molecule composed of repeating subunits (typically at least 4 repeating subunits). Polymers may be synthetic or naturally occurring. The repeating units of a polymer need not be identical. For example, proteins are polymers that are composed of different amino acid subunits. Further, polymers need not be fully linear molecules and, thus, may be branched likedextrans.

As used herein, the term "single-armed polymer" refers to an unbranched molecule that to which at least one fluorescent label is attached and having an unbranched structure (see FIG. 19). Examples of single-armed polymers that may be used in the practice of the invention are "linear" polysaccharides (e.g., amylose), polyethylene glycols, long-chain carbon molecules (e.g., Ahx), and polypeptides. In some instances, unbranched/linear polysaccharides are composed of monomers connected to each other by α1,4 linkages.

As used herein, the term "multi-armed polymer" refers to a branched molecule that to which at least one fluorescent label is attached and having an unbranched structure (see FIG. 19). Examples of multi-armed polymers that may be used in the practice of the invention are branched polysaccharides (e.g., dextrans, glycogen), polyethylene glycols, branched long-chain carbon molecules (e.g., Ahx), and branched polypeptides.

As used herein, the term "conjugation molecule" or "conjugation arm" refers linkers through which dyes are connected (e.g., covalently connected) to molecules (e.g., biomolecules). Conjugation molecule may be bound to a single dye molecule or multiple dye molecules (the same dye or different dyes).

As used herein, the term "fluorescence" refers to an optical phenomenon in which a molecule absorbs a high-energy photon and re-emits it as a lower-energy (longer-wavelength) photon, with the energy difference between the absorbed and emitted photons ending up as molecular vibrations or heat.

The term "fluorescent label," "fluorescent dye," "fluorophore" or "fluorescent moiety", as used herein, refers to a compound, chemical group, or composition that is inherently fluorescent. Fluorophores may contain substituents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a furan, a benzazole, a borapolyazaindacene and xanthenes including fluorescein, rhodamine and rhodol as well as other fluorophores described in RICHARD P. HAUGLAND, MOLECULAR PROBES HANDBOOK OF FLUORESCENT PROBES AND RESEARCH CHEMICALS (9th edition, CD-ROM, September 2002). Reactive chemistries such as N-hydroxysuccinimide (NHS), maleimide and hydrazides as well as click chemistry (e.g. SITE-CLICK™) are currently being used for conjugation of florescent labels to biomolecules.

As used herein, the term "conjugated" refers to a molecule being attached to another molecule, either directly or indirectly, either by covalent or noncovalent linkage.

The term "dye conjugate" refers to a dye molecule bound covalently or non-covalently to another carrier molecule, such as an antibody and, in many instances, the dyes are bound covalently. The dye conjugate can be directly bound through a single covalent bond, cross-linked or bound through a linker, such as a series of stable covalent bonds incorporating 1-20 non-hydrogen atoms selected from the group consisting of C, N, O, S and P that covalently attach the fluorescent dye to the antibody or another moiety such as a chemically reactive group or a biological and non-biological component. The conjugation or linker may involve a receptor binding motif, such as biotin/avidin.

The term "near IR dye" or "near IR reporter molecule" or "NIR dye" or "NIR reporter molecule" as used herein indicates a dye or reporter molecule with an excitation wavelength of about 580 nm to about 800 nm. In many instances, the NIR dyes emit in the range of about 590 nm to about 860 nm. In many instances, NIR dyes are excited from about 680 to about 790 nm. In many instances, dyes include ALEXA FLUOR® 660 Dye, ALEXA FLUOR® 680 dye, ALEXA FLUOR® 700 dye, ALEXA FLUOR® 750 dye, and ALEXA FLUOR® 790 dye. The NIR dyes are particularly advantageous for in vivo imaging because they can be selectively visualized without exciting endogenous materials present in living body. Some of the NIR dyes have a large stokes shift, such that the excitation and emission wavelengths are separated by at least 20, 30, 40, 50, 60, 70 or 80 nm.

"Solid support" means a substrate material having a rigid or semi-rigid surface. Typically, at least one surface of the substrate will be substantially flat, although it may be desirable to physically separate certain regions with, for example, wells, raised regions, etched trenches, or other such topology. Solid support materials also include spheres (including microspheres), rods (such as optical fibers) and fabricated and irregularly shaped items.

Solid support materials include any materials that are used as affinity matrices or supports for chemical and biological molecule syntheses and analyses, such as, but are not limited to: poly(vinylidene difluoride) (PVDF), polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrylamide non-covalent composite, polystyrene-polyacrylamide covalent composite, polystyrene-PEG [poly(ethylene glycol)] composite, silicon, rubber, and other materials used as supports for solid phase syntheses, affinity separations and purifications, hybridization reactions, immunoassays and other such applications. The solid support may be particulate or may be in the form of a continuous surface, such as a microtiter dish or well, a glass slide, a silicon chip, a nitrocellulose sheet, nylon mesh, or other such materials.

"Kit" means a packaged set of related components, typically one or more compounds or compositions.

Detectable Biomolecules

Disclosed herein, in some embodiments, are biomolecules that are detectably labeled with a plurality of fluorescent labels that also comprise a spacer agent.

a. Spacers

A spacer may be any molecule that is capable of enhancing fluorescent emissions when conjugated to a biomolecule that results from excitation of a plurality of fluorescent labels independently conjugated to the biomolecule. It is believed that this is due to the reduction of fluorescence quenching of the fluorescent labels.

In some embodiments, the spacer comprises an acetyl (—C(O)CH$_3$) group. In some embodiments, the spacer is an acetate molecule. In some embodiments, the acetate molecule is sulfo-NHS-acetate.

In some embodiments, the spacer agent comprises polyethylene glycol (PEG). In some embodiments, the spacer agent comprises (PEG)n, wherein n is selected from 1, 2, 3, 4, 5, 6, 7, 8, 9, 10, 11, 12, 13, 14 or 15. In some embodiments, the spacer agent comprises MS-(PEG)n.

In some embodiments, the spacer is selected from an alkanoyl, alkenoyl, and alkynoyl (—C(O)C$_n$H$_m$ in which n is 1 to 20 atoms, m>n, the carbon atoms can be connected to each other by single, double, and/or triple bonds, and the alkyl, alkenyl, and/or alkynyl groups can be further substituted. In some embodiments, specific substitutions include poly(ethylene)glycol moieties, such as —(OCH$_2$CH$_2$O)$_x$—(CH$_2$)$_y$—OR in which x is 1 to 20, y is 1 to 6, and R is H or C$_{1-6}$ alkyl. In some embodiments, specific substitutions include ammonium (—NH$_3^+$), quaternary ammonium ((—NR$_3$+) groups in which R is C$_{1-6}$ alkyl, or phosphonium groups (—PQ$_3^+$) in which Q is aryl, substituted aryl, or C$_{1-6}$ alkyl.

In some embodiments, the spacer is selected from alkyl, alkenyl, or alkynyl groups (—C$_n$H$_m$ in which n is 1 to 20 atoms, m>n, the carbon atoms can be connected to each other by single, double, and/or triple bonds, and the alkyl, alkenyl, and/or alkynyl groups can be further substituted. In some embodiments, specific substitutions include negatively charged sulfonate groups (—OSO$_3$—), carboxylate groups (—CO$_2$—), phosphate groups (—OPO$_3$—), and/or phosphonate groups (—PO$_3$—). In some embodiments, other substitutions include poly(ethylene)glycol moieties, such as —(OCH$_2$CH$_2$O)$_x$—(CH$_2$)$_y$—OR in which x is 1 to 20, y is 1-6, and R is H or C$_{1-6}$ alkyl. In some embodiments, other specific substitutions include ammonium (—NH$_3^+$), quaternary ammonium ((—NR$_3^+$) groups in which R is C$_{1-6}$ alkyl, or phosphonium groups (—PQ$_3^+$) in which Q is aryl, substituted aryl, or C$_{1-6}$ alkyl.

In some embodiments, the spacer is positively charged. In some embodiments, the spacer agent comprises betaine (i.e., trimethylglycine).

In some embodiments, the spacer agent is negatively charged.

b. Fluorescent Label

The fluorescent dyes described herein function as reporter molecules to confer a detectable signal, directly or indirectly, to the sample as a result of conjugation to a functional group on the protein, including, but not limited to, amine groups or thiol groups. This results in the ability to detect the total protein in a sample generally in combination with detection of a subset of the total protein of the sample. In such instances the total protein labels are detectable distinguished from the dye that labels a subset of the total protein in the sample.

Where the detectable response is a fluorescence response, it is typically a change in fluorescence, such as a change in the intensity, excitation or emission wavelength, distribution of fluorescence, fluorescence lifetime, fluorescence polarization, or a combination thereof.

The fluorescent dyes can be any fluorophore known to one skilled in the art. Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

A wide variety of fluorophores that may be suitable for total protein labeling as described herein are already known in the art (RICHARD P. HAUGLAND, MOLECULAR PROBES HANDBOOK OF FLUORESCENT PROBES AND RESEARCH PRODUCTS (2002)). A fluorescent dye used in the methods and compositions described herein is any chemical moiety that exhibits an absorption maximum beyond 280 nm. Such chemical moieties include, but are not limited to, a pyrene, sulfonated pyrenes, sulfonated coumarins, sulfonated carbocyanines, sulfonated xanthenes, an anthracene, a naphthalene, an acridine, a stilbene, an indole an isoindole, an indolizine, a benzindole, an oxazole or benzoxazole, a thiazole or benzothiazole, a 4-amino-7-nitrobenz-2-oxa-1,3-diazole (NBD), a carbocyanine, a carbostyryl, a porphyrin, a salicylate, an anthranilate, an azulene, a perylene, a pyridine, a quinoline, an isoquinoline, a chromene, a borapolyazaindacene, a xanthene, a fluorescein, a rosamine, a rhodamine, a rhodamine, benzo- or dibenzofluorescein, seminaphthofluorescein, a naphthofluorescein, a bimane, an oxazine or a benzoxazine, a carbazine, a phenalenone, a coumarin, a benzofuran, a benzphenalenone) and derivatives thereof. As used herein, oxazines include resorufins, aminooxazinones, diaminooxazines, and their benzo-substituted analogs.

In one aspect the fluorescent dyes contain one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art. In one aspect the fluorophore is a xanthene that comprises one or more julolidine rings.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group, solid support and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. In many instances, dyes are rhodamine, fluorescein, borapolyazaindacene, indole and derivatives thereof.

Choice of the reactive group used to attach the total protein labels or expression tag labels to the protein to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. In proteins a variety of sites may occur including, but not limited to, amines, thiols, alcohols and phenols.

Amine reactive fluorescent dyes that can be used in the protein labeling methods described herein include, but are not limited to, ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610-X, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, AMCA-X, BODIPY® 630/650, BODIPY® 650/665, BODIPY® FL, BODIPY® TMR, BODIPY® TR, BODIPY® TR-X, CASCADE BLUE®, Dinitrophenyl, Fluorescein, HEX, JOE, MARINA BLUE®, OREGON GREEN® 488, OREGON GREEN® 514, PACIFIC BLUE™, PACIFIC ORANGE™, RHODAMINE GREEN™, QSY® 7, QSY® 9, QSY® 21, QSY® 35, ROX, RHODAMINE RED™, TET, TAMRA, tetramethyl rhodamine, FAM, TEXAS RED® and 7-hydroxy-9H-(1,3-dichloro-9,9-dimethylacridin-2-one) succinimidyl ester (DDAO-SE).

In some embodiments, the fluorogenic reagents/dyes that bind to tags attached to proteins used in the protein labeling methods described herein are biarsenical fluorophore, including, a biarsenical derivative of fluorescein, such as, by way of example only, FlAsH-EDT2 (4'-5'-bis(1,3,2-dithio-arsolan-2-yl)fluorescein-(2,2-ethanedithiol)2) (LUMIO™ Green, Life Technologies Corp., Carlsbad, Calif.), or a biarsenical derivative of resorufin such as, by way of example only, ReAsh-EDT2 (LUMIO™ Red, Life Technologies Corp., Carlsbad, Calif.), or may instead be an oxidized derivative, such as ChoXAsH-EDT2 or HoXAsH-EDT2. In addition, the biarsenical fluorophore can be a biarsenical derivative of other known fluorophores, including, but not limited to, the ALEXA FLUOR® series described herein, such as, by way of example only, ALEXA FLUOR® 350, ALEXA FLUOR® 430, ALEXA FLUOR® 488, ALEXA FLUOR® 532, ALEXA FLUOR® 546, ALEXA FLUOR® 568, ALEXA FLUOR® 594, ALEXA FLUOR® 663 and ALEXA FLUOR® 660, available commercially from Molecular Probes (Eugene, Oreg.).

In some embodiments, the biarsenical fluorophore can be present at a concentration of at least about 1 µM, 2 µM, 3 µM, 4 µM, 5 µM, 10 µM, 15 µM, 20 µM, 30 µM, 40 µM, 50 µM, 100 µM or more, and at a concentration of no more than about 500 µM, 400 µM, 300 µM, 200 µM, 100 µM, 90 µM, 80 µM, 70 µM, 60 µM, 50 µM, 40 µM, 30 µM, 20 µM, 15 µM, 10 µM, 5 µM, 4 µM, 3 µM, 2 µM or 1 µM.

In some embodiments, the tag attached to a protein to which such fluorogenic dyes binds is a tetracysteine peptide motif, cys-cys-Xn-cys-cys (SEQ ID NO: 1), wherein each X is any natural amino acid, non-natural amino acid or combination thereof, and n is an integer from 2-100. In certain embodiments, n is an integer from 2-90, while in other embodiments n is an integer from 2-80. In certain embodiments, n is an integer from 2-70, while in other embodiments n is an integer from 2-60. In certain embodiments, n is an integer from 2-50, while in other embodiments n is an integer from 2-40. In certain embodiments, n is an integer from 2-30, while in other embodiments n is an integer from 2-20. In certain embodiments, n is an integer from 2-10, while in other embodiments n is an integer from 2-5. The natural amino acids if such motifs include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In certain embodiments, the tetracysteine tag has the sequence CCPGCC (SEQ ID NO: 2). In other embodiments a 12 amino acid peptide containing the tetracysteine motif is used including, but not limited to, the amino acid sequence, AGGCCPGCCGGG (SEQ ID NO: 3). In addition, the protein can be labeled with a single tetracysteine tag or the protein can be labeled with a plurality of tetracysteine tags including, but not limited to, 2, 3, 4, 5, 6, 7, 8, 9, 10, 11, 12, 13, 14, 15, 16, 17, 18, 19 or 20 tetracysteine tags. Such tags may be separated from one another within the primary amino acid sequence of the protein or directly multimerized in tandem as concatemers.

In certain embodiments, the tetracysteine peptide has the sequence cys-cys-Xn-cys-X-cys-X (SEQ ID NO: 1), wherein each X is any natural amino acid, non-natural amino acid or combination thereof, and n is an integer from 2-100. In certain embodiments, n is an integer from 2-90, while in other embodiments n is an integer from 2-80. In certain embodiments, n is an integer from 2-70, while in other embodiments n is an integer from 2-60. In certain embodiments, n is an integer from 2-50, while in other embodiments n is an integer from 2-40. In certain embodiments, n is an integer from 2-30, while in other embodiments n is an integer from 2-20. In certain embodiments, n is an integer from 2-10, while in other embodiments n is an integer from 2-5. The natural amino acids if such motifs include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In certain embodiments, the tetracysteine tag has the sequence CCGGKGNGGCGC (SEQ ID NO: 4).

The tetracysteine peptide tag or tags can be recombinantly fused to the protein desired to be labeled, either at the N-terminus, C-terminus, or in frame within the protein sequence; expression vectors for creating tetracysteine-fused recombinant proteins may readily be constructed using techniques known to one of skill in the art. In certain embodiments the tetracysteine-tagged protein is expressed recombinantly in host cells including, but not limited to, in bacterial host cells, in fungal host cells, in insect cells, in plant cells, or in mammalian cells. Such bacterial host cells include, but are not limited to, gram negative and gram positive bacteria of any genus, including, by way of example only, *Escherichia* sp. (e.g., *E. coli*), *Klebsiella* sp., *Streptomyces* sp., *Streptococcus* sp., *Shigella* sp., *Staphylococcus* sp., *Erwinia* sp., *Klebsiella* sp., *Bacillus* sp. (e.g., *B. cereus, B. subtilis* and *B. megaterium*), *Serratia* sp., *Pseudomonas* sp. (e.g., *P. aeruginosa* and *P. syringae*) and *Salmonella* sp. (e.g., *S. typhi* and *S. typhimurium*). Suitable bacterial strains and serotypes suitable for the invention can include *E. coli* serotypes K, B, C, and W. A typical bacterial host is *E. coli* strain K-12. The fungal host cells include, by way of example only, *Saccharomyces cerevisiae* cells, while the mammalian cells include, by way of example only, including human cells. In such embodiments, the protein sample containing the protein of interest is a lysate of the host cells, that can be unpurified, partially purified, or substantially purified prior to labeling and analysis using the methods described herein.

In other embodiments, the tetracysteine-tagged protein is expressed in vitro, wherein the protein sample containing the protein of interest is the cell-free extract in which translation (and, optionally, transcription) is performed, or a partially purified or purified fraction thereof. In embodiments in which the extract permits coupled transcription and translation in a single cell-free extract, such as the *E. coli*-based EXPRESSWAY™ or EXPRESSWAY™ Plus systems (Life Technologies Corp., Carlsbad, Calif.), the sample is the cell-free extract in which transcription and translation commonly occur, or a fraction thereof.

Alternatively, GATEWAY® Technology (Life technologies Corp., Carlsbad, Calif.) is a universal cloning technology that can be used to express a gene of interest in *E. coli*. The protein to be labeled using the biarsenical dyes described herein can be any protein having a tetracysteine motif. The protein to which the tetracysteine tag or tags is fused or conjugated can be any protein desired to be labeled, either naturally-occurring or nonnaturally occurring. Naturally-occurring proteins may have known biological function or not, and may be known to be expressed or only predicted from genomic sequence. The protein, if naturally-occurring, can be a complete protein or only a fragment thereof. The tetracysteine-tagged protein can thus be an animal protein, such as a human protein or non-human mammalian protein, a fungal protein, a bacterial protein, including eubacterial and archaebacterial protein, a plant protein, an insect protein or a viral protein.

In addition to the tetracysteine tag, other protein sequences can usefully be recombinantly appended to the proteins desired to be labeled. Among such additional protein sequences are linkers and/or short tags, usefully epitope tags, such as a FLAG tag, or a myc tag, or other sequences useful for purification, such as a polyhistidine (e.g., 6×his) tag. Alternatively, the tetracysteine tag or tags can be chemically conjugated to proteins to be labeled using art-routine conjugation chemistries.

In some embodiments, the fluorescent label is positively charged. In some embodiments, the fluorescent label is negatively charged.

In some embodiments, the excitation wavelength of the fluorescent label is between 350 and 850 nm. In some embodiments, the excitation wavelength of the fluorescent label is far red. In some embodiments, the excitation wavelength of the fluorescent label is near infrared. In some embodiments, the excitation wavelength of the fluorescent label is ultraviolet (UV).

In some embodiments, the fluorescent label comprises a DyLight™® fluor. In some embodiments, the DyLight™® fluor is selected form DyLight™ 350, DyLight™ 405, DyLight™ 488, DyLight™ 550, DyLight™ 594, DyLight™ 633, DyLight™ 650, DyLight™ 680, DyLight™ 755, and DyLight™ 800. In some embodiments, the DyLight™ fluor is conjugated to a PEG molecule (e.g., 2×PEG, 4XPEG, 8XPEG, or 12×PEG).

In some embodiments, the fluorescent label comprises an Alexa Fluor®. In some embodiments, the Alexa Fluor® is selected from Alexa Fluor® 350, Alexa Fluor® 405, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750 and Alexa Fluor® 790.

In some embodiments, the fluorescent label comprises a moiety selected from xanthene; coumarin; cyanine; pyrene; oxazine; borapolyazaindacene; benzopyrylium; and carbopyronine.

In some embodiments, the fluorescent label comprises fluorescein (e.g., Cy2 or FITC). In some embodiments, the fluorescent label comprises rhodamine (e.g., TRITC or Cy3). In some embodiments, the fluorescent label comprises MCA, coumarin, Rhodamine Red, Texas Red, Cascade Blue, Cy5, Cy5.5, IR680, IR800 and Cy7.

In some embodiments, the fluorescent label is a modified fluorescent label (e.g., the fluorescent label has been sulfonated or conjugated with PEG).

In some embodiments, the fluorescent label is a fluorescent protein. In some embodiments, the fluorescent protein is a phycobiliprotein. Examples of phycobiliproteins useful in the present invention are allophycocyanin, phycocyanin, phycoerythrin, allophycocyanin B, B-phycoerythrin, phycoerythrocyanin, and b-phycoerythrin. The structures of phycobiliproteins have been studied and their fluorescent spectral properties are known. See A. N. Glazer, "Photosynthetic Accessory Proteins with Bilin Prosthetic Groups," Biochemistry of Plants, Volume 8, M. D. Hatch and N. K. Boardman, EDS., Academic Press, pp. 51-96 (1981), and A. N. Glazer, "Structure and Evolution of Photosynthetic Accessory Pigment Systems with Special Reference to Phycobiliproteins," The Evolution of Protein Structure and Function, B. S. Sigman and M. A. Brazier, EDS., Academic Press, pp. 221-244 (1980). In some embodiments, the fluorescent protein has absorption maxima of at least about 450 nm, often at least about 500 nm, having Stokes shifts of at least 15 nm, often at least about 25 nm, and has fluorescence emission maxima of at least about 500 nm, often at least about 550 nm.

In some embodiments, the fluorescent label is a dipyrromethene boron difluoride dye, as disclosed in US 2014/0349,893, incorporated by reference herein, in its entirety.

The amine reactive fluorogenic reagents used in the protein labeling methods described herein include, but are not limited to, aroyl-2-quinoline-carboxaldehyde type reagents. Such reagents have been described in U.S. Pat. Nos. 5,459,272 and 5,631,374, each of which is herein incorporated by reference in their entirety. In some embodiments, the aroyl-2-quinoline-carboxaldehyde reagent used is 3-(4-carboxybenzoyl)quinoline-2-carboxaldehyde or 3-(2-furoyl)quinoline-2-carboxaldehyde). In certain embodiments, the amine reactive fluorogenic reagent is 3-(2-furoyl) quinoline-2-carboxaldehyde), while in other embodiments, the amine reactive fluorogenic reagent is 3-(4 carboxybenzoyl)-quinoline-2-carboxaldehyde.

c. Biomolecules

A biomolecule that can be used in the compositions and methods disclosed herein include any biomolecule that is useful in molecular biology applications.

In some embodiments, the biomolecule is an antibody (e.g., a primary antibody or a secondary antibody). In some embodiments, the biomolecule is an antibody fragment. Antibodies used in the practice of the invention may be antibody is polyclonal, monoclonal or engineered and may be from any source (e.g., shark, chicken or a mammal, such as a llama, human mouse, rabbit, goat, rat, etc.). Further, humanized antibodies may be used.

In some embodiments, the antibody is chimeric.

In some embodiments, the biomolecule is a protein or polypeptide. In some embodiments, the biomolecule is a recombinant polypeptide.

In some embodiments, the biomolecule is a nucleic acid molecule. In some embodiments, the nucleic acid molecule is an oligonucleotide (e.g., between 15 and 50 nucleotides in length). In some embodiments, the nucleic acid molecule is greater than 50 nucleotides in length, greater than 100 nucleotides in length, greater than 500 nucleotides in length, greater than 1 kb in length, greater than 2 kb in length, or greater than 5 kb in length.

d. Conjugation of Fluorescent Dyes to Biomolecules

After selection of an appropriate dye with the desired spectral characteristics, typically where the excitation wavelength is at least 580 nm, the dyes may be conjugated to a targeted carrier molecule, using methods well known in the art (Haugland, MOLECULAR PROBES HANDBOOK, supra, (2002)). In many instances, conjugation to form a covalent bond consists of simply mixing the reactive compounds of the present invention in a suitable solvent in which both the reactive compound and the spacer molecule to be conjugated are soluble. The reaction, in many instances, proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is, in many instances, performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of biomolecule (e.g., proteins) conjugates typically comprises first dissolving the biomolecule to be conjugated in aqueous buffer at about. 1-10 mg/mL at room temperature or below. For example, bicarbonate buffers (pH about 8.3), carbonate and borate buffers (pH about 9) are especially suitable for reaction with succinimidyl esters, phosphate buffers (pHs of about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the biomolecule to be conjugated. The appropriate amount of compound for any biomolecule (e.g., protein) or other component is conveniently predetermined by experimentation in which variable amounts of the compound are added to the biomolecule, the conjugate is chromatographically purified to separate unconjugated compound and the compound-biomolecule conjugate is tested in its desired application.

Any number of buffers may be used for conjugation reactions, as well as for other set out herein. Using Examples 1 and 5 for purposes of illustration, phosphate buffered saline and borate buffer can be and are used in the conjugation reactions. It is also believed that carbonate buffer at pH 9.5 can be used. Along these lines, it is believed that higher pH conjugations require a lower molar excess of dye and spacer molecules. The invention thus includes compositions and methods for performing conjugation reactions where the pH is from about 4.0 to about 10.0 (e.g., from about 4.0 to about 10.0, from about 5.0 to about 10.0, from about 6.0 to about 10.0, from about 7.0 to about 10.0, from about 7.5 to about 10.0, from about 8.0 to about 10.0, etc.). Conjugation reactions may be performed in Borate Buffer 50 mM, pH 8.5 with a fluorescent dye, or a mixture of each fluorescent dye and a spacer selected from NHS-Acetate, NHS-MS(PEG)$_4$, NHS-MS(PEG)$_8$ or NHS-MS(PEG)$_{12}$ at various molar excesses. The labeling reactions may be incubated for approximately 1 hour at room temperature (RT). The NHS activated dye and the NHS activated spacer agents may be combined before addition to the antibody so that both reactions are concurrent, allowing for a random spacing of the dye substitution and of the spacers.

Buffers that may be used in the practice of the invention include 2-(N-morpholino)ethanesulfonic acid (MES), phosphate, 3-(N-morpholino)propanesulfonic acid (MOPS), tris (hydroxymethyl)aminomethane (TRIS), borate, 4-(2-hydroxyethyl)-1-piperazineethanesulfonic acid (HEPES) and carbonate buffers as examples.

The concentration of the fluorogenic reagents used in the biomolecule (e.g., protein) labeling methods described herein are in the range from 50 nM to 100 mM (e.g., from about 50 nM to about 25 mM, from about 50 nM to about 10 mM, from about 50 nM to about 5 mM, from about 100 nM to about 10 mM, from about 100 nM to about 5 mM, from about 200 nM to about 5 mM, from about 50 nM to about 100 µM, from about 1 µM to about 100 µM, etc.). In certain embodiments such concentrations are obtained by dilution of a stock solution of the fluorogenic reagents having a concentration in the range from 100 nM to 200 mM (e.g., from about 10 µM to about 500 µM, from about 1 µM to about 100 µM, from about 100 µM to about 200 µM, etc.). In certain embodiments the concentration of the stock solution is 100 mM. In certain embodiments the concentration of the stock solution is 50 mM. In certain embodiments the concentration of the stock solution is 20 mM. In certain embodiments the concentration of the stock solution is 10 mM. In certain embodiments the concentration of the stock solution is 1 mM. In certain embodiments the concentration of the stock solution is 500 µM. In certain embodiments the concentration of the stock solution is 10 µM.

In some embodiments, the concentration of the amine reactive fluorescent dyes used in the biomolecule (e.g., protein) labeling methods described herein are in the range from 50 nM to about 100 mM (e.g., from about 50 nM to about 50 mM, from about 50 nM to about 25 mM, from about 50 nM to about 10 mM, from about 50 nM to about 5 mM, from about 50 nM to about 5 µM, from about 50 nM to 100 µM, from about 100 nM to about 5 mM, etc.). In certain embodiments such concentrations are obtained by dilution of a stock solution of the fluorogenic reagents having a concentration in the range from 100 nM to 200 mM. In certain embodiments the concentration of the stock solution is 100 mM. In certain embodiments the concentration of the stock solution is 50 mM. In certain embodiments the concentration of the stock solution is 20 mM. In certain embodiments the concentration of the stock solution is 10 mM. In certain embodiments the concentration of the stock solution is 1 mM. In certain embodiments the concentration of the stock solution is 500 µM. In certain embodiments the concentration of the stock solution is from 10 µM to 500 µM. In certain embodiments the concentration of the stock solution is from 1 µM to 100 µM. In certain embodiments the concentration of the stock solution is 10 µM. In certain embodiments the concentration of the stock solution is from 100 µM to 200 µM.

In some embodiments, the concentration of the proteins or protein fragments (e.g., antibody fragments) labeled using the methods described herein is in the range from 0.01 mg/mL to 200 mg/mL (e.g., from about 0.1 mg/mL to 100 mg/mL, from about 0.1 mg/mL to about 50 mg/mL, from about 0.1 mg/mL to about 10 mg/mL, from about 0.2 mg/mL to about 100 mg/mL, from about 0.2 mg/mL to about 50 mg/mL, from about 0.2 mg/mL to about 10 mg/mL, from about 0.3 mg/mL to 10 mg/mL, from about 0.4 mg/mL to about 10 mg/mL, from about 0.5 mg/mL to about 10 mg/mL etc.).

In some instances, more than one dye molecule may be attached at each location on a biomolecule. One way of attaching more than one dye molecule at a single location on a biomolecule is through the use of conjugation molecules that bind to more than one dye molecule. These conjugation molecules are then connected to the biomolecule and carry with them multiple dye molecules. As an example, polymeric dendrimers, such as those set out in U.S. Patent Publication 2012/0256102, may be used multiple fluorescent dye molecules conjugated to a single polymeric backbone or core (referred to as "dendrimers" therein) for the attachment of these dye molecules to a biomolecule. These dendrimers may have regular or irregular branched polymeric network structures that allow for the chemical attachment of multiple dye molecules, multiple color dyes, and/or multiple functional groups, in a combinatorial fashion.

Additional examples of conjugation molecules that may be used include many of the same molecules used as spacers. Thus, in some instances, the spacer molecule and the conjugation molecule will have the same structure with the exception that the conjugation molecule has dye molecules bound to it. Along these lines, various forms of PEG molecules may be used as conjugation molecules. Thus, the spacer molecule may contain the dye molecule (e.g., the fluorescent label) (see FIG. 18).

The invention thus contemplates the use of conjugation molecules that each have, on average, from about two to about fifty (e.g., from about two to about forty-five, from about two to about forty, from about two to about thirty-five, from about two to about thirty, from about two to about twenty, from about five to about forty-five, from about ten to about forty-five, etc.) associated dye molecules. In many instances, the standard deviation in the average number of dye molecules bound to conjugation molecules will be less than 10%, 15%, and/or 20%.

The degree of labeling may be measure for labeled biomolecules. Degree of labeling may be calculated as follows. First, the molarity of the labeled biomolecule is calculated using, for example, the formula:

$$\text{Protein concentration }(M) = \frac{A_{280} - (A_{max} \times CF)}{\varepsilon} \times \text{dilution factor}$$

$\varepsilon$=protein molar extinction coefficient (e.g., the molar extinction coefficient of IgG is 210,000 $M^{-1}$ $cm^{-1}$)
$A_{max}$=Absorbance (A) of a dye solution measured at the wavelength maximum ($\lambda$max) for the dye molecule
CF=Correction factor; adjusts for the amount of absorbance at 280 nm caused by the dye (see Table 8)
Dilution factor=the extent (if any) to which the protein:dye sample was diluted for absorbance measurement The degree of labeling is then calculated using the formula:

$$\text{Moles dye per mole protein} = \frac{A_{max} \text{ of the labeled protein}}{\varepsilon' \times \text{protein concentration }(M)} \times \text{dilution factor}$$

$\varepsilon'$=molar extinction coefficient of the fluorescent dye

TABLE 8

Characteristics of Exemplary Dye

| Fluorophore | Wavelength Maximum ($\lambda_{max}$) | Extinction Coefficient ($\varepsilon'$) | Correction Factor (CF) |
|---|---|---|---|
| DyLight ® 350 | 353 nm | 15,000 $M^{-1}$ $cm^{-1}$ | 0.1440 |
| DyLight 405 | 405 nm | 30,000 $M^{-1}$ $cm^{-1}$ | 0.5640 |
| DyLight 488 | 493 nm | 70,000 $M^{-1}$ $cm^{-1}$ | 0.1470 |
| DyLight 550 | 562 nm | 150,000 $M^{-1}$ $cm^{-1}$ | 0.0806 |
| DyLight 594 | 595 nm | 80,000 $M^{-1}$ $cm^{-1}$ | 0.5850 |
| DyLight 633 | 627 nm | 170,000 $M^{-1}$ $cm^{-1}$ | 0.1100 |
| DyLight 650 | 652 nm | 250,000 $M^{-1}$ $cm^{-1}$ | 0.0371 |
| DyLight 680 | 684 nm | 140,000 $M^{-1}$ $cm^{-1}$ | 0.1280 |
| DyLight 755 | 754 nm | 220,000 $M^{-1}$ $cm^{-1}$ | 0.0300 |
| DyLight 800 | 777 nm | 270,000 $M^{-1}$ $cm^{-1}$ | 0.0452 |
| Fluorescein Isothiocyanate (FITC) NHS-Fluorescein, 5-IAF | 494 nm | 68,000 $M^{-1}$ $cm^{-1}$ | 0.3000 |
| Tetramethyl-rhodamine-5-(and 6)-isothiocyanate (TRITC) | 555 nm | 65,000 $M^{-1}$ $cm^{-1}$ | 0.3400 |
| NHS-Rhodamine | 570 nm | 60,000 $M^{-1}$ $cm^{-1}$ | 0.3400 |
| Texas Red ® Sulfonyl Chloride | 596 nm | 80,000 $M^{-1}$ $cm^{-1}$ | 0.1800 |
| R-Phycoerythrin | 566 nm | 1,863,000 $M^{-1}$ $cm^{-1}$ | 0.1700 |
| AMCA-NHS, AMCA-Sulfo-NHS or AMCA-Hydrazide | 346 nm | 19,000 $M^{-1}$ $cm^{-1}$ | 0.1900 |

In some embodiments of the invention, enhanced fluorescence is observed for biomolecules comprising spacers with lower degree of labeling (DOL) than biomolecules without spacers. As an example, assume there is antibody that has been labeled with a fluorescent dye separately with and without a spacer. On an equivalent DOL basis, the antibody labeled with the dye that also has spacers bound to it may exhibit an enhancement in fluorescence of between 1.5 and 3.5 times, where 1 would present the same level of fluorescence for both antibodies. The point being that the amount of fluorescent signal on a per dye molecule basis increases for biomolecules bound to both dye and spacer.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, and other targeting carrier molecules.

The incubation temperatures used in the methods described herein can be room temperature, ambient temperature, or temperatures above room temperature, such as, by way of example only, at least about 26° C., 27° C., 28° C., 29° C., 30° C., 40° C., 50° C., 60° C., 70° C., 80° C., even as high as 90° C., 95° C., 96 C, 97°, 98° C., 99° C. or 100° C. The first incubation temperature and the second incubation temperature used in the methods described herein can be the same or different. In some embodiments, the first incubation temperature is between 20° C. and 80° C., between 25° C. and 30° C., and/or at ambient or room temperature. In some embodiments, the second incubation temperature is between 20° C. and 80° C., between 65° C. and 75° C., and/or at approximately 70° C. In other embodiments, the second incubation temperature is at ambient or room temperature.

The incubation times used in the methods described herein include, but are not limited to, for at least 30 seconds, at least 1 minute, at least 2 minutes, 3 minutes, 4 minutes, 5 minutes, 6 minutes, 7 minutes, 8 minutes, 9 minutes, 10 minutes, 15 minutes, 20 minutes, 30 minutes, 40 minutes, 50 minutes, at least 1 hour, or any range herein. The first incubation time and the second incubation time used in the methods described herein can be the same or different. In one embodiment, the first incubation time is 0 to 60 minutes, 5 to 10 minutes, and/or at 5 to 10 minutes at room temperature. In some embodiments, the second incubation time is 0 to 20 minutes and/or approximately 10 minutes. In specific instances, the second incubation time is approximately 10 minutes at approximately 70° C. In other embodiments, the first incubation time is 1 to 3 hours at 25° C., the second incubation time is overnight at 25° C. and the third incubation time is 2 to 3 hours at 37° C.

Conjugates of polymers, including biopolymers and other higher molecular weight polymers are typically prepared by means well recognized in the art (for example, Brinkley et al., *Bioconjugate Chem.*, 3:2 (1992)). In these embodiments, a single type of reactive site may be available, as is typical for polysaccharides) or multiple types of reactive sites (e.g., amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually the case that the reagents be kept as concentrated as practical so as to obtain adequate rates of conjugation.

In certain embodiments of the methods described herein a control protein or proteins may be labeled to monitor the effectiveness of labeling, either in a parallel reaction or, if readily resolvable from the protein desired to be labeled, by inclusion in the same reaction.

In certain embodiments of the methods described herein, the proteins of the labeled sample can usefully be resolved in parallel with a series of fluorescent molecular weight standards. Usefully, the standards are spectrally matched to at least one fluorophore used to label the proteins. Such spectral matching can be accomplished, for example, by using tetracysteine-tagged protein standards that are labeled in parallel with the same biarsenical fluorophore used to label the protein sample, or by using standards having a fluorescent moiety that is spectrally matched to the biarsenical fluorophore or other fluorophore used to label the sample proteins. Examples of standards useful in the practice of the present invention include the BENCHMARK™ family of protein standards (Life Technologies Corp., Carlsbad, Calif.) and MARKL2™ Unstained Standard (Life Technologies Corp., Carlsbad, Calif.).

The methods and compositions described herein can also be used to quantitate the amount of fluorescently labeled protein present in a sample. In certain embodiments, the methods described herein further comprise quantitating the amount of fluorescence from the biarsenical fluorophore. In certain embodiments, the methods described herein further comprise quantitating the amount of fluorescence from the amine reactive fluorescent dye. In certain embodiments, the methods described herein further comprise quantitating the amount of fluorescence from the fluorescent moiety from the amine reactive fluorogenic reagent. The quantitation can be done without resolution of the proteins present in the protein sample or after the proteins have been partially or fully resolved, as by electrophoresis, such as PAGE, 2D-PAGE, or IEF or chromatography or combinations thereof.

e. Conjugation of Spacer Molecules to Biomolecule

In some embodiments, the spacer molecule is conjugated to the biomolecule using NHS-ester chemistries are described in the examples herein, other chemistries such as maleimide, pyridyl disulfide and hyrazides, as well as the SITECLICK™ technology involving azide/alkyne may also be used for this conjugation strategy.

In some embodiments, the spacer molecule is conjugated to a biomolecule (e.g., an antibody) at primary lysine side chains present on a protein, such as an antibody.

In some embodiments, the concentration of a protein, protein fragment or other biomolecule labeled using the methods described herein is in the range from about 0.01 mg/mL to about 200 mg/mL (e.g., from about 0.1 mg/mL to about 100 mg/mL, from about 0.1 mg/mL to about 50 mg/mL, from about 0.1 mg/mL to about 10 mg/mL, from about 0.2 mg/mL to about 100 mg/mL, from about 0.2 mg/mL to about 50 mg/mL, from about 0.2 mg/mL to about 10 mg/mL, from about 0.3 mg/mL to about 10 mg/mL, from about 0.4 mg/mL to about 10 mg/mL, from about 0.5 mg/mL to about 10 mg/mL, etc.).

In some embodiments, the dye to protein ratio of the fluorescent label to the antibody is between 1 and 50. In some embodiments, the dye to protein ratio of the fluorescent label to the antibody is between 5 and 30. In some embodiments, the dye to protein ratio of the fluorescent label to the antibody is between 1 and 20.

In some embodiments, the spacer to protein ratio is between 1 and 50. In some embodiments, the spacer agent to protein ratio is between 5 and 30. In some embodiments, the spacer agent to protein ratio is between 1 and 20.

In some embodiments, the spacer agent is added in molar excess to the plurality of fluorescent labels in an amount between 0.1 to 25, between 1 to 15, or between 2.5 to 10 fold. In some embodiments, the spacer agent is in molar excess to the plurality of fluorescent labels in an amount of 2.5 fold. In some embodiments, the spacer agent is in molar excess to the plurality of fluorescent labels in an amount of 5 fold. In some embodiments, the spacer agent is in molar excess to the plurality of fluorescent labels in an amount of 7.5 fold. In some embodiments, the spacer agent is in molar excess to the plurality of fluorescent labels in an amount of 10 fold.

In some embodiments, the spacer agent is conjugated to a nucleic acid molecule. Protocols for conjugating moieties (e.g., fluorescent labels) to nucleic acids are described in the art (see, e.g., Rombouts et al., *Bioconjugate Chem.*, 27:280-207 (2016)). One method for labeling nucleic acid molecules is through the use of the ARES™ ALEXA FLUOR® 488 DNA Labeling Kit (Thermo Fisher, cat. no. A21665). Amine-modified nucleotides may also be used to enable labeling of nucleic acid molecules. For example, 5-aminohexylacrylamido-dUTP (aha-dUTP) and 5-aminohexylacrylamido-dCTP (aha-dCTP) can be used to produce amine-modified DNA by conventional enzymatic incorporation methods such as reverse transcription, nick translation, random primed labeling or PCR. The amine-modified DNA can then be labeled with any amine-reactive dye or hapten. This two-step technique consistently produces a uniform and high degree of DNA labeling that is difficult to obtain by other methods.

One method for achieving a high DOL, with spatially separated fluorescent labels, is set out in FIG. 18. FIG. 18 shows the preparation of fluorescently labeled branched PEG molecules and the attachment of the resulting PEG molecules (direct spacers) to an antibody, where the PEG molecules are covalently linked to the antibody by CLICK-iT™ reactions (see Example 7).

The PEG molecules shown in FIG. 18 are each covalently linked to seven fluorescent labels. Further, the fluorescent labels may be attached to the individual PEG molecules in a manner such that the labels have a specified "brush" length with respect to the labeled molecule. "Brush length" refers to the extended length of chemical groups that attach a fluorescent labels to a labeled molecule. As an example, assuming that the average monomer length in a PEG molecule is about 3.5 angstroms, when n=1 in FIG. 18, then the brush length of the fluorescent labels would range from about 5 to about 10 angstroms. In many instances, n in FIG. 18 will not be 1. Further, PEG molecules typically vary in size and are described based upon an average molecular weight. Thus, using the PEG molecules set out in FIG. 18 for purposes of illustration, a population of PEG molecules with an average weight of 10,000 would have an n of around 30. Also, a population of PEG molecules with an average weight of 40,000 would have an n of around 120. In view of the fact that both the arm of a branched PEG molecule that links this molecule to the labeled molecule and the other arm all have a repeating region, the brush lengths may range from about 15 angstroms to about 800 angstroms (e.g., from about 25 to about 800, from about 150 to about 800, from about 450 to about 800, from about 600 to about 800, from about 65 to about 800, from about 25 to about 700, from about 40 to about 700, from about 28 to about 600, from about 28 to about 500, from about 70 to about 700, etc.). Thus, the invention includes compositions and methods for producing and using molecules that are covalently linked to at least one fluorescent label, wherein the fluorescent label(s) has a brush length of from about 22 angstroms to about 800 angstroms.

As an alternative, compositions of the invention may be described by the number of covalent bonds between the molecules and the fluorescent label to which they are linked. Again using the branched PEG molecule set out in FIG. 18 for purposes of illustration, the number of intervening covalent bonds would be between about 24 and about 32, depending on where the fluorescent label is attached to the branched PEG molecule. The invention includes compositions and methods for producing and using molecules that are covalently linked to at least one fluorescent label, wherein the fluorescent label(s) are connected to the molecule by from about 16 to about 800 (e.g., from about 16 to about 700, from about 32 to about 800, from about 60 to about 800, from about 100 to about 800, from about 150 to about 800, from about 200 to about 800, from about 250 to about 800, from about 250 to about 700, from about 250 to about 650, from about 250 to about 600, from about 350 to about 800, etc.) intervening covalent bonds.

The invention also relates, in part, to spacing out of multiple fluorescent labels attached to the same location on individual labeled molecules. Similar to what is set out above with respect to the separation of fluorescent labels from labeled molecules, multiple fluorescent labels attached to the same location on individual labeled molecules may be separated from each other by distances of from about 15 angstroms to about 800 angstroms (including the ranges set out above) and/or by from about 16 to about 800 (including the ranges set out above) intervening covalent bonds.

As noted herein, aspects of the invention relate to the spacing of fluorescent labels. Table 9 shows estimated characteristics of a series of branched PEG molecules. It should be understood that these PEG molecules, as well as other molecules, exist in multiple formats at different times. For example, arms of a branch PEG molecule may be fully extended (brush) or fully coiled (mushroom), as well as effectively all conformations in between. Further, each arm may be in a different state of extension or coiling independent of other arms at any one time. Thus, in Table 9, the term "brush" refers to fully extended PEG arms and the term "mushroom" refers to fully coiled PEG arms. The mushroom state is modeled upon a very large Flory radius (distance between adjacent PEG arms) of 80 angstroms to get the smallest number.

F-F distances in Table 9 are distances between two fluorophores on the termini of different arms, assuming all of the fluorophores are equidistant from each other. The maximum distance is double the arm length. Further, the nearest neighbor value assumes tetrahedral arrangement for 4 arms and spherical/cubic for 8 arms. Of course, the actual value of F-F distances at any one time point will typically be somewhere in between the brush distances and the mushroom distance.

TABLE 9

Branched PEG Arm Length (Estimated Fluorophore to Fluorophore (F-F) Distance)

| MW | Arms | Arm MW | EG/ Arm* | Arm Length (Å) (BAL)** | Arm Length (Å) (MAL)** | Max F-F Dist. (Å) BAL (3) | F-F Nearest Neighbor Dist. (Å), Brush (3) | Max F-F Dist. (Å), MAL (4) | F-F Nearest Neighbor Dist. (Å), MAL (4) |
|---|---|---|---|---|---|---|---|---|---|
| 10000 | 4 | 2500 | 60 | 208 | 26 | 417 | 340 | 52 | 42 |
| 10000 | 8 | 1250 | 30 | 104 | 13 | 208 | 120 | 26 | 15 |
| 20000 | 8 | 2500 | 60 | 208 | 26 | 417 | 241 | 52 | 30 |
| 40000 | 8 | 5000 | 119 | 417 | 52 | 833 | 481 | 104 | 60 |

*EG/Arm = Arm MW/EG MW ~ Arm MW/42 (MW = Molecule Weight)
**Brush Arm Length (BAL) = EG/Arm * monomer length ~ EG/Arm * 3.5
**Mushroom Arm Length (MAL), as determined by the equation below (L = . . . )
(3) Fully extended, end of arms equidistant from each other (Dist. = Distance)
(4) Fully coiled, end of arms equidistant from each other
These calculations are based upon the JenKem following products: 4ARM-NH2HCl and 8ARM-NH2HCl $$L = \frac{Na^{5/3}}{D^{2/3}}$$

a = 3.25 nm (3.5 A)
N = 30, 60, 120
D = 80 A

Dextrans are another suitable material for connecting fluorescent labels to molecules. Dextrans are hydrophilic polysaccharides characterized by their moderate to high molecular weight, good water solubility and low toxicity. Dextrans tend to be biologically inert due to their uncommon poly-($\alpha$-D-1,6-glucose) linkages. These linkages render them resistant to cleavage by most endogenous cellular glycosidases. They also usually have low immunogenicity and are generally branched molecules.

Dextrans are commercially available with nominal molecular weights (MW) varying between 3000 daltons and 2,000,000 daltons. Dextrans suitable for use in the practice of the invention may be of any number of different molecule weights, including 3000, 10,000, 40,000, 70,000, 500,000, and 2,000,000 daltons (e.g., from about 4,000 to about 150,000, from about 6,000 to about 150,000, from about 8,000 to about 150,000, from about 15,000 to about 150,000, from about 10,000 to about 80,000, from about 12,000 to about 70,000, etc.).

Dextrans usually have a degree of substitution (e.g., a DOL) of 0.2 to 2 of dye molecules per dextran molecule for dextrans in the 10,000 MW range. Further, dextrans typically contain 0.2-0.7 dyes per dextran in the 3000 MW range, 0.4-2 dyes per dextran in the 10,000 MW range, 1-4 dyes in the 40,000 MW range and 2-6 dyes in the 70,000

MW range. Thus, dextrans, as well as other labeled polymers, used in the practice of the invention may have a DOL ranging from about 0.03 to 0.3 fluorescent labels per 1,000 MW (e.g., from about 0.03 to about 0.25, from about 0.08 to about 0.3, from about 0.09 to about 0.3, from about 0.1 to about 0.3, from about 0.05 to about 0.2, from about 0.07 to about 0.25, etc. per 1,000 MW).

Dextrans, as well as other polymers, may be labeled in a number of ways. For example, fluorescently labeled dextrans may be prepared by the reaction of a water-soluble amino dextran with a fluorescent label having a succinimidyl ester group. Fluorescently labelled dextran may also be prepared by the reaction of a native dextran with an isothiocyanate derivative of a fluorescent label such as FITC. Where appropriate, once the fluorescent label has been added, unreacted amines on the dextran may be capped to yield a neutral or charged dextran (i.e., negatively or positively charged). Further, even where capping is not performed, charged fluorescent labels may be used which can render dextrans anionic or cationic.

Another type of polysaccharide that can be useful in the practice of the invention is amylose. Amylose is a linear polysaccharide composed of α-D-glucose units linked by α-1,4-glycosidic bonds. Due to hydrogen bonding, amylose tends to form spiral structures containing six glucose units per turn. Molecules of this type provide structure regularity that can be used space out fluorescent labels in consciously designed manner. The invention thus includes compositions, as well as methods for making and using such compositions, with fairly static structural features that may be employed for maintaining a uniform distance between fluorescent labels. In many instances, the distance between two fluorescent labels associated with such a molecule in a manner and under conditions that would result in two fluorescent labels would not vary in distance from each other by more than 30% (e.g., from about 5% to about 30%, from about 10% to about 30%, from about 15% to about 30%, from about 20% to about 30%, from about 10% to about 20%, etc.).

Polypeptides may also be used in the practice of the invention. One exemplary such molecule is the branched polylysine molecule shown in FIG. 21. This molecule may be made according to methods set out in U.S. Patent Publication No. 2010/0278750. A number of "R groups" are shown in FIG. 21, representing locations where fluorescent labels may be attached. In such a molecule the R groups may be the same or different (e.g., $R_1$ and $R_2$). Further, when a number of R groups are the same, these groups may act as fluorescent label attachments points where the R groups are not labeled to completion.

By way of example, FIG. 21 shows a polymer with 33 R groups, 32 $R_1$ groups and 1 $R_2$ group. Assume that all of the R groups are of the same type. These R groups may be partially fluorescently labeled in a semi-random manner. By this is meant that conditions may be provided such that only a percentage of the R group receive a fluorescent label. Further, the labeling would be semi-random because some R group, due to their position in the polymer, would be more prone to receive a fluorescent label. Thus, the invention includes the design of fluorescently labeled polymers where the positioning and DOL are adjusted for a desired fluorescent effect. In some instances, the average number of available attachment site on a per polymer basis that receive labels is in the range of 10% to 90% (e.g., from about 10% to about 85%, from about 15% to about 85%, from about 20% to about 85%, from about 20% to about 75%, from about 30% to about 75%, from about 30% to about 80%, from about 40% to about 80%, etc.).

As noted above, FIG. 21 shows a polymer with $R_1$ and $R_2$ groups. If "directional" linkage of the polymer to a biomolecule (e.g., an antibody) is desired, the $R_2$ group may be different from the $R_1$ groups. If the R groups are the same, then attached would be "non-directional" in the sense that any R group in a suitable location on the polymer could serve as a conjugation point to the biomolecule. Of course, conditions would be adjusted to achieve a high level of fluorescence, while maintaining a high level of biological activity for the biomolecule (e.g., antigen binding).

Maximization of biomolecule fluorescence may be partially independent of the number of fluorescent labels on the biomolecule of interest. Assume for example that there are seven fluorescent labels on a particular antibody, when labeled under a first set of conditions, and ten fluorescent labels on the same antibody, when labeled under the second set of conditions. Further assume that the amount of total fluorescence of the antibody labeled under the first set of conditions is greater than the amount of total fluorescence of the antibody labeled under the second set of conditions. In this instance, fewer fluorescent labels resulted in more fluorescence. Thus, other factors being equal (e.g., functional activity of the biomolecule), the first set of conditions would be preferred over the second set of conditions.

Any number of linking groups may be used to attach fluorescent labels to biomolecules. These attachments may be non-covalent or covalent. Further, non-covalent or covalent can refer to one or all of (1) the linking of the fluorescent label to a polymer, (2) the linking of the polymer to a core (when present), and/or (3) the linking of the polymer or the core, when present, to the biomolecule.

In many instances, polymers (with or without cores), as well as other types of spacers set out herein, may serve the function of increasing the fluorescent intensity of fluorescent labels attached to a biomolecule.

One category of molecules that are useful in the practice of the invention are referred to as star polymers (see Ren et al., *Star Polymers, Chemical Reviews,* 116:6743-6836 (2016)). Star polymers are multi-arm molecules that contain a core and a series of linear polymers (referred to as "arms"). These arms typically contain terminal functionality to facilitate attachment of other molecules. Star polymers may be classified as homo-arm (containing arms of only one composition) or mikto-arm (containing arms of more than one composition, molecular weight or terminal functionality). Synthesis of star polymers is typically carried out using either core first, arm first or grafting onto approaches.

The core effectively serves as a branching point for the arms. Any number of molecules can serve as cores for compositions of the invention. Examples of suitable cores include oligoglycerols (e.g. hexaglycerol), oligoerythritols (e.g., pentaerythritol, dipentaerythritol, tripentaerythritol), sorbitol, trimethylolpropane, silanes (e.g. 1,2-bis(methylsilyl)ethane), adamantanes, PAMAM (1-, 2-, and 3-generation (G-1-3) poly(amidamine)) dendrimers, polyethylene imine (PEI) branched polymers, peptides (e.g., polylysine, polyaspartic acid, etc.).

The core may already have functional groups for initiation of polymerization or linking onto of arms or, as shown in FIG. 20, may require chemical modification in order to facilitate the attachment of arms.

Using hexaglycerol as an example, this compound is available commercially and may be used in the core first synthesis of star-shaped PEG polymers. StarPEGs with hexaglycerol cores may be used for the controlled release of drugs and for wound sealing. StarPEGs with hexaglycerol cores may be produced by the controlled polymerization of ethylene oxide from the hexaglycerol core. In this instance, the core is hexaglycerol and the arms are polyethylene glycol.

The arms may be composed any number of linear polymers and will typically function as attachment points for fluorescent labels and for spacing these labels out from each other, as well as spacing the labels out from other fluorescent labels attached to the same labeled molecule (e.g., a biomolecule). Examples of suitable arms include polyethylene glycol, poly(vinyl pyrrolidone), polyglycerol, and polyvinyl alcohol, zwitterionic polymers (e.g. polysuflo betaines) as well as water soluble polymers. In many instances, polymers suitable for use in the invention will be non-charged.

One area of antibodies that is particularly useful for the attachment of fluorescent labels, when present, is the Fc (fragment crystallizable) region. The Fc region is at the far end of antibodies with respect to the antigen bind site(s). This region of the antibody interacts with cell surface receptors called Fc receptors and proteins of the complement system. Typically, attachment of chemical entities at or near the Fc region has little impact on antigen binding by the antibody. However, interference with antigen binding events tends to increase with the size of chemical entities attached to the antibody. Further, large attached chemical entities tend to interfere with each other, due to steric hindrance, with respect to the ability to attach to a biomolecule. Thus, a series of factors may need to be balanced in order to produce a biomolecule (e.g., an antibody) with both a high level of fluorescence and a high level of functional activity (e.g., antigen binding ability). Some of these factors are as follows: (1) Size of the biomolecule, (2) location of attachment points on the biomolecule for fluorescent labeling, and (3) the size(s) and three dimensional structures of the fluorescent labeled molecules being attached to the biomolecules.

With respect to antibodies, the invention includes antibodies that contain one or more of the following features:

Fluorescently labeled polymers bound (e.g., covalently bound) at from an average 2 to 10 different locations on the antibody molecules.

An average of from 3 to 80 fluorescent labels attached to each of the antibody molecules.

Antigen binding affinity ($K_D$) of the fluorescently labeled antibody molecule is decreased by no more than two (e.g., from about 0.5 to about 2.0, from about 1.0 to about 2.0, from about 0.5 to about 1.5, from about 0.75 to about 1.5, etc.) orders of magnitude as compared to the unlabeled form of the antibody.

The average amount of fluorescent emission on a per fluorescent label basis bound to the antibody molecules is at least 60% (e.g., from about 60% to about 98%, from about 70% to about 98%, from about 80% to about 98%, from about 85% to about 98%, from about 80% to about 93%, etc.) that of the free fluorescent label.

f. Biomolecule/Fluorescent Label/Spacer Combinations

The invention is based, in part, on combinations of three components: Biomolecules, fluorescent labels, and spacers. With respect to proteins (e.g., antibodies), groups that may be used as attachments sites for fluorescent labels and spacers may not always be accessible for attachment, especially when the protein has not be denatured. Further, in many instances, it will be desirable to maintain proteins in undenatured form.

Enhancement in fluorescent emission have been found to relate to various ratios of fluorescent labels and spacers used to label biomolecules (e.g., antibodies). Further, each biomolecule has the potential for requiring different ratios of components in the conjugation process to yield specified enhanced fluorescence levels. This may be due to different structure (e.g., primary, secondary, tertiary and quaternary structure) of biomolecules, such as antibodies, as well as characteristics of the particular fluorescent label and the particular spacer.

In some instances, ratios may be based upon the respective weights of components. In other instances, ratios may be based upon molar ratios. A number of the figures and example of this application relate to molar ratios. In some instances (e.g., where the biomolecule is large and with a large number of conjugation sites), the use of component weights may be more suitable.

For antibodies, as well as other biomolecules, the following ratios of biomolecule to fluorescent label to spacer used in the conjugation process may vary greatly but in most instances the amount of biomolecule will be lower than the amount of both fluorescent label and spacer.

Further, the density and/or spacing of conjugation sites on a biomolecule is one factor that will often determine the optimum ratio of fluorescent label to spacer. This is so because, assuming enhanced fluorescence is due to reduced quenching, the lower the total or regional density of conjugations sites, the lower the amount of quenching would be expected to be. In any event, ratios of biomolecule to fluorescent label to spacer that may be used can be described as follows: $B_1$: $FL_{2-30}$: $S_{2-20}$, where B is biomolecule, FL is fluorescent label and S is spacer. Specific ranges of ratios that may be used in the practice of the invention include ratios that fall within 1:2-25:2-20 (e.g., from about 1:2:2 to about 1:25:20, from about 1:5:2 to about 1:25:5, from about 1:10:2 to about 1:25:5, from about 1:5:2 to about 1:15:10, from about 1:10:5 to about 1:25:20, from about 1:10:5 to about 1:15:20, from about 1:10:5 to about 1:20:20, etc.), wherein the first number is the amount (e.g., moles) of biomolecule, the second number is the amount of fluorescent label, and the third number is the amount of spacer.

In some instances, fluorescent label and spacer concentrations used for conjugation will be such that available attachments sites on biomolecules will be effectively saturated (e.g., at least 95% of available attachments sites will have bound thereto either a fluorescent label or a spacer). In such instances, the fluorescent label and spacer ratio may be a determining factor in the level for fluorescent enhancement. In many instances the ratio of fluorescent label to spacer will be between 10:1 to 10:50 (e.g., from about 10:1 to about 10:25, from about 10:1 to about 10:10, from about 10:1 to about 10:5, from about 10:5 to about 10:50, from about 10:5 to about 10:20, from about 10:3 to about 10:30, from about 10:5 to about 10:30, from about 10:10 to about 10:25, etc.).

Spacers and dyes may be conjugated to a biomolecule at the same time or sequentially, with either the spacer or the dye being conjugated to the biomolecule first. In many instances, when the spacer and dye connect to the biomolecule at the same loci, they will be conjugated to the biomolecule at the same time. However, sequential conjugation could be used when the first conjugation reaction (e.g., of the spacer) is done under conditions where the binding sites are the biomolecule are not saturated, thus leaving binding sites available for a second conjugation reaction (e.g., of the dye).

g. Buffers

In some embodiments, the composition of the invention comprises one or more spacer, one or more fluorescent label in a buffer. Any of the fluorescent and spacer molecules disclosed herein may be used together with any buffer known in the art.

In some embodiments, the compositions disclosed herein comprise any suitable buffer for a molecular biology application.

In some embodiments, the buffer is a suitable storage buffer (e.g., borate buffer, phosphate buffer or carbonate buffer).

In some embodiments, the buffer is suitable for buffering a detectable biomolecule, as disclosed herein, during use in a detection assay.

Methods

The instant invention has useful applications in basic research, high-throughput screening, immunohistochemistry, fluorescence in situ hybridization (FISH), microarray technology, diagnostics, and medical therapeutics. The invention can be used in a variety of assay formats for diagnostic applications in the disciplines of microbiology, immunology, hematology and blood transfusion, tissue pathology, forensic pathology, and veterinary pathology.

In some embodiments, the compositions described herein can be used in any molecular biology application wherein fluorescently labeled molecules are detected. For example, the detectable biomolecules, as disclosed herein, can be used in Western blotting, ELISA, flow cytometry, flow cytometry and applications involving FRET. The detectable biomolecules, as disclosed herein, can also be used in fluorescent immunohistochemistry (IHC), fluorescent immunocytochemistry (ICC), and in vivo imaging applications.

In some embodiments, a method for determining the presence of a desired target in a biological sample is encompassed, the method comprising: a) contacting the biological sample with a composition comprising one or more fluorescent label, and one or more spacer molecules, wherein the spacer and fluorescent label are conjugated to the biomolecule but not to each other, b) detecting fluorescence emitted by the plurality of fluorescent labels; and c) determining the presence of the desired target in the biological sample when fluorescence emitted by the plurality of fluorescent labels is detected. In some embodiments, the biological sample comprises cell lysate. In some embodiments, the biological sample comprises intact cells. In some embodiments, the biological sample comprises a tissues sample. Further such tissue samples may be fixed. Further, compositions of the invention may be used for applications such as immunohistochemistry. In some embodiments, the biological sample comprises isolated protein. In some embodiments, the biological sample comprises recombinant protein. In some embodiments, the biological sample is immobilized on a solid support. In some embodiments, the biological sample comprises intact cells in fluid. In some embodiments, the biological sample is a live animal. In some embodiments, the live animal is a mammal. In some instances, the sample comprises tissues such as liver, lung, muscle and skin.

In some embodiments, disclosed herein is a method for imaging a target antigen in a living body, wherein the method comprises; a) providing an antibody conjugated to a plurality of fluorescent labels and a spacer agent, as disclosed herein, that binds to the target antigen; b) introducing the antibody into the body to form a contacted body; c) illuminating the contacted body with an appropriate wavelength to form an illuminated body; and d) observing the illuminated body wherein the target antigen is imaged. In some embodiments, these antibodies or other targeted proteins or peptides specific for a target or antigen in a living body that has been conjugated with a fluorescent dye(s) having an excitation wavelength compatible with in vivo imaging, typically about 580 nm to about 800 nm. The target specific dye conjugates travel relatively freely within the circulating blood until their preferential sequestration occurs at a target pathological or non-pathological tissue sites such as a diseased or injury tissue sites.

h. Kits

The compositions of the invention may be incorporated into kits that facilitate the practice of various assays. The kits may be packaged with the composition in a dry form or with the composition in solution. The kits may optionally further include one or more buffering agents, typically present as an aqueous solution, sample preparation reagents, additional detection reagents, organic solvent, other fluorescent detection probes, standards, microspheres, specific cell lines, antibodies and/or instructions for carrying out an assay. Additional optional agents include components for testing of other cell functions in conjunction with the compound.

In some embodiments, the kits comprise a biomolecule, spacer agent, and a fluorescent label, as disclosed herein. In some embodiments, the kit further comprises a buffer. In some embodiments, the biomolecule is already conjugated to the spacer agent and the fluorescent label. In some embodiments, the kit may comprise a polymer conjugated to fluorescent labels and a reactive group as a bioconjugation kit.

Kits of the invention may further contain reagents used to prepare fluorescently labeled biomolecules (e.g., antibodies). Exemplary reagents include one or more of the following: fluorescent dyes, spacers that are either prelabled of labeled according to instructions provided in the kits, and compounds that may be used to conjugate (1) spacers to biomolecules and/or (2) fluorescent lables to biomolecules.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

EXAMPLES

The following examples are provided to illustrate certain disclosed embodiments and are not to be construed as limiting the scope of this disclosure in any way.

Example 1: Fluorescent Western Blotting Methods a.) Antibody Labeling Using NHS Activated Fluorescent Dyes and Sulfo NHS-Acetate/NHS-Acetate and NHS-MS $(PEG)_4$, NHS-MS$(PEG)_8$ and NHS-MS$(PEG)_{12}$ NHS activated fluorescent dyes, such as DyLight™ 650-4×PEG, were reconstituted in dimethylformamide (DMF) at 10 mg/ml. NHS-Acetate was prepared fresh in dimethyl formamide (DMF) at 1 mg/ml. NHS-MS$(PEG)_4$ (Cat. no. 22341 (Thermo Fisher Scientific), NHS-MS$(PEG)_8$ (cat. no.

22509 (Thermo Fisher Scientific), NHS-MS(PEG)$_{12}$ (cat. no. 22686 (Thermo Fisher Scientific), were reconstituted in DMF at 100 mg/ml. The PEG Reagents were further diluted to 1 mg/ml in DMF just prior to use. 1 mg of Goat Anti-Mouse (GAM) and Goat Anti-Rabbit (GAR) antibody at 7-10 mg/ml in Borate Buffer 50 mM (cat. no. 28384 (Thermo Fisher Scientific), pH 8.5 were labeled with each fluorescent dye, or a mixture of each fluorescent dye and a spacer selected from NHS-Acetate, NHS-MS(PEG)$_4$, NHS-MS(PEG)$_8$ or NHS-MS(PEG)$_{12}$ at various molar excesses. The labeling reactions were incubated for approximately 1 hour at room temperature (RT). The NHS activated dye and the NHS activated spacer agents were combined before addition to the antibody so that both reactions were concurrent, allowing for a random spacing of the dye substitution and of the spacers. 100 mM MES Buffer at pH 4.7 was added to each sample to lower the pH from 8.5 to approximately 7.2. At this point the concentration of the conjugates was adjusted down to approximately 6 mg/ml to accommodate the final dilution in the storage buffer. The free dye was removed using the Dye Removal Resin (Thermo Fisher Scientific, cat. no. 22858) and 5 μm Harvard columns (Harvard Apparatus, cat. no. 74-3820). 0.2 ml of the 50% purification resin slurry was used per mg of protein. The conjugates were diluted 1:50 with 0.1M Sodium Phosphate Buffer, pH 7.2 (PBS) and scanned using the UV Cary Spectrophotometer. OD scans (252 nm to 900 nm) were used to determine concentrations of conjugates and calculate mole dye/mole protein ratios (D/P). Finally, the conjugates were diluted to 1 mg/ml in STABILZYME® NOBLE Storage Buffer (Surmodics, cat. no. SZ04) for long term storage.

Serially diluted cell lysates (500 ng to 2 ng) were combined with SDS-PAGE sample buffer. The samples were heated for five minutes at 95° C., and loaded onto Thermo Fisher Scientific Tris Glycine SDS-PAGE gels (Novex Gels, 4-20%, 10-well, cat. no. WT4202BX10). Gels were electrophoresed according to manufacturer's instructions and then transferred to nitrocellulose membranes using a semi-dry transfer method. The membranes were blocked for thirty minutes with SEA BLOCK Blocking Buffer (Thermo Fisher Scientific, cat. no. 0037527). The primary antibodies were prepared to a final concentration of 0.1 to 2.5 μg/ml in Sea Block Blocking Buffer. The blots were incubated with the antibody prepared in the Sea Block Blocking Buffer for one hour with shaking at room temperature (RT). The antibody solution was decanted and the membranes were washed two times for ten minutes in 10 mM Tris, 150 mM NaCl, 0.05% Tween-20, pH 7.2 (TBST). The fluorescently labeled secondary antibody conjugates were diluted to a final concentration of 20 to 1000 ng/mL in SEA BLOCK Blocking Buffer. The washed membrane was incubated with the relevant secondary antibody conjugate with agitation for 30 to 60 minutes. The buffer was decanted and the membranes were washed six times for five minutes with TBST. The membranes were imaged using a compatible fluorescent imager.

Results are shown in FIG. 8 for an experiment testing the effect of addition of NHS Acetate (2.5×, 5× and 10×) and MS(PEG)$_4$ (3.75×) spacer to a GAM secondary antibody conjugated to DYLIGHT™ 488 at 5×-20× molar excess in a western blotting assay. A431 cell lysate was diluted 3-fold from 1 μl g/well. The primary antibody rabbit used was anti-Hsp90 diluted 1/5000 from 1 mg/ml. All DYLIGHT™ secondary antibodies were diluted 1/5000 from 1 mg/ml stock. In a Western blot application, there is noticeable increase of fluorescent intensity over the base conjugate (made without the spacer) at each dye molar excess from 7.5× to 20× for DYLIGHT™ 488-GAR conjugated with the addition of NHS Acetate or MS(PEG)$_4$.

Results demonstrating the effect of addition of NHS Acetate (5×) or MS(PEG)$_4$ (5×) spacer to a GAM secondary antibody conjugated to DYLIGHT™ 650-4×PEG (at 7.5× Dye) in a Western blot assay are shown in FIG. 9. HeLa cell lysate was diluted 4-fold from 0.5 μg/well. Primary antibody mouse anti-PDI was diluted to 1/5000 of 1 mg/ml. All DYLIGHT™ secondary antibodies were diluted to 1/5000 of 1 mg/ml stock. NHS acetate added at 5× molar excess to GAM-DYLIGHT™ 650-4×PEG-7.5× conjugation improved intensity by 1.5-fold. NHS acetate added at 3.75× molar excess to GAM-DYLIGHT™ 650-4×PEG-7.5× conjugation improved intensity by 1.4-fold.

Results demonstrating the effect of addition of NHS Acetate (2.5×, 5×) and MS(PEG)$_4$ spacer to a GAR-DYLIGHT™ 800-4×PEG secondary antibody in a Western blot assay are shown in FIG. 10 and Table 10. A431 cell lysate was serially diluted 1:1. Primary antibodies rabbit anti-Hsp90 and anti-Cyclophilin B were diluted 1/5000. All DYLIGHT™ secondary antibodies were diluted to 1/20,000 of 1 mg/ml stock. The addition of MS(PEG)$_4$ (3.75× and 5×) and NHS Acetate (2.5-5×) significantly enhanced the fluorescence intensity and sensitivity of base DYLIGHT™ 800-4×PEG conjugate by 20-100% at different molar excesses of the dye in this Western blotting application.

TABLE 10

Effect of ± NHS Acetate (2.5X, 5X) or MS(PEG)$_4$ (5X) on GAR-DYLIGHT ™ 800-4xPEG in Western Blot Assays.

| Fold Improvement (WB) | NA | +2.5X NHS Acetate | +5X NHS Acetate | +5X NHS MS(PEG)$_4$ |
|---|---|---|---|---|
| GAR-DYLIGHT ™ 800-4xPEG_5x | 1.0 | 1.4 | 1.2 | 1.8 |
| GAR-DYLIGHT ™ 800-4xPEG_7.5x | 1.0 | 1.5 | 1.2 | 1.7 |
| GAR-DYLIGHT ™ 800-4xPEG_10x | 1.0 | 1.7 | 1.5 | 1.9 |
| GAR-DYLIGHT ™ 800-4xPEG_15x | 1.0 | 1.9 | 1.5 | 2.0 |

NA = No Addition

Results demonstrating the effect of addition of NHS Acetate (2.5×, 5× and 10×) and MS(PEG)$_4$ (5×) and MS(PEG)$_8$ (5×) spacer to a GAM-DYLIGHT™ 550-2×PEG conjugate (at 12.5× molar excess of dye) in a western blotting assay are shown in FIG. 11. HeLa cell lysate was diluted 4-fold from 0.5 μg/well and was stained with anti-PDI primary antibody diluted to 1/5000 of 1 mg/ml. All DYLIGHT™ secondary antibodies were diluted to 1/5000 of 1 mg/ml stock. This experiment showed that the addition of MS(PEG)$_4$ (5×) and NHS acetate (2.5× and 5×) significantly enhanced the fluorescence intensity and sensitivity of base DYLIGHT™ 550-2×PEG conjugates by at least by 2-fold in a Western Blot assay. Conjugates prepared with longer chain MS(PEG)$_8$ did not show significant improvement over the base conjugate in this experiment.

Results demonstrating the effect of addition of NHS Acetate (2.5×, 5×) and MS(PEG)$_4$ (5×) spacer to GAM-DYLIGHT™ 680-4×PEG-GAR (at 10× molar excess of dye). are shown in FIG. 12. HeLa cell lysate was diluted 4-fold from 0.5 μg/well and anti-PDI primary antibody was diluted to 1/5000 of 1 mg/ml. All DYLIGHT™ 680-4×PEG-GAR secondary antibodies were diluted to 1/20000 of 1 mg/ml stock. This experiment shows that that the addition of MS(PEG)$_4$ (5×) and NHS acetate (2.5× and 5×) significantly enhanced the fluorescence intensity and sensitivity of base DyLight™ 680-4×PEG conjugate by 3 to 4-fold in a Western blotting assay.

Example 2: Dot Blot Assays

Serial dilutions (1:1) Mouse or Rabbit IgG were made from chosen stock concentration. The dilutions were placed in a 96-well plate from highest to lowest using a 20 μL 12-channel multi pipette. 1 or 24 of the 11 serial dilutions was carefully spotted onto Nitrocellulose membranes. The membranes were allowed to dry overnight and then blocked with 2% BSA blocking buffer in TBST. The membranes were incubated with agitation for one hour at room temperature. The blocking solution was decanted from the container. The secondary antibody conjugates were diluted in TBS or blocking buffer. Secondary antibody conjugate dilutions varied depending on the conjugated label: 1:5,000 (DyLight™ 488 and 550-2×PEG conjugates); 1:10,000 (DyLight™ 650-4×PEG conjugates); and 1:20,000 (DyLight™ 680-4×PEG and DyLight™ 800-4×PEG conjugates). The membranes were incubated with the relevant secondary antibody conjugates with agitation for 30 to 60 minutes. The membranes were washed five times for five minutes with TBST buffer. The membranes were imaged with a suitable imager, for example, ChemiDoc MP (488, 550, 650, 680 nm) and LiCOR Odyssey CLx (650, 680, 800 nm).

Results depicted in FIG. 3 and Table 11 show the effect of NHS acetate (2.5×, 5× and 10×) and MS(PEG)$_4$ (3.75×) spacer to GAM-DyLight™ 488 (at 5×-20× molar excess of dye) in a dot blot assay. In dot blot applications, the DyLight™ 488-GAM conjugates made with the addition of NHS Acetate and MS(PEG)$_4$ resulted in definite improvement in fluorescent intensity ranging from 1.2 to 1.8-fold over the base conjugate (made without the spacer) at the various dye molar excesses from 7.5× to 20×.

TABLE 11

Effect of NHS Acetate (2.5X, 5X and 10X) or MS(PEG)$_4$ (3.75x to 10X) addition in the conjugation of GAM-DYLIGHT ™ 488 at 5X-20X molar excess in a Dot Blot.

| FOLD OF IMPROVEMENT | NA | +2.5X NHS Acetate | +5X NHS Acetate | +10X NHS Acetate | +3.75X MS(PEG)$_4$ | +5X MS(PEG)$_4$ | +10X MS(PEG)$_4$ |
|---|---|---|---|---|---|---|---|
| DYLIGHT ™ 488_5x | 1.0 | 1.5 | 1.1 | | 0.3 | 1.0 | 0.6 |
| DYLIGHT ™ 488_7.5x | 1.0 | 1.2 | 1.6 | | 1.8 | 1.0 | 1.3 |
| DYLIGHT ™ 488_10x | 1.0 | 1.6 | 1.3 | | 1.3 | 1.3 | 0.8 |
| DYLIGHT ™ 488_15x | 1.0 | 1.4 | 1.0 | 0.8 | 1.6 | 1.2 | 1.1 |
| DYLIGHT ™ 488_20x | 1.0 | 1.0 | 0.7 | 06 | 1.5 | 1.3 | 1.0 |

NA = No Addition

Results shown in FIG. 4 and Table 12 demonstrate the effect of addition of NHS acetate (2.5× and 5×) and MS(PEG)$_4$ (3.75×) to GAM-DyLight™ 488 (at 7.5×-20× molar excess of dye) in a dot blot assay. In this experiment, a different secondary antibody source was used. NHS acetate and MS(PEG)$_4$ added to the conjugation mixture provided a significant improvement of signal intensity as compared to the base conjugates at 5×, 15× and 20× dye molar excesses; ranging from 1.2 to 2.6-fold.

TABLE 12

Effect of NHS Acetate (2.5X, 5X and 10X) or MS(PEG)$_4$ (3.75x) addition in the conjugation of GAM-DYLIGHT ™ 488 at 5X-20X molar excess in a Dot Blot Assay.

| FOLD OF IMPROVEMENT | No addition | +2.5X NHS Acetate | +5X NHS Acetate | +3.75X MS(PEG)$_4$ |
|---|---|---|---|---|
| DYLIGHT ™ 488_7.5x | 1.0 | 1.8 | 2.1 | 2.1 |
| DYLIGHT ™ 488_10x | 1.0 | 1.2 | 1.0 | 1.2 |
| DYLIGHT ™ 488_15x | 1.0 | 1.5 | 1.9 | 2.0 |
| DYLIGHT ™ 488_20x | 1.0 | 2.0 | 2.6 | 1.3 |

Results shown in FIG. 5 and Table 13 demonstrate the effect of addition of NHS Acetate (2.5×, 5× and 10×) and MS(PEG)$_4$ (3.75×) to GAM-DyLight™ 550-2×PEG-GAR (at 10×-20× molar excess of dye) in a dot blot assay. Mouse IgG was serially diluted 1:1 from 1000 ng/dot. All DyLight™ 550-2×PEG-GAR secondary antibodies were diluted to 1/5000 of 1 mg/ml stock. NHS acetate and MS(PEG)$_4$ added to the conjugation mix provided an improvement of signal intensity as compared to the base conjugates at each respective dye molar excesses. Improvement ranged from 1.2 to 1.6-fold.

TABLE 13

Effect of the addition of NHS Acetate (2.5X, 5X and 10X) or MS(PEG)4 (3.75X) in the conjugation of GAM-DYLIGHT ™ 550-2xPEG-GAR at 10X-20X molar excess in a Dot Blot Assay

| FOLD OF IMPROVEMENT | No addition | +2.5X NHS Acetate | +5X NHS Acetate | +3.75X MS(PEG)$_4$ |
|---|---|---|---|---|
| GAR-DYLIGHT ™ 550-2xPEG_10x | 1.0 | 1.23 | 1.35 | 1.32 |
| GAR-DYLIGHT ™ 550-2xPEG_12.5x | 1.0 | 0.77 | 0.98 | 0.93 |

TABLE 13-continued

Effect of the addition of NHS Acetate (2.5X, 5X and 10X) or MS(PEG)4 (3.75X) in the conjugation of GAM-DYLIGHT ™ 550-2xPEG-GAR at 10X-20X molar excess in a Dot Blot Assay

| FOLD OF IMPROVEMENT | No addition | +2.5X NHS Acetate | +5X NHS Acetate | +3.75X MS(PEG)$_4$ |
|---|---|---|---|---|
| GAR-DYLIGHT ™ 550-2xPEG_15x | 1.0 | 1.12 | 1.1 | 1.52 |

TABLE 13-continued

Effect of the addition of NHS Acetate (2.5X, 5X and 10X) or MS(PEG)4 (3.75X) in the conjugation of GAM-DYLIGHT™ 550-2xPEG-GAR at 10X-20X molar excess in a Dot Blot Assay

| FOLD OF IMPROVEMENT | No addition | +2.5X NHS Acetate | +5X NHS Acetate | +3.75X MS(PEG)$_4$ |
|---|---|---|---|---|
| GAR-DYLIGHT™ 550-2xPEG_20x | 1.0 | 0.9 | 1.51 | 1.63 |

Results shown in FIG. 6 and Table 14 demonstrate the effect of the addition NHS Acetate (2.5×, 5× and 10×) and MS(PEG)$_4$ (3.75×) to GAM-DYLIGHT™ 650-4×PEG-GAM (at 10×-20× molar excess) in a dot blot assay. Mouse IgG was serially diluted 1:1 from 1000 ng/dot. All DYLIGHT™ 650-4×PEG-GAR secondary antibodies were diluted to 1/10000 of 1 mg/ml stock. Both NHS Acetate and (MS)PEG$_4$ brought significant improvement in sensitivity and signal/background over the initial base conjugates. NHS acetate added at 2.5× molar excess to GAM-DYLIGHT™ 650-4×PEG-15× improved intensity by 1.7-fold. The improvement provided by NHS Acetate showed 1.3-fold better performance than with the conjugate prepared with the highest molar excess of dye (20×). All MS(PEG)$_4$ added to GAM-DYLIGHT™ 650-4×PEG-15× conjugation improved fluorescence intensity by 1.8 to 2.2-fold and performed better than the corresponding highest base conjugate GAM-DYLIGHT™ 650-4×PEG-20×.

TABLE 14

Effect of NHS Acetate (2.5X, 5X and 10X) or MS(PEG)$_4$ (3.75X) addition in the conjugation of GAM-DYLIGHT™ 650-4xPEG-GAM at (10X-20X) in a Dot Blot Assay.

| FOLD OF IMPROVEMENT | NA | + 2.5X NHS Acetate | + 5X NHS Acetate | + 10X NHS Acetate | + 3.75X MS(PEG)$_4$ | + 5X MS(PEG)$_4$ | + 10X MS(PEG)$_4$ |
|---|---|---|---|---|---|---|---|
| GAM-DYLIGHT™ 650-4xPEG_5x | 1.0 | 1.0 | 1.2 | | 1.1 | 1.9 | 1.1 |
| GAM-DYLIGHT™ 650-4xPEG_7.5x | 1.0 | 1.7 | 1.5 | | 1.8 | 1.2 | 1.6 |
| GAM-DYLIGHT™ 650-4xPEG_10x | 1.0 | 1.2 | 2.9 | | 1.8 | 1.3 | 1.5 |
| GAM-DYLIGHT™ 650-4xPEG_15x | 1.0 | 1.6 | 1.5 | 1.0 | 2.2 | 1.0 | 2.2 |
| GAM-DYLIGHT™ 650-4xPEG_20x | 1.0 | 1.0 | 0.8 | 0.8 | 1.6 | 0.9 | 1.3 |

NA = No Addition

Results shown in FIG. 7 and Table 15 demonstrate the effect of the addition of NHS Acetate (2.5×, 5× and 10×) and MS(PEG)$_4$ (3.75×, 5×, 10×) spacers to GAM-DyLight™ 800-4×PEG-in a dot blot assay. Mouse IgG was serially diluted 1:2 from 1000 ng/dot. All DyLight™ 800-4×PEG-GAR secondary antibodies were diluted to 1/20000 of 1 mg/ml stock. This experiments shows that the addition of MS(PEG)$_4$ (3.75× and 5×) and NHS Acetate (5×) significantly enhanced the fluorescence intensity and sensitivity of base DyLight™ 800-4×PEG conjugate by 1.5 to 6-fold in a dot blot application.

TABLE 15

Effect of the addition of NHS Acetate (2.5X, 5X and 10X) or MS(PEG)$_4$ (3.75X, 5X, 10X)) GAM-DYLIGHT™ 800-4xPEG- in a Dot Blot Assay.

| FOLD OF IMPROVEMENT | NA | + 2.5X NHS Acetate | + 5X NHS Acetate | + 10X NHS Acetate | + 3.75X MS(PEG)$_4$ | + 5X MS(PEG)$_4$ | + 10X MS(PEG)$_4$ |
|---|---|---|---|---|---|---|---|
| GAM-DYLIGHT™ 800-4xPEG_5x | 1.0 | 1.7 | 0.2 | | 3.1 | 5.5 | 1.8 |
| GAM-DYLIGHT™ 800-4xPEG_7.5x | 1.0 | 0.6 | 1.4 | | 1.8 | 2.9 | 1.3 |
| GAM-DYLIGHT™ 800-4xPEG_10x | 1.0 | 1.7 | 1.3 | | 2.1 | 0.7 | 1.0 |
| GAM-DYLIGHT™ 800-4xPEG_15x | 1.0 | 1.3 | 1.6 | 1.2 | 3.1 | 1.3 | 1.9 |
| GAM-DYLIGHT™ 800-4xPEG_20x | 1.0 | 1.3 | 1.8 | 1.5 | 3.2 | 1.3 | 1.6 |

NA = No Addition

Results shown in FIG. 11 demonstrate the effect of NHS Acetate (2.5×, 5× and 10×) and MS(PEG)$_4$ (5×) and MS(PEG)$_8$ (5×) spacers addition to GAM-DyLight™ 550-2×PEG-GAR (at 12.5× molar excess of dye) in a dot blot assay. Mouse IgG was diluted 3 fold from 0.5 µg/well. All DyLight™ secondary antibodies were diluted to 1/5000 of 1 mg/ml stock. These dot blot assays showed that the addition of MS(PEG)$_4$ (5×) and NHS acetate (2.5× and 5×) significantly enhanced the fluorescence intensity and sensitivity of base DyLight™ 550-2×PEG conjugates by at least by 2-fold. Conjugates prepared with longer chain MS(PEG)$_8$ did not show significant improvement over the base conjugate.

Results shown in FIG. 12 demonstrate the effect of addition of NHS Acetate (2.5×, 5×) and MS(PEG)$_4$ (5×) spacers to GAM-DyLight™ 680-4×PEG-GAR (at 10× molar excess of dye) in a dot blot assay. Mouse IgG was serially diluted 1:2 from 1000 ng/dot. All DyLight™ 680-4×PEG-GAR secondary antibodies were diluted to 1/20000 of 1 mg/ml stock. These dot blot assays show that the addition of MS(PEG)$_4$ (5×) and NHS acetate (2.5× and 5×) significantly enhanced the fluorescence intensity and sensitivity of base DyLight™ 680-4×PEG conjugate.

Example 3: Plate Assay Methods

To prepare plates, eleven (1:1) serial dilutions of Mouse or Rabbit IgG starting from 10 µg/ml were prepared. 1004 of each dilution was placed in 96-well plates in the corresponding well from 1-11 from highest to lowest using a 300 µL 12-channel multi pipette; PBS was added to the last column (#12; negative control). This was repeated from row A to H. The plates were incubated overnight and then blocked and incubated with SuperBlock™ Blocking Buffer (Thermo Fisher, cat. not. 37515) as follows: two times two hundred µL for 5 minutes followed by one times 200 µL for ten minutes. The plates were allowed to dry and then stored desiccated at 4° C.

Mouse IgG- or Rabbit IgG-coated plates were washed two times 200 µL with PBST 20 then one time with PBS. The secondary antibody conjugates were diluted in TBS or PBS. Secondary antibody conjugates were diluted 1:100 (DyLight™ 488 and 550-2×PEG, DyLight™ 650-4×PEG DyLight™ 680-4×PEG and DyLight™ 800-4×PEG conjugates). 1004 of the relevant conjugates GAM in Mouse IgG-coated plate, GAR in Rabbit IgG coated plate were added to the plate well. Each dilution was added to different rows for each conjugate to be tested. All comparisons were made on the same plate. The plates were incubated for sixty minutes. Plates were washed three time 2004 with TBST or PBST buffer. 1004 of PBS was added to each row in each well. The fluorescence intensity was measured using the VariosKan instrument or Image the fluorescent signal with a suitable imager, such as ChemiDoc MP (488, 550, 650, 680 nm) and LiCOR Odyssey CLx (650, 680, 800 nm).

Example 4: Immunofluorescence (IFC) Methods (i.e., Cellular Imaging Methods)

Method #1: Frozen U20S cell plates stored at −80° C. were thawed for thirty minutes at 50° C. Storage buffer (PBS) was removed and the cells were permeabilized for fifteen minutes (100 µl/well) with 0.1% Triton-X100 in 1×PBS buffer. Plates were blocked for thirty minutes in 2% BSA/PBS-0.1% Triton-X100 blockers. Primary antibody Mouse anti-PDI or Rabbit anti-HDAC2 (10 µg/ml) (cat. no. PA1-861, Life Technologies Corp., Carlsbad, Calif.), diluted in 2% BSA/PBS-0.1% Triton-X100 was added to the plate and incubated for one hour at RT. Negative controls contain only 2% BSA/PBS-0.1% Triton-X100 blocker. After incubation, the primary antibody solution was removed from the plate and the plate was washed three times 100 µl/well PBST and one time 100 µl/well PBS. Next, GAM or GAR secondary antibodies labeled with various molar excesses of dyes were diluted to 4 µg/ml in PBS and incubated for one hour at room temperature. The plates were washed three times 100 µl/well PBST and 1×100 µl/well PBS and Hoechst 33342 (cat. no. 62249, Thermo Scientific, Waltham, Mass.), (diluted to 0.1 µg/ml in PBS) was added to each well (100 µl/well). The plates were scanned on ArrayScan™ Plate Reader VTI3, 20× objective.

Method #2: Certain experiments were done in A549 cells in 384-well plates. Primary antibody was used at the same concentration (1 µg/ml) with varying dilutions of secondary. pH2AX measurements in etoposide (50 µM for 3 hours, Tocris Bioscience, cat no. 12-261-00) treated cells were used to measure B Signal/Noise (S/N, also referred to as Signal to Background), and brightness was used to compare different antibodies. Secondary antibody conjugates were tested at 4 different dilutions (0.5, 1, 2 and 4 mg/ml). Standard procedures were used for antibody staining: 4% formaldehyde fixation for fifteen minutes. Permeabilization was performed in 0.5% Triton x-100 for ten minutes. Blocking was performed with 3% BSA for thirty minutes. Primary antibody incubation was carried out at RT for one hour. This was followed by three washes with PBS. Secondary antibody conjugates were incubated at RT for one hour followed by three washes with PBS. The cells were analyzed on ArrayScan™ VTI (Thermo Fisher).

Results shown in FIG. 13 and Tables 16 and 17 demonstrate the effect of NHS acetate (2.5× and 5×) and MS(PEG)$_4$ (3.75×) spacer addition to GAM-DyLight™ 488 (13A) and GAR-DyLight™ 488 ((13B) at 7.5× to 20× molar excess of dye) in a cellular imaging application. DyLight™ 488-GAM and DyLight™ 488-GAR. A549 cells were stained with a pH2Ax primary antibody diluted to 1/1000 of the 1 mg/ml stock. All DyLight™ 488 secondary antibodies were diluted to 1/250 of the 1 mg/ml stock. NHS acetate added to the conjugation mix provided an improvement of signal/background as compared to the base conjugates at 15× dye molar excesses; ranging from 1.4 to 1.5-fold (GAM) and 1.1 to 1.6-fold (GAR). For GAM conjugates the most significant improvement was observed with NHS Acetate at 5× and with MS(PEG)$_4$ at 3.75×, and for GAR conjugates the more noticeable improvement was observed with NHS Acetate at 2.5× and with MS(PEG)$_4$ at 3.75×.

TABLE 16

Effect of NHS Acetate (2.5X, 5X and 10X) or MS(PEG)$_4$ (3.75X) addition in the conjugation of GAM-DYLIGHT ™ 488 at 5X-20X molar excess in a Cellular Imaging application-DYLIGHT ™ 488-GAM

| FOLD OF IMPROVEMENT | NA | +2.5X NHS Acetate | +5X NHS Acetate | +3.75X MS(PEG)$_4$ |
|---|---|---|---|---|
| DYLIGHT ™ 488_7.5x | 1.00 | 1.07 | 1.14 | 1.23 |
| DYLIGHT ™ 488_10x | 1.00 | 1.04 | 1.13 | 1.17 |
| DYLIGHT ™ 488_15x | 1.00 | 1.11 | 1.48 | 1.53 |
| DYLIGHT ™ 488_20x | 1.00 | 0.72 | 1.09 | 1.07 |

NA = No Addition

TABLE 17

Effect of NHS Acetate (2.5X, 5X and 10X) or
MS(PEG)$_4$ (3.75X) addition in the
conjugation of GAR-DYLIGHT ™ 488
at 5X-20X molar excess in a Cellular Imaging
application-DYLIGHT ™ 488-GAR

| FOLD OF IMPROVEMENT | NA | +2.5X NHS Acetate | +5X NHS Acetate | +3.75X MS(PEG)$_4$ |
|---|---|---|---|---|
| DYLIGHT ™ 488_7.5x | 1.00 | 1.13 | 1.07 | 1.13 |
| DYLIGHT ™ 488_10x | 1.00 | 1.20 | 1.21 | 1.02 |
| DYLIGHT ™ 488_15x | 1.00 | 1.60 | 1.31 | 1.67 |
| DYLIGHT ™ 488_20x | 1.00 | 1.23 | 1.14 | 1.11 |

NA—No Addition

Results shown in FIG. 14 and Table 18 demonstrate the effect of NHS Acetate (2.5×, 5× and 10×) and MS(PEG)$_4$ (3.75×, 5× and 10×) on GAM-DyLight™ 550-2XPEG-GAM (at 7.5× to 20× molar excess of dye) in a cellular fluorescence imaging application. U2OS cells were stained with an anti-PDI primary antibody diluted to 1/100 of the 1 mg/ml stock. All DyLight™ 550-2×PEG-GAM secondary antibodies were diluted to 1/250 of the 1 mg/ml stock. In this cellular imaging application, the addition of 5×NHS Acetate generated about 50% improvement as compared to the base conjugate (made without the additives) for DyLight™ 550-2×PEG GAM conjugate at 12.5× dye molar excess, and addition of 3.75× MS(PEG)$_4$ resulted in about 50% improvement over the base conjugates at 20× dye molar excess.

TABLE 18

Effect of 2.5X to 10X NHS Acetate and MS(PEG)4 3.75X to 10X on fluorescence intensity of GAM-DYLIGHT ™ 550-2xPEG) in a Cellular Imaging application

| FOLD OF IMPROVEMENT | NA | + 2.5X NHS Acetate | + 5X NHS Acetate | + 10X NHS Acetate | + 3.75X MS(PEG)$_4$ | + 5X MS(PEG)$_4$ | + 10X MS(PEG)$_4$ |
|---|---|---|---|---|---|---|---|
| GAM-DYLIGHT ™ 550-2xPEG_7.5x | 1.0 | 0.5 | 0.7 | | 0.5 | 0.9 | 0.7 |
| GAM-DYLIGHT ™ 550-2xPEG_10x | 1.0 | 1.7 | 1.7 | | 0.9 | 1.4 | 1.5 |
| GAM-DYLIGHT ™ 550-2xPEG_12.5x | 1.0 | 1.8 | 2.0 | | 0.9 | 1.1 | 1.2 |
| GAM-DYLIGHT ™ 550-2xPEG_15x | 1.0 | 2.2 | 2.2 | 1.9 | 1.3 | 1.9 | 1.1 |
| GAM-DYLIGHT ™ 550-2xPEG_20x | 1.0 | 1.7 | 1.3 | 1.0 | 1.2 | 1.2 | 1.0 |

NA = No Addition

Results are shown in FIG. 15 and Table 19 for an experiment testing the effect of NHS Acetate (2.5×, 5× and 10×) and MS(PEG)$_4$ (3.75×, 5×, 10×) spacer to GAM-DyLight™ 650-4×PEG) in a cellular imaging application. U2OS cells were stained with anti-PDI primary antibody diluted to 1/100 of 1 mg/ml stock. All DyLight™ 650-4× PEG-GAM secondary antibodies were diluted to 1/250 of 1 mg/ml stock. In this cellular imaging application, the addition of NHS Acetate-5× generated about 70% improvement as compared to the base conjugate (made without the additives) for DyLight™ 650-4×PEG-GAM conjugate at 20× molar excess, and MS(PEG)$_4$-3.75× showed about 90% improvement over the base conjugates at 20× molar excess.

TABLE 19

Effect of the addition of NHS Acetate (2.5X, 5X and 10X) or MS(PEG)4 (3.75X, 5X, 10X) GAM-DYLIGHT ™ 650-4xPEG)-Cellular Imaging application.

| FOLD OF IMPROVEMENT | NA | + 2.5X NHS Acetate | + 5X NHS Acetate | + 10X NHS Acetate | + 3.75X MS(PEG)$_4$ | + 5X MS(PEG)$_4$ | + 10X MS(PEG)$_4$ |
|---|---|---|---|---|---|---|---|
| GAM-DYLIGHT ™ 650-4xPEG_5x | 1.0 | 1.0 | 1.0 | | 0.9 | 1.2 | 1.1 |
| GAM-DYLIGHT ™ 650-4xPEG_7.5x | 1.0 | 0.5 | 0.5 | | 0.5 | 0.4 | 1.6 |
| GAM-DYLIGHT ™ 650-4xPEG_10x | 1.0 | 1.3 | 1.7 | | 0.9 | 1.0 | 1.5 |
| GAM-DYLIGHT ™ 650-4xPEG_15x | 1.0 | 0.8 | 0.8 | 0.8 | 0.8 | 0.7 | 2.2 |
| GAM-DYLIGHT ™ 650-4xPEG_20x | 1.0 | 1.0 | 0.9 | 1.1 | 1.9 | 1.1 | 1.3 |

NA = No Addition

Results are shown in FIG. 16 and Table 20 for an experiment testing the effect of the addition of NHS Acetate (2.5×, 5× and 10×) and MS(PEG)$_4$ (3.3.75×, 5×, 10×) spacer to the detectable fluorescence level of GAM-DYLIGHT™ 680-4×PEG) in a cellular imaging application. U2OS cells were stained with mouse anti-PDI primary antibody diluted to 1/100 of 1 mg/ml stock. All DYLIGHT™ 680-4×PEG-GAM secondary antibodies were diluted to 1/250 of 1 mg/ml stock: In this cellular imaging application, the addition of NHS Acetate-5× generated about 70% improvement for dyes conjugates at both 7.5× and 10× as compared to the base conjugate (made without the additives) for DYLIGHT™ 680-4×PEG. GAM conjugate at molar excesses of 15× molar excess and MS(PEG)$_4$-3.75× showed about 80% improvement over the base conjugates at 15× molar excesses.

TABLE 20

Effect of the addition of NHS Acetate (2.5X, 5X and 10X) or MS(PEG)4 (3.3.75X, 5X, 10X) GAM-DYLIGHT ™ 680-4xPEG)-Cellular Imaging application

| FOLD OF IMPROVEMENT | NA | + 2.5X NHS Acetate | + 5X NHS Acetate | + 10X NHS Acetate | + 3.75X MS(PEG)$_4$ | + 5X MS(PEG)$_4$ | + 10X MS(PEG)$_4$ |
|---|---|---|---|---|---|---|---|
| GAM-DYLIGHT ™ 680-4xPEG_5x | 1.0 | 0.8 | 0.7 | | 0.7 | 1.0 | 0.8 |
| GAM-DYLIGHT ™ 680-4xPEG_7.5x | 1.0 | 1.2 | 1.7 | | 1.1 | 1.1 | 1.1 |
| GAM-DYLIGHT ™ 680-4xPEG_10x | 1.0 | 1.7 | 1.7 | | 1.1 | 1.5 | 1.5 |
| GAM-DYLIGHT ™ 680-4xPEG_15x | 1.0 | 1.4 | 1.2 | 1.1 | 1.8 | 1.3 | 1.4 |
| GAM-DYLIGHT ™ 680-4xPEG_20x | 1.0 | 0.8 | 0.9 | 1.1 | 1.0 | 1.1 | 1.1 |

NA = No Addition

Results

The use of spacer agents such as NHS-Acetate, NHS-MS (PEG) and NHS-Betaine increased fluorescent signal sensitivity and intensity above optimal D/P levels that typically result in quenching. This was demonstrated by labeling goat anti-mouse (GAM) and goat anti-rabbit (GAR) secondary antibodies with NHS-DYLIGHT™ 488, NHS-DYLIGHT™ 550 2XPEG, NHS-DYLIGHT™ 650 4XPEG, NHS-DYLIGHT™ 680 4XPEG, NHS-DYLIGHT™ 800 4XPEG in combination with spacer agents which include, but are not limited to, NHS-Acetate and NHS-MS(PEG)$_4$, NHS-MS(PEG)$_8$ and NHS-MS(PEG)$_{12}$. Our calculations of D/P value following dye conjugation and purification demonstrated that the addition of the spacer agents did not make significant differences to the D/P ratios indicating that these reagents and the fluorophores labeled different primary amines on the antibody (i.e., they don't compete for the same primary amines).

Conjugates made with different dye and spacer agents were tested in a variety of applications including IFC, Western blotting, dot blotting or IgG Binding plate-based assays. In each instance, with certain spacer agents at certain molar excess values of the spacer agent to the dye, an increase in fluorescence intensity was observed when spacer agents were used as compared to controls lacking spacer agents.

In addition to the above described experiments, antibodies labeled with NHS-Rhodamine and conjugated with a variety of NHS-Betaine concentrations (Betaine 2.5, Betaine 5, Betaine 10 molar ratios) displayed an increase in total fluorescence when the antibodies were conjugated with Betaine as the spacer modification reagent. See FIG. 17 and Tables 21 and 22 below. Amongst the different Betaine chain lengths, Betaine 10 had a positive effect on TAMRA at all molar excesses of the dyes and on ALEXA FLUOR® 555 above a D/P ratio of 12 (data not shown).

TABLE 21

Effect of 2.5X to 10X Betaine on fluorescence of TAMRA-GAM conjugates.

| NHS-Betaine MR | NHS-TAMRA MR | TAMRA/ IgG DOL | Relative Quantum Yield | Total Fluorescence |
|---|---|---|---|---|
| 2.5 | 5 | NA | NA | NA |
| 2.5 | 10 | 6.3 | 0.4 | 2.52 |
| 2.5 | 20 | 8.6 | 0.3 | 2.58 |

TABLE 21-continued

Effect of 2.5X to 10X Betaine on fluorescence of TAMRA-GAM conjugates.

| NHS-Betaine MR | NHS-TAMRA MR | TAMRA/ IgG DOL | Relative Quantum Yield | Total Fluorescence |
|---|---|---|---|---|
| 5 | 5 | 5.9 | 0.56 | 3.3 |
| 5 | 10 | 7.1 | 0.34 | 2.41 |
| 5 | 20 | 6.4 | 0.18 | 1.15 |
| 10 | 5 | 5.4 | 0.56 | 3.02 |
| 10 | 10 | 8.4 | 0.5 | 4.2 |
| 10 | 20 | 15.7 | 0.34 | 5.34 |
| 0 | 5 | 4.2 | 0.54 | 2.27 |
| 0 | 10 | 6.7 | 0.42 | 2.81 |
| 0 | 20 | 11.4 | 0.38 | 4.33 |

MR = Molar Ratio
DOL = Degree of Labeling

Example 5: Reaction of Goat Anti-Mouse IgG (GAM) and 5-(and-6)-Carboxytetramethylrhodamine, Succinimidyl Ester (5(6)-TAMRA-SE) with and without N,N,N-Trimethylglycine-N-Hydroxysuccinimide Ester Bromide (Betaine-SE)

TAMRA-SE was weighed out and made up as a stock solution at 10 mg/mL in anhydrous DMSO and Betaine-SE was weighed out and made up at a stock of 4 mg/mL in anhydrous DMSO. The DMSO solutions were then transferred into reaction vials with the TAMRA-SE+/−Betaine-SE measured into the vials based on a 5, 10, or 20-fold molar ratio of dye to IgG and the equivalent of molar ratio 0 or 10 Betaine-SE to IgG also added to the vials.

Separately, 0.417 mL (3.5 mg) of a 8.4 mg/mL solution of GAM in 10 mM potassium phosphate, 150 mM sodium chloride buffer (PBS) was measured into a plastic tube and the pH raised to >8.0 with 42 µL of 1M sodium bicarbonate, pH 9.0. 0.5 mg of the GAM solution was added to the reaction vials containing SE and reacted for 1 hour at RT. The dye-protein conjugates were separated from free dye and Betaine by size exclusion chromatography using 5-0.75×20 cm columns packed with BioRad™ Bio-Gel® P-30 fine in PBS and eluted with same. The initial protein-containing band from each column was collected.

Absorbance spectra were obtained on a Perkin-Elmer Lambda 35 UV/Vis spectrometer, and the degree of substitution (DOS) or moles dye/mole GAM was determined for each sample. Fluorescence emission spectra were obtained using a Perkin Elmer LS 55 Fluorescence Spectrometer, using samples with matched optical density at 545 nm and excited at 545 nm. Emission data collected from 550-750 nm. Relative quantum yield (RQY) was measured as the area of the sample spectrum/area of the dye standard spectrum. Total fluorescence was then calculated as the product of the RQY*DOS.

TABLE 22

Total Fluorescent Output of Differing Molar Ratios of TAMRA/GAM

| TAMRA/GAM (Molar Ratios) | 5 | 10 | 20 |
|---|---|---|---|
| TAMRA-GAM and Betaine-SE added at MR = 10 | 3.02 | 4.2 | 5.34 |
| TAMRA-GAM (No Betaine-SE) | 2.27 | 2.81 | 4.33 |

Example 6: Reaction of Goat Anti-Mouse IgG (GAM) and Alexa Fluor® 488 Carboxylic Acid, Succinimidyl Ester, Dilithium Salt (AF488-SE) with and without 1,3-Propane Sultone (3-Hydroxy-1-Propanesulfonic Acid γ-Sultone)

AF488-SE was weighed out and made up as a stock solution at 10 mg/mL in anhydrous DMSO and Propane sultone was weighed out and made up at a stock of 1 mg/mL in E-Pure H₂O.

0.357 mL (4.0 mg) of a 11.2 mg/mL solution of GAM in 10 mM potassium phosphate, 150 mM sodium chloride buffer (PBS) was measured into a plastic tube and the pH raised to >8.0 with 36 µL of 1M sodium bicarbonate, pH 9.0. 0.5 mg of the GAM solution was transferred to reaction vials and reacted with a 0, 2, 5, or 10-fold molar excess of propane sultone for 2 minutes and then AF488 stock was added to the mixtures in an 8 or 15-fold molar excess over the GAM and let react for 1 hour at room temperature. The dye-protein conjugates were separated from free dye and Propane sultone by size exclusion chromatography using 5-0.75×20 cm columns packed with BioRad™ Bio-Gel® P-30 fine in PBS and eluted with same. The initial protein-containing band from each column was collected.

Absorbance spectra were obtained on a Perkin-Elmer Lambda 35 UV/Vis spectrometer, and the degree of substitution (DOS) or moles dye/mole GAM was determined for each sample. Fluorescence emission spectra were obtained using a Perkin Elmer LS 55 Fluorescence Spectrometer, using samples with matched optical density at 475 nm and excited at 475 nm. Emission data collected from 480-800 nm. Relative quantum yield (RQY) was measured as the area of the sample spectrum/area of the dye standard spectrum. Total fluorescence was then calculated as the product of the RQY*DOS.

TABLE 23

Total Fluorescent Output of Differing Molar Ratios of AF 488/GAM

| AF488/GAM(Molar Ratios) | 8 | 15 |
|---|---|---|
| AF488-GAM + propanesultone/GAM MR = 2 | 2.52 | 3.67 |
| AF488-GAM + propanesultone/GAM MR = 5 | 2.62 | 3.73 |
| AF488-GAM + propanesultone/GAM MR = 10 | 2.69 | 3.86 |
| AF488-GAM control (no propanesultone) |  | 3.56 |

Example 7: Labeling of SK3 Mouse Anti-Human CD4 Azide with 20 kDa 8-Arm PEG Amine (20K8 PEG) Modified with Alexa Fluor® 647 NHS Ester, Tris(Triethylammonium Salt) (AF647-SE)

Alexa Fluor® 647 NHS/Succinimidyl Ester (Thermo Fisher Scientific, cat. no. A37573), abbreviated as "AF647-SE", was weighed out and made up as a stock solution at 32 mM in anhydrous DMSO (Thermo Fisher Scientific, D12345). Click-iT™ SDP Ester sDIBO Alkyne (sDIBO) (Thermo Fisher Scientific, cat. no. C20025) was made up as a stock solution at 9 mg/mL in anhydrous DMSO. 8arm PEG Amine (hexaglycerol), HCl salt (JenKem, Plano, Tex. 75024, cat. no. 8ARM-NH₂HCl), abbreviated as "20K8 PEG", having the following structure:

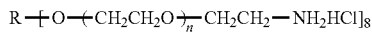

R = hexaglycerol core structure was weighed out and prepared as a stock solution at 40 mg/mL in anhydrous DMSO.

To a plastic tube, 300 µL of 20K8 PEG stock solution, 176 µL of sDIBO stock solution (2.4-fold molar excess/20K8 PEG) and 6 µL of neat Triethylamine (TEA) was added and allowed to react for 3 hours at 25° C. After reaction, 300 µL of the AF647-SE stock solution (2-fold molar excess/PEG-amine) was added to the tube and the reaction proceeded overnight at 25° C. The AF647-20K8 PEG-sDIBO constructs were purified from free dye and sDIBO by size exclusion chromatography using a 1×30 cm column packed with BioRad Bio-Gel® P-10F in PBS and eluted in the same. The initial dye-containing fractions were collected and concentrated using EMD Millipore AMICON™ Ultra-4 10 kDa centrifugal filters.

Azido (PEO)₄ propionic acid, succinimidyl ester (Thermo Fisher Scientific, cat. no. A10280), abbreviated as "Azide-SE", was weighed out and made up as a stock solution at 10 mM in anhydrous DMSO (Thermo Fisher Scientific, D12345). 266 µL SK3 mouse anti-human CD4 antibody (2.5 mg) and 134 µL PBS were added to a plastic tube and the pH was raised to >8.0 with 50 µL 1M sodium bicarbonate, pH 9.0. 8.3 µl of Azide-SE stock solution (5 fold molar excess/antibody) and 42 µl of DMSO were added to the antibody solution. The reaction was allowed to proceed for 2 hours at 25° C. The azido-SK3 antibody was purified using 2 mL BioRad Bio-Gel® P-30M spin columns. Azido-SK3 antibody was prepared with 5-fold to 20-fold excess of Azide-SE to antibody.

24.2 μL of a 2 mM solution of AF647-20K8 PEG-sDIBO (concentration of DIBO) and 116 μL of a 4.3 mg/mL azido-SK3 were combined in a plastic tube. 360 μL of PBS were added to bring the final concentration of the solution to 100 μM AF647-20K8 PEG-sDIBO (concentration of DIBO) and 1 mg/mL azido-SK3 antibody. The click reaction was allowed to proceed for 2 hours at 37° C. followed by quenching with 5 mM NaN₃ for 1 hour at room temperature. AF647-20K8 PEG-SK3 conjugates were diluted to 0.5 mg/mL in PBS. Conjugation reactions were carried out at final DIBO concentrations between 100 and 600 μM, with azido-SK3 antibody at 1-3 mg/mL, at reaction temperatures between 25° C. and 37° C., for 2 hours to 20 hours. Specific conditions per experimental run are set out in Table 24.

24.2 μL of a 2 mM solution of AF647-20K8 PEG-sDIBO (concentration of DIBO) and 116 μL of a 4.3 mg/mL azido-SK3 were combined in a plastic tube. 360 μL of PBS were added to bring the final concentration of the solution to 100 μM AF647-20K8 PEG-sDIBO (concentration of DIBO) and 1 mg/mL azido-SK3 antibody. The click reaction was allowed to proceed for 2 hours at 37° C. followed by quenching with 5 mM NaN₃ for 1 hour at room temperature. Conjugates were purified and concentrated using EMD Millipore AMICON™ Ultra-4 100 kDa centrifugal filters. AF647-20K8 PEG-SK3 conjugates were diluted to 0.5 mg/mL in PBS. Conjugation reactions were carried out at final DIBO concentrations between 100 and 600 μM, with azido-SK3 antibody at 1-3 mg/mL, at reaction temperatures between 25° C. and 37° C., for 2 hours to 20 hours. Specific conditions per experimental run are set out in Table 24.

TABLE 24

Conjugation Conditions

| | SK3-N₃ | | | Click Incubation condition | | |
|---|---|---|---|---|---|---|
| Example | MR[1] | DOS[2] | starPEG[3] | SK3 mg/mL[4] | starPEG DIBO μM[5] | time/temp[6] |
| sa1 | 5 | 3 | HG 20kD | 1 | 100 | 2h/37° C. |
| sa2 | 10 | 6.1 | HG 20kD | 1 | 100 | 2h/37° C. |
| sa3 | 20 | 12 | HG 20kD | 1 | 100 | 2h/37° C. |
| sa4 | 5 | 3 | HG 20kD | 1 | 200 | 2h/37° C. |
| sa5 | 10 | 6.1 | HG 20kD | 1 | 200 | 2h/37° C. |
| sa6 | 20 | 12 | HG 20kD | 1 | 200 | 2h/37° C. |
| sa2* | 10 | 6.1 | HG 20kD | 1 | 100 | 20h/25° C. |
| sa7 | 5 | 3 | TP 20kD | 1 | 100 | 2h/37° C. |
| sa8 | 10 | 6.1 | TP 20kD | 1 | 100 | 2h/37° C. |
| sa9 | 20 | 12 | TP 20kD | 1 | 100 | 2h/37° C. |
| sa10 | 5 | 3 | TP 20kD | 1 | 200 | 2h/37° C. |
| sa11 | 10 | 6.1 | TP 20kD | 1 | 200 | 2h/37° C. |
| sa12 | 20 | 12 | TP 20kD | 1 | 200 | 2h/37° C. |
| sa8* | 10 | 6.1 | TP 20kD | 1 | 100 | 20h/25° C. |
| sa13 | 10 | 6.1 | HG 20kD | 3 | 600 | 3h/37° C. |
| sa14 | 20 | 12 | HG 20kD | 3 | 600 | 3h/37° C. |

[1]MR: Molar Ratio;
x-fold excess used to tag SK3 antibody with Azide-SE:antibody (mole/mole).
[2]DOS: degree of substitution, number of azide groups incorporated per antibody molecule.
[3]starPEG: indicates MW of starPEG (20 kD) and core.
HG: hexaglycerol,
TP: tripentaerythritol.
[4]In the click incubation SK3 was present at indicated concentrations in mg/mL (specified for each example).
[5]The starPEG DIBO during the click conjugation was present at the indicated concentrations in μM.
[6]The click reactions were carried out for the indicated times at the indicated temperatures.

Example 8: Quantum Yield Characterization of Branched PEG AF647 Constructs

To prepare samples for quantum yield measurement, solutions of AF647 Branched PEG constructs (AF647-2K4, AF647-10K4, AF647-10K8 and AF647-20K8) were diluted to a final dye concentration of 0.16 μM in deionized water. Quantum yield (Φ) was measured using a Hamamatsu Absolute PL Quantum Yield Spectrometer. Quantum yields for the Branched PEG constructs were compared to that of the free dye to determine the degree of quenching in the final constructs. Additionally, the brightness was determined to determine the fluorescent enhancement achieved using the branched PEG spacers. The smallest construct, AF647-2K4 (2,000 molecular weight branched PEG with four arms) showed the greatest quenching (20% QY of the free dye, 0.2 Fluorescent Ratio) and had the lowest overall improvement in the total fluorescence. The greatest fluorescence enhancement was seen for higher molecular weight constructs, with either 4 or 8 arms (AF647-10K4 and AF647-20K8) where up to 89% of the fluorescence quantum yield was retained of the free dye (Fluorescent Ratio of 0.9), and up to 5.8 fold improvement in brightness was noted.

TABLE 25

Effect of Branched PEG spacers on the percent quantum yield (QY) and brightness (B) of ALEXA FLUOR® 647

| Sample | Dyes/ Molecule (N) | Quantum Yield (QY) | % QY of Free Dye (Fluorescent Ratio) | Brightness, B (QY × ε × N) AU | Brightness Ratio to Free Dye |
|---|---|---|---|---|---|
| AF647 | 1 | 0.404 | 100% (1.0) | 1.09E+05 | 1.0 |
| AF647-2K4 | 4 | 0.087 | 22% (0.2) | 9.40E+04 | 0.9 |
| AF647-10K4 | 4 | 0.359 | 89% (0.9) | 3.88E+05 | 3.6 |
| AF647-10K8 | 8 | 0.145 | 36% (0.4) | 3.13E+05 | 2.9 |
| AF647-20K8 | 8 | 0.295 | 73% (0.7) | 6.37E+05 | 5.8 |

An assumption is made that effectively one fluorescent label is attached to the terminus of each arm. In other words, an assumption is made that the PEG molecules have been labeled to saturation, thus N = number of arms/polymer.
$\epsilon = 270,000 \text{ cm}^{-1}\text{M}^{-1}$ for ALEXA FLUOR® 647

Example 9: Flow Cytometry Evaluation of AF647-20K8 PEG-SK3 Constructs

Freshly collected anti-coagulated whole blood (human) was lysed using ACK lysis buffer for 20 minutes at room temperature. White blood cells were isolated by centrifugation (400×g, 5 mins.) and washes in 1% bovine serum albumin/PBS twice (1% BSA/PBS). After isolation, the total number of white blood cells was determined using the COUNTESS® Automated Cell Counter and then diluted to 10 million cells per mL. One million cells/well in a 96 well plate were stained with the AF647-20K8 PEG-SK3 conjugates using a 7 point titration of 1 μg to 0.015 μg of antibody. Stained cells were washed twice with 1% BSA/PBS. Analysis of the stained cells was carried out using the ATTUNE™ NxT Flow Cytometer and compared to APC (Thermo Fisher Scientific, cat. no. MHCD0405), ALEXA FLUOR® 488 (Invitrogen, cat. no. MHCD0420), FITC (Thermo Fisher Scientific, cat. no. MA1-81103) and BRILLIANT VIOLET™ 605 (BioLegend, San Diego, Calif., cat. no. 300555) CD4 conjugates.

FIG. 22 shows a histogram plot of CD4 positive lymphocyte cells as a function of fluorescence intensity in the RL1 channel of the ATTUNE™ NxT Flow Cytometer. ALEXA FLUOR® 647 conjugated to CD4 is shown as a dashed line, and the AF647-20K8 PEG-SK3 conjugates are shown as dotted or solid lines. Compared to the AF647 conjugate alone, the StarPEG conjugates show a greater that 0.5 log increase in brightness. FIG. 23 shows plotted signal to noise (S/N) and percent positive (% Positive) as a function of conjugate concentration in the flow cytometry experiment. It is shown that the StarPEG constructs (here B1 and B2) have up to 2.5 fold increase in S/N versus the APC CD4 benchmark conjugate, and up to 2 fold increase in S/N versus the AF647 CD4 benchmark conjugate while retaining the ability to accurately assess the number of CD4 positive cells in the sample.

Example 10: Conjugation of ALEXA FLUOR® 488 to an Amino Dextran Scaffold

Preparation of 70 kD amino dextran AF488 scaffold: 10 mg of amino dextran (70,000 MW, 20 amino groups; Thermo Fisher Scientific, Cat. No. D1862) was dissolved in 1.2 ml of dry DMSO containing 1.0 µl of DIEA. 0.9 mg of ALEXA FLUOR® 488 succinimidyl ester lithium salt (643 MF; Thermo Fisher Scientific, Cat. No. A20000) was added to solution and the mixture was stirred for 3.5 hours at ambient temperature. The solution was diluted with 12 mL of ethyl acetate and the resulting suspension was centrifuged. The supernatant was discarded and the solid material was shaken with 10 mL of fresh ethyl acetate and centrifuged. This washing was repeated 3 more times with 10 mL of fresh ethyl acetate and the resulting precipitate was dried in vacuum. The solid was re-dissolved in 0.5 ml of water and solution put in 10 cm Spectra/Por Dialysis membrane (Spectrum Labs, MWCO 12-14,000 flat width 10 mm) clipped from both side. The dialysis membrane was slowly stirred in 1 L of water for 1 week. The water was replaced twice per day. The dialysis membrane was open from one end and solution was lyophilized to give amino dextran ALEXA FLUOR® scaffold. The measured DOL is 9.7 and relative QY is 0.6 (referenced to QY of ALEXA FLUOR® 488).

Attaching thiol linker to 70 kD amino dextran AF488 scaffold: Amino dextran AF488 scaffold (4.5 mg) was dissolved in 0.5 mL of DMSO containing 0.055 µL of N,N-Diisopropylethylamine (DIEA). Succinimidyl 3-(2-pyridyldithio)propionate (SPDP) (20 µg) was added to solution and the mixture was kept at ambient temperature overnight and then capped with acetic acid succimidyl ester (1.0 mg, 3 hrs). The solution was diluted with 10 mL of ethyl acetate. The resulting suspension was centrifuged and supernatant discarded. The solid was shaken with 10 mL of fresh ethyl acetate and centrifuged. The washing was repeated 5 more times. The resulting solid was dried in vacuum. The measured DOL is 0.74. This material was re-dissolved in 2 mL of water and 16 mg of DTT was added to solution. The mixture was stirred for 5 min and loaded on G15 SEPHADEX® column, the product was eluted with DE water as green fluorescent solution which was used for conjugation to SMCC modified streptavidin. The determined concentration was 48 µM (by dye adsorption).

Conjugation of amino dextran AF488 scaffold modified with thiol linker to SMCC modified streptavidin: SMCC modified streptavidin (35 µL solution in water) was treated with 1, 2, 3 and 4 equivalents of thiol modified amino dextran AF488 scaffold (48 µM solution in water). The reaction was carried out at ambient temperature for 3 hours and after that reaction mixture was kept overnight at 4° C. overnight. The conjugates are purified on P100 size exclusion column with 10 nM PBS buffer.

TABLE 26

Streptavidin Labeled with 70 kD Amino dextran AF488 Scaffold (average of 9.7 molecules of dye per scaffold)

| DOL by Scaffold (Avg.) | DOL by Dye (Avg.) | QY | Brightness |
|---|---|---|---|
| 0.9 | 9.2 | 0.52 | 4.8 |
| 1.1 | 10.2 | 0.50 | 5.1 |
| 1.8 | 18 | 0.53 | 9.5 |
| 2.6 | 25.5 | 0.54 | 13.7 |

TABLE 27

Streptavidin labeled with AF488 dye

| DOL (Avg.) | QY | Brightness |
|---|---|---|
| 1.5 | 0.70 | 1.0 |
| 3.0 | 0.60 | 1.8 |
| 4.0 | 0.55 | 2.1 |
| 4.5 | 0.40 | 1.8 |
| 5.0 | 0.34 | 1.7 |

Results: As shown in Tables 26 and 27, conjugates made from the scaffold are brighter as compared to conjugates made from single AF488 dye. Also, QY of AF488 fluorophore drops from 0.70 to 0.34 for single dye conjugation in contrast to almost constant QY for labeling with the amino dextran scaffold.

We claim:

1. A composition, comprising a first conjugated antibody comprising two to ten fluorescent labels and two or more spacer molecules covalently attached to a first antibody, wherein the fluorescent labels and spacer molecules are not covalently attached to each other and wherein the composition exhibits increased fluorescence relative to a composition comprising a second conjugated antibody that is the same as and has a same degree of fluorescent labeling as the first conjugated antibody but that is lacking spacer molecules covalently attached to the second conjugated antibody, wherein the spacer molecules, which are covalently attached to the first antibody, are selected from sulfo-NHS-acetate, MS(PEG)$_4$, or NHS-Betaine.

2. The composition of claim 1, wherein the first conjugated antibody exhibits higher fluorescent emission levels than the second conjugated antibody wherein the higher fluorescent emission levels are the result of the spacer molecules increasing fluorescence of the first conjugated antibody.

3. The composition of claim 1, wherein the spacer molecules are conjugated to the first antibody to an amine group of a lysine residue.

4. The composition of claim 1, wherein the spacer molecules are sulfo-NHS-acetate.

5. The composition of claim 1, wherein the spacer molecules are MS-(PEG)$_4$.

6. The composition of claim 1 wherein the fluorescent labels are positively charged.

7. The composition of claim 1, wherein the fluorescent labels are dyes independently selected from a cyanine dye; a benzo-rhodamine dye; a 4,4-difluoro-4-bora-3a,4a-diaza-s-indacene dye; a fluorescein dye; a benzopyrillium dye, including derivatives thereof; a coumarin dye, a benzofuran dye; a quinoline dye; a quinazolinone dye; an indole dye; a furan dye; a benzazole dye; a borapolyazaindacene dye; or a xanthene dye.

8. The composition of claim 1, wherein the fluorescent labels comprise a moiety selected from xanthene, coumarin, cyanine, pyrene, oxazine, borapolyazaindacene, benzopyrylium, or carbopyronine.

9. The composition of claim 1, wherein the fluorescent labels comprise a moiety selected from is selected from dinitrophenyl, Fluorescein, hexachlorofluorescein, 4',5'-dichloro-2',7'-dimethoxy-5(6)-carboxyfluorescein, 6-carboxyl-X-rhodamine, tetrachlorofluorescein, tetramethyl rhodamine, or 7-hydroxy-9H-(1,3-dichloro-9,9-dimethylacridin-2-one) succinimidyl ester (DDAO-SE).

10. The composition of claim 1, wherein a number of the fluorescent labels conjugated to the first antibody is from 2 to 6.

11. The composition of claim 1, wherein a number of the spacer molecules conjugated to the first antibody is from 2 to 50.

12. The composition of claim 1, wherein the spacer molecules are in molar excess to the fluorescent labels in an amount from 0.1 to 25 fold.

13. The composition of claim 1, wherein the presence of the spacer molecules increases detectable fluorescence of the fluorescent labels by 20% to 5005.

14. The compistion of claim 1, wherein the first conjugated antibody comprises one or more of the following characteristics:
   (a) a Fluorescent Ratio on a per fluorescent label basis that is equal to or greater than 0.5,
   (b) at least four fluorescent labels conjugated to the first antibody, and/or
   (c) total fluorescence of the first conjugated antibody is at least 20 percent greater than fluorescence of an unconjugated fluorescent molecule.

* * * * *

UNITED STATES PATENT AND TRADEMARK OFFICE
CERTIFICATE OF CORRECTION

PATENT NO. : 11,865,191 B2
APPLICATION NO. : 16/882271
DATED : January 9, 2024
INVENTOR(S) : Desai et al.

It is certified that error appears in the above-identified patent and that said Letters Patent is hereby corrected as shown below:

In the Claims

Column 65, Line 61, Claim 2, "antibody wherein" should read --antibody, wherein--.

Column 66, Line 54, Claim 7, "benzopyrillium dye" should read --benzopyrylium dye--.

Column 66, Line 64, Claim 9, "labels comprise a moiety selected from is selected from" should read --labels comprise a moiety selected from--.

Column 67, Line 14, Claim 13, "20% to 5005" should read --20% to 500%--.

Column 67, Line 15, Claim 14, "compistion" should read --composition--.

Signed and Sealed this
Second Day of April, 2024

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(102)
<223> OTHER INFORMATION: Any amino acid
<220> FEATURE:
<221> NAME/KEY: MISC_FEATURE
<222> LOCATION: (3)..(102)
<223> OTHER INFORMATION: This region may encompass 2-100 residues
```

<400> SEQUENCE: 1

Cys Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Cys Cys
            100

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Cys Pro Gly Cys Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Gly Cys Cys Pro Gly Cys Cys Gly Gly Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Cys Gly Gly Lys Gly Asn Gly Gly Cys Gly Cys
1               5                   10

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(102)
<223> OTHER INFORMATION: Any amino acid

```
<220> FEATURE:
<221> NAME/KEY: MISC_FEATURE
<222> LOCATION: (3)..(102)
<223> OTHER INFORMATION: This region may encompass 2-100 residues
<220> FEATURE:
<221> NAME/KEY: MOD_RES
<222> LOCATION: (104)..(104)
<223> OTHER INFORMATION: Any amino acid
<220> FEATURE:
<221> NAME/KEY: MOD_RES
<222> LOCATION: (106)..(106)
<223> OTHER INFORMATION: Any amino acid

<400> SEQUENCE: 5

Cys Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Cys Xaa Cys Xaa
            100                 105

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```